US011352613B2

(12) United States Patent
Fuchs

(10) Patent No.: US 11,352,613 B2
(45) Date of Patent: Jun. 7, 2022

(54) ENGINEERED HUMAN EXTRACELLULAR DNASE ENZYMES

(71) Applicant: Neutrolis, Inc., Cambridge, MA (US)

(72) Inventor: Tobias A. Fuchs, Wellesley, MA (US)

(73) Assignee: Neutrolis, Inc., Cambridge, MA (US)

(*) Notice: Subject to any disclaimer, the term of this patent is extended or adjusted under 35 U.S.C. 154(b) by 0 days.

(21) Appl. No.: 17/509,991

(22) Filed: Oct. 25, 2021

(65) Prior Publication Data

US 2022/0042002 A1 Feb. 10, 2022

Related U.S. Application Data

(63) Continuation-in-part of application No. 17/427,974, filed as application No. PCT/US2020/016490 on Feb. 4, 2020.

(60) Provisional application No. 62/800,790, filed on Feb. 4, 2019.

(51) Int. Cl.
| | |
|---|---|
| *C12N 9/22* | (2006.01) |
| *A61K 38/46* | (2006.01) |
| *C07K 14/76* | (2006.01) |
| *A61K 39/00* | (2006.01) |

(52) U.S. Cl.
CPC ............ *C12N 9/22* (2013.01); *A61K 38/465* (2013.01); *C07K 14/76* (2013.01); *C12Y 301/21001* (2013.01); *A61K 2039/6081* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | |
|---|---|---|
| 6,482,626 B2 | 11/2002 | Baker et al. |
| 6,656,685 B2 | 12/2003 | Utermohlen et al. |
| 7,612,032 B2 | 11/2009 | Genkin et al. |
| 8,388,951 B2 | 3/2013 | Genkin et al. |
| 8,431,123 B2 | 4/2013 | Genkin et al. |
| 8,535,663 B2 | 9/2013 | Genkin et al. |
| 8,796,004 B2 | 8/2014 | Genkin et al. |
| 8,916,151 B2 | 12/2014 | Genkin et al. |
| 9,072,733 B2 | 7/2015 | Genkin et al. |
| 9,149,513 B2 | 10/2015 | Bartoov et al. |
| 9,198,957 B2 | 12/2015 | Ratner et al. |
| 9,205,133 B2 | 12/2015 | Dawson et al. |
| 9,248,166 B2 | 2/2016 | Gerkin et al. |
| 9,402,884 B2 | 8/2016 | Burns |
| 9,642,822 B2 | 5/2017 | Wagner |
| 9,770,492 B2 | 9/2017 | Genkin et al. |
| 9,845,461 B2 | 12/2017 | Genkin et al. |
| 9,867,871 B2 | 1/2018 | Jain |
| 2004/0138156 A1 | 7/2004 | Schneider et al. |
| 2009/0010966 A1 | 1/2009 | Davis et al. |
| 2013/0149749 A1 | 6/2013 | Holliger et al. |
| 2016/0251638 A1 | 9/2016 | Posada et al. |
| 2016/0376366 A1 | 12/2016 | Chang et al. |
| 2017/0196945 A1 | 7/2017 | Wagner et al. |
| 2020/0024585 A1 | 1/2020 | Fuchs et al. |

FOREIGN PATENT DOCUMENTS

| | | |
|---|---|---|
| WO | 2011053982 | 5/2011 |
| WO | 2011131772 | 10/2011 |
| WO | 2018015474 | 1/2018 |
| WO | 2018064681 | 4/2018 |
| WO | 2018134403 | 7/2018 |
| WO | 2018134419 | 7/2018 |
| WO | 2019036719 | 2/2019 |
| WO | 2021142456 | 7/2021 |

OTHER PUBLICATIONS

Andersen et al. 2014; Extending serum half-life of albumin by engineering neonatal Fe receptor (FcRn) binding. Journal of Biological Chemistry. 289(19): 13492-13502.

Napirei et al. 2009; Murine serum nucleases-contrasting effects of plasmin and heparin on the activities of DNase1 and DNase1-lie 3 (DNase113). FEBS Journal. 276: 1059-1073.

Shiokawa et al. 2003; Identification of two functional nuclear localization signals in DNase gamma and their roles in its apoptotic DNase activity. Biochem. J. 376: 377-381.

Berntsson et al., "Structural insight into DNA binding and oligomerization of the multifunctional Cox protein of bacteriophage P2", Nucleic Acids Research, vol. 42, No. 4, 2014, pp. 2725-2735.

Hakkim et al., "Impairment of neutrophil extracellular trap degradation is associated with lupus nephritis", PNAS, vol. 107, No. 21, 2010, pp. 9813-9818.

International Search Report and Written Opinion for International Application No. PCT/US2018/047084, dated Feb. 15, 2019, 23 pages.

Keyel, "Dnases in health and disease", Developmental Biology, vol. 429, 2017, pp. 1-11.

Kobayashi et al., "Synchronous Growth of Pichia Pastoris for a High-Rate Production of DNaseI at Microquantities", Department of Chemical Engineering. Toyko Institute of Technology. On-Line No. 833, 2004 pp. 1-6.

(Continued)

*Primary Examiner* — Suzanne M Noakes
(74) *Attorney, Agent, or Firm* — Morgan, Lewis & Bockius LLP

(57) ABSTRACT

The present disclosure provides a library of engineered DNASE proteins (including DNASE1, DNASE1-LIKE 1, DNASE1-LIKE 2, DNASE1-LIKE 3, DNASE2A, DNASE2B) that allows to select drug candidates for developing therapeutics for treating conditions characterized by neutrophil extracellular trap (NET) accumulation and/or release. In accordance with the invention, the selected DNase variant has improved properties, including properties amenable to clinical development, including manufacturing, toxicology, pharmacokinetic, and/or use in therapy.

30 Claims, 17 Drawing Sheets

Specification includes a Sequence Listing.

(56) References Cited

OTHER PUBLICATIONS

Perini et al., "Topical application of Acheflan on rat skin injury accelerates wound healing: a histopathological, immunohistochemical and biochemical study", BMC Complementary and Alternative Medicine, 2015, vol. 15, No. 203, pp. 1-8.
Piccolo et al., "Intrapleural Tissue Plasminogen Activator and Deoxyribonuclease for Pleural Infection; An Effective and Safe Alternative to Surgery", AnnalsATS, vol. 11, No. 9, 2014, pp. 1419-1425.
Sisirak et al., "Digestion of Chromatin in Apoptotic Cell Microparticles Prevents Autoimmunity", Cell vol. 166, 2016, pp. 88-101.
Wilber et al., "Deoxyribonuclease I-like III Is an Inducible Macrophage Barrier to Liposomal Transfection", MolecularTherapy, vol. 6, No. 1, 2002, pp. 35-42.
Jiménez-Alcázar et al., "Host DNases prevent vascular occlusion by neutrophil extracellular traps," Science 358, pp. 1202-1206 (2017).
Branden et al., "Prediction, Engineering, and -Design of Protein Structures", Introduction to Protein Structure, Garland Publishing Inc., New York, p. 247, 1991.
Seffernick, et al., "Melamine deaminase and Atrazine Chlorohydrolase: 98 Percent Identical but Functionally Different", Journal Of Bacteriology, 2001, pp. 2405-2410.
Shiokawa et al., "Characterization of Human DNase I Family Endonucleases and Activation of DNase γ during Apoptosis", Biochemistry 2001, 40, pp. 143-152.
Tang et al., "Identification of Dehalobacter Reductive Dehalogenases that Catalyse Dechlorination of Chloroform, 1,1,1-trichloroethane and 1,1-dichloroethane", Phil Trans R Soc B, 368, 20120318, 1-10, 2013.
Witkowski et al., "Conversion of a β-Ketoacyl Synthase to a Malonyl Decarboxylase by Replacement of the Active-Site Cysteine with Glutamine", Biochemistry 1999, 38, pp. 11643-11650.
Sadowski et al., "The sequence-structure relationship and protein function prediction", Current Opinion in Structural Biology 19:357-362, 2009.
Ensembl ID No. ENSG00000163687, release 102, Nov. 2020.
Rodriguez et al., Gen Bank accession No. 013609 Sep. 27, 2017.
Baron et al., Cloning and characterization of an actin-resistant DNase I-like endonuclease secreted by macrophages, Gene, 1998, vol. 215 pp. 291-301.
Saito et al., Apoptotic DNA endonuclease (DNase-γ) gene transfer induces cell death accompanying DNA fragmentation in human glioma cells, Journal of Neuro-Oncology, 2003, vol. 63, pp. 25-31.
Onuora, "DNASE1L3 prevents anti-DNA responses", Nature Rev. Rheumatol., 2016, vol. 12 No. 437, 1 page.
Wang et al., "Targeting the extracellular scavenger DNASE1L3 on SLE", J Xiangya Med, 2017, 3 pages.
Barnes et al. "Targeting potential drivers of COVID-19: Neutrophil extracellular traps", J. Exp. Med., 2020, vol. 217, pp. 1-7.
Al-Mayouf et al., Loss-of-function variant in DNASE1L3 causes a familial form of systemic lupus erythematosus, Nature Genetics, 2011, vol. 43, No. 12, pp. 1186-1188.
Özçakar et al., DNASE1L3 Mutations in Hypocomplementemic Urticarial Vasculitis Syndrome, Arthritis & Rheumatism, 2013, vol. 65, No. 8, pp. 2183-2189.
Carbonella et al., An autosomal recessive DNASE1L3-related autoimmune disease with unusual clinical presentation mimicking systemic lupus erythematosus, Lupus, 2017, vol. 26, pp. 768-772.
Bruschi et al., Neutrophil extracellular traps (NET) induced by different stimuli: A comparative proteomic analysis, PLOS ONE, 2019, pp. 1-18.
Landhuis, "Spider-Man' Immune Response May Promote Severe COVID-19", Sci. Am., 2020, pp. 1-7.
Reizis, "Project 3: The role of DNASE1L3 and its DNA substrate in lupus", National Institute of Health (NIH), 2015, 5 pages.
Boettcher et al. "Therapeutic targeting of extracellular DNA improves the outcome of intestinal ischemic reperfusion injury in neonatal rats," Scientific Reports, Nov. 13, 2017 (Nov. 13, 2017), vol. 7, No. 15377, pp. 1-10.
De Meyer et al. "Extracellular Chromatin Is an Important Mediator of Ischemic Stroke in Mice," Arteriosclerosis, Thrombosis, and Vascular Biology, May 24, 2012 (May 24, 2012), vol. 32, No. 8, pp. 1884-1891.
International Search Report and Written Opinion for International Application No. PCT/US2020/016490, dated Jun. 23, 2020, 12 pages.

| D1L1_NP_006721.1 | MHYPTAL--LFLILANGAQAFRICAFNAQRLTLAKVAREQVMDTLVRILA |
| --- | --- |
| D1L3_NP_004935.1 | MSRELAPLLLLLSIHSALAMRICSFNVRSFGESKQEDKNAMDVIVKVIK |

| D1L1_NP_006721.1 | RCDIMVLQEVVDSSGSAIPLLRELNRFDGSG-PYSTLSSPQLGRSTYME |
| --- | --- |
| D1L3_NP_004935.1 | RCDIILVMEIKDSNNRICPILMEKLNRNSRRGITYNYVISSRLGRNTYKE |

| D1L1_NP_006721.1 | TYVYFYRSHKTQVLSSYVYND----EDDVFAREPFVAQFSLPSNVLPSLV |
| --- | --- |
| D1L3_NP_004935.1 | QYAFLYKEKLVSVKRSYHYHDYQDGDADVFSREPFVVWFQSPHTAVKDFV |

| D1L1_NP_006721.1 | LVPLHTTPKAVEKELNALYDVFLEVSQHWQSKDVILLGDFNADCASLTKK |
| --- | --- |
| D1L3_NP_004935.1 | IIPLHTTPETSVKEIDELVEVYTQVKHRWKAENFIFMGDFNAGCSYVPKK |

| D1L1_NP_006721.1 | RLDKLELRTEPGFHWVIADGEDTTVRASTHCTYDRVVLHGERCRSLL--H |
| --- | --- |
| D1L3_NP_004935.1 | AWKNIRLRTDPRFVWLIGDQEDTTVKKSTNCAYDRIVLRGQEIVSSVVPK |

| D1L1_NP_006721.1 | TAAAFDFPTSFQLTEEEALNISDHYPVEVELKLSQAHSVQPLSLTVLLLL |
| --- | --- |
| D1L3_NP_004935.1 | SNSVFDFQKAYKLTEEEALDVSDHFPVEFKLQSSRAFTNSKKSVTLRKKT |

| D1L1_NP_006721.1 | SLLSPQLCPAA |
| --- | --- |
| D1L3_NP_004935.1 | KSKRS------ |

FIG. 4
BUILDING BLOCK-ENGINEERING OF HOMOLOGOUS PROTEINS
I. AMINO ACID SEQUENCE ALIGNMENT OF HOMOLOGOUS ENZYMES
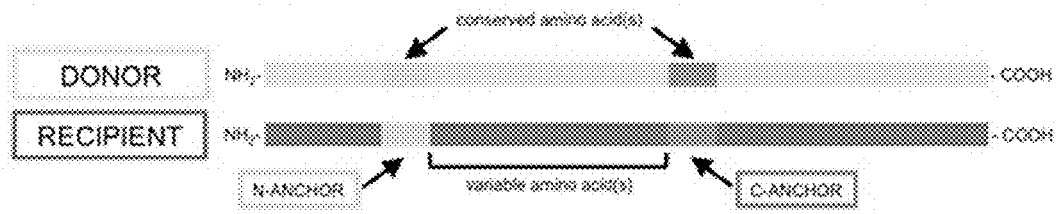
II. EXCISION OF CDNA CODING FOR VARIABLE AMINO ACIDS IN DONOR ENZYME
III. DELETION OF CDNA CODING FOR VARIABLE AMINO ACIDS IN RECIPIENT ENZYME
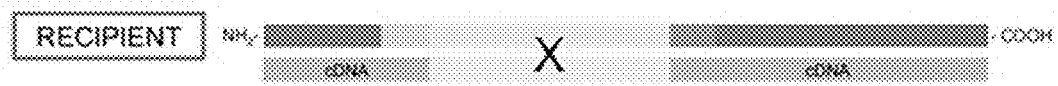
IV. TRANSFER OF CDNA FROM DONOR TO RECIPIENT ENZYME
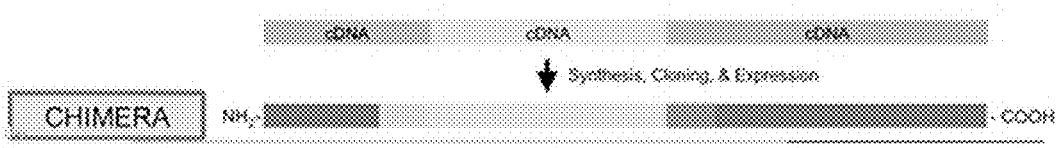

FIG. 5

| | 1 | 10 | 20 | 30 | 40 | 50 | 60 | 70 |
|---|---|---|---|---|---|---|---|---|
| MOUSE (P49183) | MRYT-GLMGTLLLTL- | VNLLQLAGTLRI | AAFNIRTFGETKMSNATLSVYF | VKILSRYDIAVIQEVRDSHLVAVGKLLDEL |
| RAT (P21704) | MRYT-GLMGILLTL- | VNLLQLAATLRI | AAFNIRTFGDTKMSNATLSSYI | VKILSRYDIAVVQEVRDTHLVAVGKLLDEL |
| CHIMPANZEE (H2QAH1) | MRSM-KLLGALLAL- | AALLQGAVSLKI | AAFNIQTFGETKMSNATLVSY | VQILSRYDIALVQEVRDSHLTAVGKLLDNL |
| HUMAN (P24855) | MRGM-KLLGALLAL- | AALLQGAVSLKI | AAFNIQTFGETKMSNATLVSYI | VQILSRYDIALVQEVRDSHLTAVGKLLDNL |
| Sequence Ruler | | | | | | | | |

| | 1 | 10 | 20 | 30 | 40 | 50 | 60 | 70 |
|---|---|---|---|---|---|---|---|---|
| MOUSE (O55070) | MSLHPASPRLASLLFFLALHDTLALRLCSFNVRSFGASKKENHEAMDIIVKIIKRCDLILLMEIKDSNNICPMLEMEKL |
| RAT (O89107) | MSLYPASPYIASLLFILALHGALSLRLCSFNVRSFGESKKENHNAMDIIVKIIKRCDLILLMEIKDSNNICPMLEMEKL |
| CHIMPANZEE (H2QMJ7) | -MSRELTPLLLLLLLSIHSTLALRICSFNVRSFGESKQEDQNAMDVIVKIKRCDIILVMEIKDSNNRICPILMEKL |
| HUMAN (Q13609) | -MSRELAPLLLLLLLSIHSALAMRICSFNVRSFGESKQEDKNAMDVIVKVIKRCDIILVMEIKDSNNRICPILMEKL |
| Sequence Ruler | | | | | | | | |

| | 80 | 90 | 100 | 110 | 120 | 130 | 140 | 150 |
|---|---|---|---|---|---|---|---|---|
| MOUSE (P49183) | NRDK--PDTYRYVVSEPLGRKSYKEQYLFVYRPDQVSILDSYQYDDGCEPCGNDTFSREPAIVKFFSPYTEVQEFAIVPL |
| RAT (P21704) | NRDI--PDNYRYIISEPLGRKSYKEQYLFVYRPSQVSVLDSYHYDDGCEPCGNDTFSREPAIVKFFSPYTEVREFAIVPL |
| CHIMPANZEE (H2QAH1) | NQDA--PDTYHYVVSEPLGRNSYKERYLFVYRPDQVSAVDSYYYDDGCEPCGNDTFNREPAIVRFFSRFTEVREFAIVPL |
| HUMAN (P24855) | NQDA--PDTYHYVVSEPLGRNSYKERYLFVYRPDQVSAVDSYYYDDGCEPCGNDTFNREPAIVRFFSRFTEVREFAIVPL |
| Sequence Ruler | | | | | | | | |

| | 80 | 90 | 100 | 110 | 120 | 130 | 140 | 150 |
|---|---|---|---|---|---|---|---|---|
| MOUSE (O55070) | NGNSRRSTTTYNYVISSRLGRNTYKEQYAFVYKEKLVSVKTKVHYHDYQ-DGDTDVFSREPFVVWFHSPFTAVKDFVYVPL |
| RAT (O89107) | NGNSRRSTTTYNYVISSRLGRNTYKEQYAFLYKEKLVSYKAKYLYHDYQ-DGDTDVFSREPFVVWFQAPFTAAKDFVYVPL |
| CHIMPANZEE (H2QMJ7) | NRNSRRGITYNYVISSRLGRNTYKEQYAFLYKEKLVSVKRSYHYHDYQ-DGDADVFSREPFVVWFQSPHTAVKDFVIPL |
| HUMAN (Q13609) | NRNSRRGITYNYVISSRLGRNTYKEQYAFLYKEKLVSVKRSYHYHDYQ-DGDADVFSREPFVVWFQSPHTAVKDFVIPL |
| Sequence Ruler | | | | | | | | |

Signal Peptide | Conserved AA = Anchors | Variable AA = Building Blocks

DNase1 | DNase1L3

Example of Building Block Engineering: human DNase1 (D1) variants with Building Blocks from human DNase1L3 (D1L3)

| BB # | D1 N-Anchor Conserved AA in D1 | D1 C-Anchors Conserved AA in D1 | D1 Building Blocks Variable AA in D1 | D1L3 Building Blocks Variable AA in D1L3 | Building Block Mutations of D1 variants | BB Cluster |
|---|---|---|---|---|---|---|
| 0 | NA | NA | 1-22 (MRGMKLL GALLALAALLQGAVS) | 1-20 (MSRELAPLLLLLSHSALA) | M1_S22delinsMSRELAPLLL LLSHSALA | BB₀ |
| 1 | Signal peptide | F28/N29 | 23-27 (LKIAA) | 21-35 (MRCS) | L23_A27delinsMRICS | BB₁₋₃ |
| 2 | F28/N29 | F33/G34 | 30-32 (IQT) | 28-30 (VRS) | I30_T32delinsVRS | |
| 3 | F33/G34 | K37 | 35-36 (ET) | 33-34 (ES) | E35_T36delinsES | |
| 4 | K37 | V46 | 38-47 (MSNAT,VSVI) | 38-45 (QEDKNAMDVI) | M38_I47delinsQEDKNAMDVI | BB₄ |
| 5 | V46 | R53 | 49-52 (QILS) | 47-50 (KVIK) | Q49_S52delinsKVIK | BB₅₋₇ |
| 6 | R53 | D55 | 54 (Y) | 52 (O) | Y54C | |
| 7 | D55 | E61 | 56-60 (IALVQ) | 54-58 (ILVM) | I56_Q60delinsILVM | |
| 8 | E61 | D64 | 62-63 (VR) | 60-61 (IK) | V62_R63delinsIK | BB₈₋₁₀ |
| 9 | D64 | L73 | 65-72 (SHLTAVGK) | 63-70 (SNNRICPI) | S65_K72delinsSNNRICPI | |
| 10 | L73 | L77/N78 | 74-76 (LDN) | 72-74 (MEK) | L74_N76delinsMEK | |
| 11 | | | | | | |
| 12 | | | | | | |
| 13 | | | | | | |
| 14 | | | | | | |
| 15 | L93/K95/R95 | Y98/K99/E100 | 96-97 (NS) | 96-97 (NT) | N96_S97delinsNT | BB₁₅₋₁₆ |
| 16 | Y98/K99/E100 | Y102 | 101 (R) | 101 (Q) | R101Q | |
| 17 | Y102 | F104 | 103 (L) | 103 (A) | L103A | |
| 18 | F104 | Y106 | 105 (V) | 105 (L) | V105L | |
| 19 | Y106 | Y111/S112 | 107-110 (RPDQ) | 107-110 (KEKL) | R107_Q110delinsKEKL | BB₁₉₋₂₂ |
| 20 | Y111/S112 | Y117 | 113-116 (AVDS) | 113-116 (VKRS) | A113_S116delinsVKRS | |
| 21 | Y117 | Y119 | 118 (Y) | 118 (H) | Y118H | |
| 22 | Y119 | D121 | 120 (D) | 120 (H) | D120H | |
| 23 | D121 | Q129 | 122-128 (QCEPCSN) | 122-127 (YQDGDA) | Q122_N128delinsYQDGDA | BB₂₃₋₂₅ |
| 24 | Q129 | F131 | 130 (T) | 129 (V) | T130S | |
| 25 | F131 | R133/E134/P135 | 132 (N) | 131 (S) | N132S | |
| 26 | | | | | | |
| 27 | V138 | F140 | 139 (R) | 138 (W) | R139W | BB₂₇ |
| 28 | F140 | T143 | 141-144 (FSRF) | 140-143 (QSPH) | F141_F144delinsQSPH | BB₂₈₋₃₀ |
| 29 | T143 | F150 | 146-149 (EVRE) | 145-148 (AVKD) | E146_E149delinsAVKD | |
| 30 | F150 | I152 | 151 (A) | 150 (V) | A151V | |
| 31 | I152 | P154/L155/H156 | 153 (V) | 152 (I) | V153I | |
| 32 | P154/L155/H156 | P159 | 157-158 (AA) | 156-157 (TT) | A157_A158delinsTT | BB₃₂₋₃₃ |
| 33 | P159 | V163 | 160-162 (GDA) | 159-161 (ETS) | G160_A162delinsETS | |
| 34 | V163 | E165/I166/D167 | 164 (A) | 163 (K) | A164K | |

| BB # | D1L3 N-Anchor Conserved AA in D1L3 | D1L3 C-Anchor Conserved AA in D1L3 | D1L3 Building Blocks Variable AA in D1L3 | D1 Building Blocks Variable AA in D1 | Building Block Mutations of D1L3 variants | BB Cluster |
|---|---|---|---|---|---|---|
| 35 | E164/165/D166 | L168 | 167 (E) | 167 (A) | E167A | BB-j |
| 36 | | Y171/Y172 | 169-170 (YE) | 170-171 (YO) | V

FIG. 7

BUILDING BLOCK CLUSTER-ENGINEERING

I. AMINO ACID SEQUENCE ALIGNMENT OF HOMOLOGOUS ENZYMES

II. TANSFER OF BUILDING BLOCK CLUSTERS

III. TANSFER OF INDIVIDUAL BUILDING BLOCKS (OPTIONAL)

IV. TANSFER OF INDIVIDUAL AMINO ACID RESIDUES (OPTIONAL)

FIG. 10

| Amino Acid Position | 290 · · · · · 300 · · · · · | # Of Deleted Amino Acids |
|---|---|---|
| Wild-Type | K L Q S S R A F T N S K K S V T L R K K T K S K R S | 0 |
| S305del | K L Q S S R A F T N S K K S V T L R K K T K S K R - | 1 |
| K303_S305del | K L Q S S R A F T N S K K S V T L R K K T K S - - - | 3 |
| V294_S305del | K L Q S S R A F T N S K K S - - - - - - - - - - - - | 12 |
| K291_S305del | K L Q S S R A F T N S - - - - - - - - - - - - - - - | 15 |
| R285_S305del | K L Q S S - - - - - - - - - - - - - - - - - - - - - | 21 |
| S283_S305del | K L Q - - - - - - - - - - - - - - - - - - - - - - - | 23 |

Uniprot: Q13609

FIG. 13

| Input Nucleic Acid | C-Terminal Deletion (# Of AA) | C-Terminal AA Sequence (Deleted AA) | SEQ ID NO: |
|---|---|---|---|
| Wild-Type DNASE1L3 | 1 | -SSRAFTNSKKSVTLRKKTKSKR (S) | 22 |
| | 8 | -SSRAFTNSKKSVTLR (KKTKSKRS) | 51 |
| | 9 | -SSRAFTNSKKSVTL (RKKTKSKRS) | 52 |
| | 13 | -SSRAFTNSKK (SVTLRKKTKSKRS) | 53 |
| | 14 | -SSRAFTNSK (KSVTLRKKTKSKRS) | 54 |
| | 15 | -SSRAFTNS (KKSVTLRKKTKSKRS) | 25 |

ENGINEERED HUMAN EXTRACELLULAR DNASE ENZYMES

PRIORITY

This Application is a continuation-in-part of U.S. application Ser. No. 17/427,974, filed Aug. 3, 2021, which is a national stage entry of PCT/US2020/016490, filed Feb. 4, 2020, and which claims the benefit of US Provisional Application No. 62/800,790, filed Feb. 4, 2019, each of which is hereby incorporated by reference in its entirety.

BACKGROUND

Inflammation is an essential host response to control invading microbes and heal damaged tissues. Uncontrolled and persistent inflammation causes tissue injury in a plethora of inflammatory disorders. Neutrophils are the predominant leukocytes in acute inflammation. During infections neutrophils generate neutrophil extracellular traps (NETs), lattices of DNA-filaments decorated with toxic histones and enzymes that immobilize and neutralize bacteria. However, excessive NET formation may harm host cells due to their cytotoxic, proinflammatory, and prothrombotic activity.

DNASE1 (D1) forms along with DNASE1-LIKE 1 (D1L1), DNASE1-LIKE 2 (D1L2) and DNASE1-LIKE 3 (D1L3), the DNASE1-protein family, a group of homologous secreted DNase enzymes. DNASE2A and DNASE2B form an additional group of homologous extracellular DNase enzymes. DNASE1- and DNASE2-protein family members are evolutionary conserved and expressed in various species, including humans. Recombinant human DNASE1- and DNASE2-protein family members provide drug candidates for NET-associated diseases, but the physical, enzymatic, toxicological, and pharmacokinetic properties of these enzymes are not ideal for clinical applications. Thus, there is a need for engineered DNase enzymes for use in therapy that have improved properties, including properties amenable to clinical development, including manufacturing, toxicology, pharmacokinetic (including protease resistance), and/or use in therapy.

SUMMARY

The present invention provides candidates of engineered human extracellular DNase proteins (e.g., variants of DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), DNASE2A (D2A), and DNASE2B (D2B)) that are useful for treating conditions characterized by extracellular DNA, extracellular chromatin, and/or neutrophil extracellular trap (NET) accumulation and/or release. In accordance with aspects of the invention, DNase variants described herein are more amenable to clinical development, including manufacturing, toxicology, pharmacokinetic, and/or use in therapy.

In some aspects, the invention provides a method for making a DNase therapeutic composition for treating an extracellular chromatin or NET-associated disorder. The method comprises evaluating a plurality of extracellular DNase variants for one or more characteristics, including enzymatic activity, nucleic acid substrate preference, potential for recombinant expression in prokaryotic or eukaryotic host cells, immunogenic potential in humans and animals, and pharmacodynamics in animal models. An extracellular DNase variant is selected with the desired enzymatic, physical, and pharmacodynamics profile, and is formulated for administration to a patient, e.g., for either systemic or local administration.

In various embodiments, the DNase variant evaluated and selected for use in therapy in accordance with embodiments of the invention comprise an amino acid sequence that is at least 80% identical to the enzyme defined by any one of SEQ ID NOS: 1 to 7, with one or more building block substitutions or C-terminal modifications as described herein. In some embodiments, the DNase variant comprises an N-terminal or C-terminal fusion to a half-life extending moiety, such as albumin, transferrin, an Fc, or elastin-like protein.

In various embodiments, a selected DNase variant is formulated with a pharmaceutically acceptable carrier for systemic, local, or topical administration.

In other aspects, the invention provides a method for treating a subject in need of extracellular DNA degradation, extracellular chromatin degradation, extracellular trap (ET) degradation and/or neutrophil extracellular trap (NET) degradation. The method comprises administering a therapeutically effective amount of the extracellular DNase variant in accordance with the disclosure.

Other aspects and embodiments of the disclosure will be apparent from the following detailed description.

BRIEF DESCRIPTION OF THE DRAWINGS

FIG. 1 illustrates the approach for engineering DNase variants for therapeutic applications using Building Block Protein Engineering.

FIG. 2 shows an alignment of DNASE1-LIKE 3 Isoform 1 proteins from different species. Amino acids that are non-conserved in human DNASE1 are highlighted. Such non-conserved amino acids can be transferred to human DNASE1-LIKE 3 Isoform 1 for developing a variant for therapy. The DNASE1-LIKE 3 Isoform 1 proteins used for this analysis were Human DNASE1-LIKE 3 Isoform 1, UniProtKB: Q13609; NCBI Reference Sequence: NP_004935.1 (SEQ ID NO: 4); *Pan troglodytes* (Chimpanzee) DNase1L3 UniProtKB: A0A2I13RHL6 (and H2QMU7) (SEQ ID NO: 33); *Papio anubis* (Olive baboon) DNASE1L3, UniProtKB: A0A2I3NFJ3 (SEQ ID NO: 34); Mouse Dnase1l3, UniProtKB: O55070 (SEQ ID NO: 31); Rat Dnase1L3, UniProtKB: O89107 (SEQ ID NO: 32); *Oryctolagus cuniculus* (Rabbit) DNase1L3, UniProtKB: G1SE62 (SEQ ID NO: 35); *Canis lupus familiaris* (Dog) DNase1L3, UniProtKB: F1P9C1 (SEQ ID NO: 36); *Sus scrofa* (Pig) DNase1L3, UniProtKB: A0A287B132 (SEQ ID NO: 37); *Cavia porcellus* (Guinea pig) DNase1L3, UniProtKB: A0A286XK50 (SEQ ID NO: 38); *Bos taurus* (Cow) DNase1L3, UniProtKB: F1MGQ1 (SEQ ID NO: 39); and *Loxodonta africana* (African elephant) DNase1L3, UniProtKB: G3SXX1 (SEQ ID NO: 40)

FIG. 3 shows an alignment of two members of the human DNASE1 proteins family, DNASE1-LIKE 1 and DNASE1-LIKE 3 Isoform 1. Amino acids that are conserved among human DNASE1-LIKE 1 (NCBI Reference Sequence: NP_006721.1; SEQ ID NO: 2) and DNASE1-LIKE 3 Isoform 1 (NCBI Reference Sequence: NP_004935.1; SEQ ID NO: 4) are highlighted. The non-conserved amino acids can be transferred from human DNASE1-LIKE 1 to DNASE1-LIKE 3 Isoform 1 or vice versa for developing variants for therapy, respectively.

FIG. 4 shows the concept of building block engineering of homologous proteins. The technology transfers single or multiple variable amino acids, which are flanked by conserved single or multiple variable amino acids, between a donor and recipient protein.

FIG. 5 shows an amino acid sequence alignment of DNase1 and DNase1L3 of mouse (SEQ ID NOs: 31 and 32), rat (SEQ ID NOs: 33 and 34), chimpanzee (SEQ ID NOs: 35 and 36), and human (SEQ ID NOs: 1 and 4). The N-terminal signal peptide, corresponding to N-terminal 22 amino acids of DNase1 is shown in light grey and conserved amino acids are highlighted in a darker shade of grey. Variable amino acids are not highlighted and serve as Building Blocks that can be transferred from DNase1 to DNase1L3 and vice versa. Abbreviations: AA, amino acid.

FIGS. 6A-FIG. 6B show lists of Building Blocks in human DNase1 (D1) and human DNase1L3 (D1L3). FIG. 6A shows amino acids that are conserved in D1 and D1L3, which serve as N- and C-anchors, respectively. Building blocks are variable amino acids in D1 and D1L3. Mutations that transfer Building Blocks from D1L3 to D1 are shown. FIG. 6B shows N- and C-anchors in D1L3. Mutations that transfer Building Blocks from D1 to D1L3 are listed. AA: amino acid.

FIG. 7 shows an application of the building block engineering of homologous proteins. The application uses as an initial screening step, the transfer of clusters of building blocks between a homologous donor and recipient protein. Additional optional steps are the transfer of individual building blocks, followed by the transfer of individual amino acids. In a final step (not shown), multiple amino acids, building blocks, and building block clusters may be combined to degenerate a chimeric enzyme.

FIG. 8 shows characterization of DNase1 variants (Dlv) featuring building blocks from DNase1L3 (D1L3). Zymography showed dsDNA degrading activity as dark circles. The dsDNA degrading activity correlates with the diameter. Samples without activity show the loading well as small black spot (e.g. Ctrl). Agarose gel electrophoresis (AGE) of DNA isolated from digested chromatin shows a shift from high-molecular weight DNA to lower or low-molecular weight DNA that correlates with chromatin degrading activity. Building block substitutions that cause an increase in chromatin degrading activity are highlighted in dark shade. Samples without such effect are shown in light shade. A DNase1 variant featuring the combination of building blocks 11, 12-14, 26, 41-48, and 49 shows similar chromatin degrading activity than wild-type DNase1L3.

FIG. 9 illustrates that the mutation Q282_S305delinsK in D1L3 Isoform 1 increases the activity to degrade high-molecular weight chromatin of DNASE1L3.

FIG. 10 shows the location of NLS2 sequence superimposed with a sequence alignment of C-termini of the S305del, K303_S305del, V294_S305del, K291_S305del, R285_S305del, and S283_S305de1 deletion mutants, which lack 1, 3, 12, 15, 21, and 23 C-terminal amino acids, respectively.

FIG. 11 shows a western blot of wild type D1L3 and BD-deleted D1L3 expressed in furin-overexpressing CHO cells. CHO cells without overexpression of furin were included as control. Data suggest that cleavage of the C-terminal tail or a portion thereof could act as an activation signal for D1L3.

FIG. 12A shows the expression vectors containing WT-DNASE1L3 or BDD-DNASE1L3 fused via a linker to Fc fragment, and used for expression in CHO cells. FIG. 12B shows SDS-PAGE protein gels of Fc fusion proteins purified via protein A/G from supernatants of CHO cells expressing WT-DNASE1L3 or BDD-DNASE1L3 fused via a linker to Fc fragment. Both gels show bands of approximately 65-70 kDa, which reflects the molecular weight of the full-length proteins. An additional lower molecular weight (between 29-44 kDa) is detected, when CHO cells express the WT-DNASE1L3 construct.

FIG. 13 shows a table of C-terminal amino acid sequences of DNASE1L3 variants that are secreted by cells expressing WT DNASE1L3 cDNA. The C-termini were specifically truncated at the three clusters of paired basic amino acids, resulting in deletions of 1, 8, 9, 13, 14 and 15 amino acids of the BD.

DETAILED DESCRIPTION

As used herein, the term "neutrophil extracellular trap" or "NET" refers to any extracellular trap ("ET") comprising extracellular DNA formed by cells such as, but not limited to, neutrophils, monocytes, macrophages, basophils, eosinophils, mast cells, cancer cells, injured cells (e.g., injured endothelial cells), and the like. Unless the context indicates otherwise, the terms NET and ET are used interchangeably herein.

The similarity of nucleotide and amino acid sequences, i.e. the percentage of sequence identity, can be determined via sequence alignments as known in the art. Such alignments can be carried out with several art-known algorithms, such as with the mathematical algorithm of Karlin and Altschul (Karlin & Altschul (1993) *Proc. Natl. Acad. Sci. USA* 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80). Exemplary algorithms are incorporated into the BLASTN and BLASTP programs of Altschul et al (1990) *J. Mol. Biol.* 215: 403-410. When utilizing BLAST programs, the default parameters of the respective programs are used.

In various aspects, the invention provides a protein engineering technology that is based on a transfer of a single amino acid or multiple-adjacent amino acids, termed "building block", between two members of a protein family, such as DNase1 or DNase 2 protein family members to generate enzymatically active variants. A "building block" is defined by amino acids that are variable between two or more members of the DNase protein family. These variable amino acids are flanked by amino acids that are conserved between two or more members of the DNase-protein family ("anchors"). The variable single amino acid or multiple contiguous amino acids ("building blocks") are exchanged between members of the DNase-protein family by implanting them between conserved single amino acid or multiple contiguous amino acids ("anchors").

This approach is referred to herein as "building-block protein engineering." Where three or more amino acids are transferred in a building block, up to ⅓ of the amino acids transferred may be further substituted. For example, where three to six amino acids are transferred as a building block, one or up to two resides may be further substituted. In some embodiments, four or more amino acids are transferred as a building block substitution, and up to 25% of the transferred amino acids are further substituted, e.g., with conservative or non-conservative amino acid modifications. For example, where four, eight, or twelve amino acids are transferred, one, two, or three amino acids (respectively) may be further substituted in the building block substitution.

The present invention provides candidates of engineered human extracellular DNase proteins (e.g., variants of DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), DNASE2A (D2A), and DNASE2B (D2B)) that are useful for treating conditions characterized by extracellular DNA, extracellular chromatin, and/or neutrophil extracellular trap (NET) accumulation and/or release. In accordance with aspects of the invention, DNase variants described herein are more amenable to clinical development, including manufacturing, toxicology, pharmacokinetic, and/or use in therapy.

Figure 8:
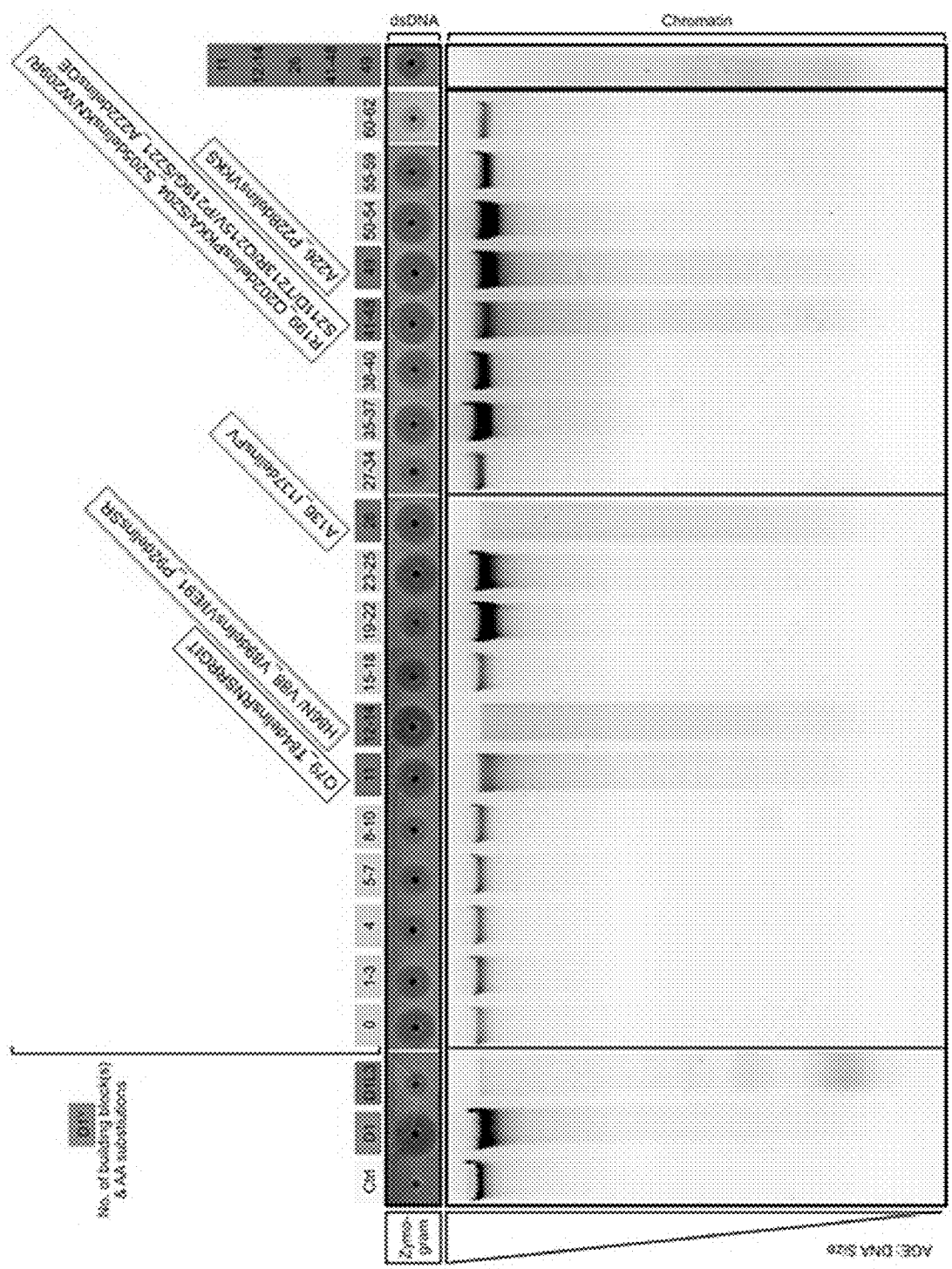
Figure 9:
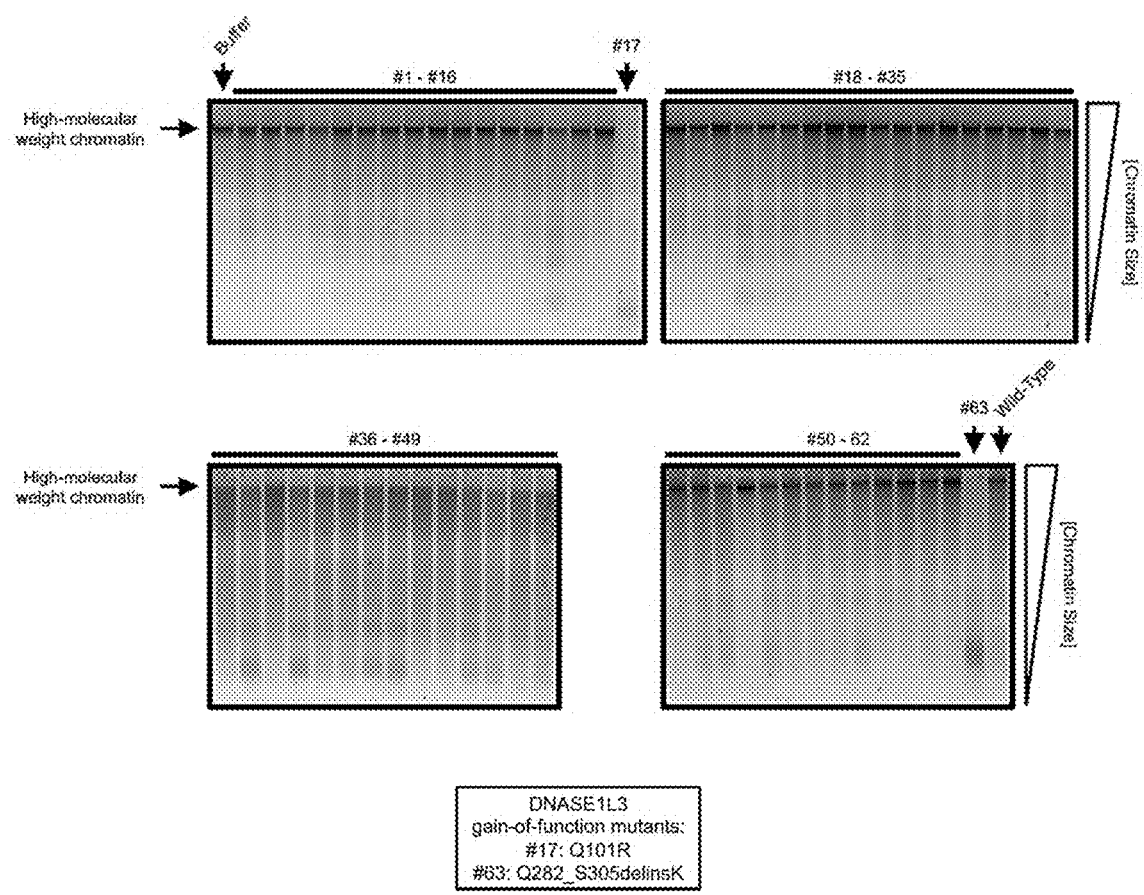
Figure 11:
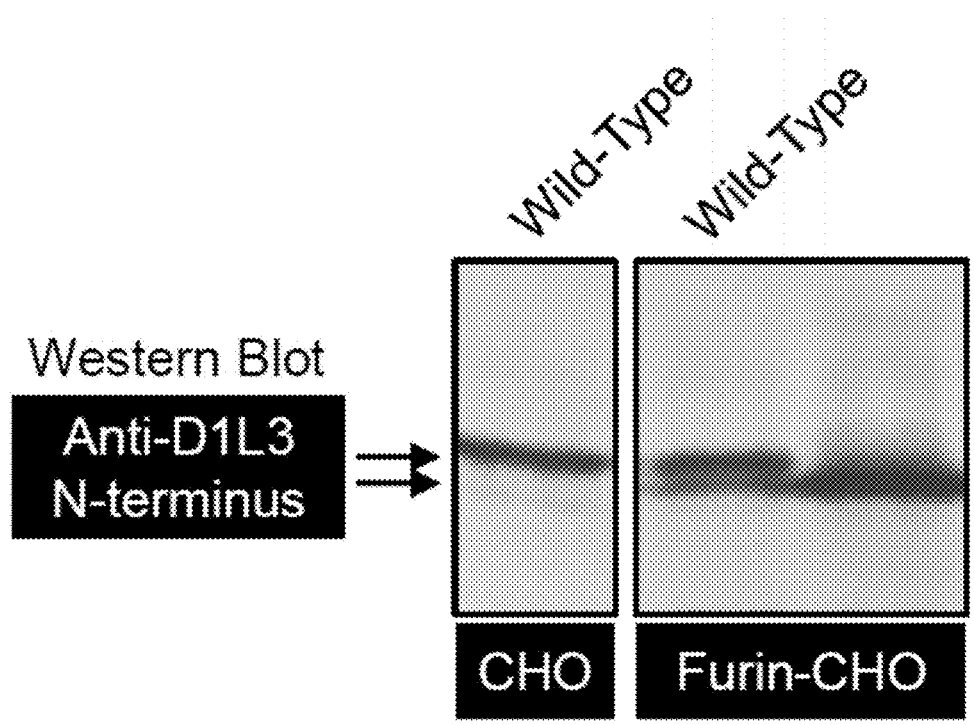
Figure 12A:
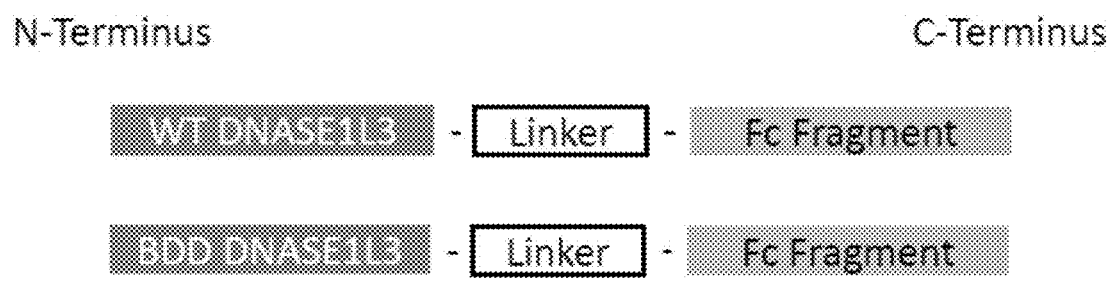
Figure 12B:
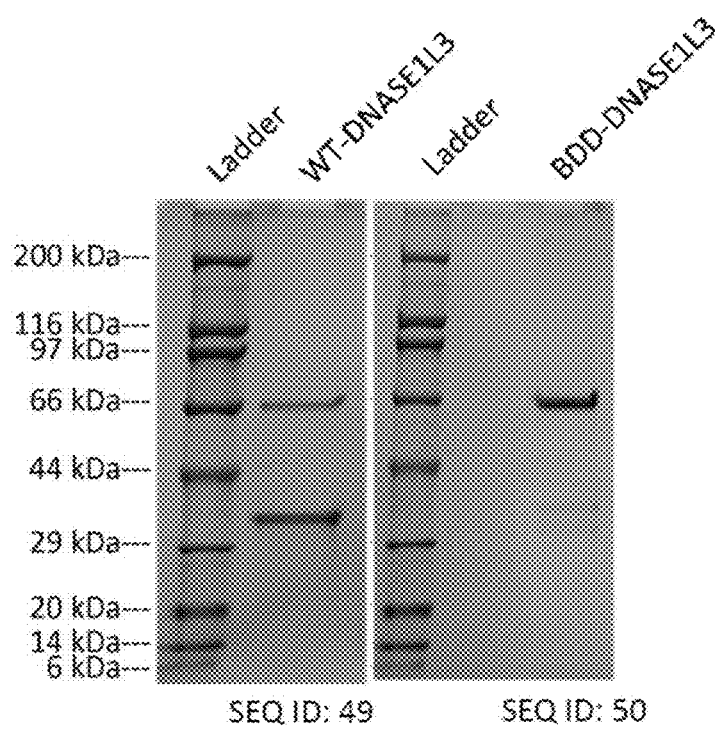

In some aspects, the invention provides a method for making a DNase therapeutic composition for treating a NET-associated disorder or disorder characterized by pathological accumulation of extracellular chromatin. The method comprises evaluating a plurality of extracellular DNase variants for one or more characteristics, including enzymatic activity, nucleic acid substrate preference, suitability for recombinant expression in prokaryotic or eukaryotic host cells, immunogenic potential in humans and animals, and pharmacodynamics in animal models. An extracellular DNase variant is selected with the desired enzymatic, physical, and pharmacodynamics profile, and is formulated for administration to a patient, e.g., for either systemic or local administration.

In various embodiments, at least 5 or at least 10, or at least 20, or at least 50 extracellular DNase variants are evaluated, with the variants selected from one or more of D1 variants, D1L1 variants, D1L2 variants, D1L3 isoform 1 variant, D1L3 isoform 2 variants, D2A variants, and D2B variants as described herein. As described herein, one or more (or all) variants may comprise at least one building block substitution, half-life extension moiety, and/or other mutation or variation described herein. In some embodiments, the method evaluates one or more D1L1 variants described herein. In some embodiments, the method evaluates one or more D1L2 variants described herein. In some embodiments, the method evaluates one or more D1L3 variants described herein. In some embodiments, the method evaluates one or more D1L3-2 variants described herein. In some embodiments, the method evaluates one or more D2A variants described herein. In some embodiments, the method evaluates one or more D2B variants described herein. In some embodiments, the method evaluates one or more D1 variants described herein.

In various embodiments, the invention provides a recombinant variant of human extracellular DNase enzymes comprising one or more amino acid alterations resulting in an altered pH and temperature optimum, requirement for divalent cations for enzymatic activity, mechanisms of enzymatic inhibition (e.g. salt, divalent cations, actin, heparin, proteases), substrate affinity and specificity (e.g. single-stranded DNA, double-stranded DNA, chromatin, NETs, plasmid DNA, mitochondrial DNA), localization upon secretion (e.g. membrane-bound, extracellular matrix), localization signals (e.g. nuclear localization signal, membrane anchor), glycosylation sites, disulfide-bonds and unpaired cysteines, compatibility with GMP-compliant in vitro expression systems (e.g. bacteria. yeast, mammalian cells), compatibility with carriers (e.g. PEGylation, Fc fragment, albumin), compatibility with GMP-compliant purification methods (e.g. anion exchange resins, cation exchange resins), toxicological profile, tissue penetration, pharmacokinetics and pharmacodynamics. In accordance with this disclosure, candidate DNase variants can be selected with desired properties for therapy.

In various embodiments, DNase variants will comprise at least one building block substitution, using a Building Block Protein Engineering technology. The Building Block Engineering approach is described in PCT/US2018/047084 (corresponding to WO 2019/036719 and U.S. Pat. No. 10,696, 956), which are hereby incorporated by reference in its entirety. This approach involves providing a protein-protein alignment of donor and recipient DNase enzymes, and identifying variable amino acid sequences for transfer ("building block"). The variable amino acid(s) are flanked by one or more conserved amino acids in the donor and recipient DNase enzymes (upstream and downstream of the building block). These building blocks can be swapped between recipient and donor proteins, to produce a chimeric enzyme. The donor and recipient DNase enzymes can be selected from members of the DNASE1- or DNASE2-protein family. Accordingly, for example, human DNASE1 and human DNASE1L1 can be selected as donor and recipient DNase proteins, respectively. Alternatively, donor and recipient DNase can be selected from a DNase proteins that are expressed in different species. Accordingly, for example, bovine and human DNASE1 can be selected as donor and recipient DNase proteins, respectively.

As used herein, when referring to sequence identity with wild-type extracellular DNase enzymes, and unless stated otherwise, sequences refer to mature enzymes lacking the signal peptide. Further, unless stated otherwise, amino acid positions are numbered with respect to the full translated extracellular DNase sequence, including signal peptide, for clarity. Accordingly, for example, reference to sequence identity to the enzyme of SEQ ID NO: 1 (human D1) refers to a percent identity with the mature enzyme having L23 at the N-terminus, reference to sequence identity to the enzyme of SEQ ID NO: 2 (human D1L1) refers to a percent identity with the mature enzyme having F19 at the N-terminus, reference to sequence identity to the enzyme of SEQ ID NO: 3 (human D1L2) refers to a percent identity with the mature enzyme having L22 at the N-terminus, reference to sequence identity to the enzyme of SEQ ID NO: 4 (human D1L3) refers to a percent identity with the mature enzyme having M21 at the N-terminus, reference to sequence identity to the enzyme of SEQ ID NO: 5 (human D1L3-2) refers to a percent identity with the mature enzyme having M21 at the N-terminus, reference to sequence identity to the enzyme of SEQ ID NO: 6 (human D2A) refers to a percent identity with the mature enzyme having C19 at the N-terminus, and reference to sequence identity to the enzyme of SEQ ID NO: 7 (human D2B) refers to a percent identity with the mature enzyme having A28 at the N-terminus.

The term "delins" refers to a deletion between two indicated amino acids, with an insertion of an amino acid or sequence of amino acids at the site of the deletion. For example, the notation E91_P92delinsSR means that the amino acids from E91 to P92 are deleted and the amino acids SR are inserted at the site of the deletion (e.g., the resulting amino acid sequence will have S91 and R92).

The term "ins" refers to an insertion of amino acids between two indicated amino acids. For example, the notation E91_P92insSR means that the amino acids SR are inserted between E91 and P92, resulting in the sequence E91, S92, R93, and P94.

The term "del" refers to a deletion of one amino acid or two and more amino acids between two indicated amino acids. For example, the notation E91del means that the amino acid E91 is deleted, whereas the notion E91_P93del means that the three amino acids from E91 and P93 are deleted.

The engineered variants of human extracellular DNase enzymes may comprise one or more additional amino acid substitutions, additions (insertions), deletions, or truncations in the amino acid sequence of the human enzyme (SEQ ID NO: 1 to 7). Amino acid substitutions may include conservative and/or non-conservative substitutions. For example, "conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe. "Conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. As used herein, "non-conservative substitutions" are defined as exchanges of an amino acid by another amino acid listed in a different group of the six standard amino acid groups (1) to (6) shown above.

In various embodiments, the DNASE1 (D1) variant evaluated and selected for use in therapy in accordance with embodiments of the invention comprises an amino acid sequence that is at least 80% identical to the enzyme defined by SEQ ID NO: 1, with one or more building block substitutions.

In some aspects, the building block substitutions are selected from non-human D1 proteins and result in variants of human D1, which feature one or more of the following mutations: K24R, I25M, Q31R, T32S, E35D, V44S, V44T, V44A, S45V, S45K, S45N, S45H, Q49K, Q49R, S52Q, S52R, R53L, I56V, A57V, L58V, V59I, S60T, T68V, D75N, N76E, N76K, N76T, N76E, N76Y, N76S, Q79R, Q79E, D80K, D80H, A81K, A81I, A81D, P82A, P82T, D83N, D83G, T84N, T84A, Y85F, H86R, Y87F, Y87H, V88I, V89I, V89A, N96K, N96R, N96S, S97T, R101Q, V105L, Y106F, D109S, Q110R, Q110K, A113V, A113I, S114L, S116T, Y108Q, Y108H, Y108L, P125S, N128T, T130S, N132S, N132A, A1365, I137V, R139K, F141S, F141H, S142C, R143P, R143H, F144Y, F144S, F144L, V147K, V147Q, R148Q, R148S, E149K, I152V, P154A, A1575, G160E, G160T, G160L, G160S, D161E, V163A, S164S, D167N, A168S, D175N, Q177W, Q177R, E178Q, E178K, E178H, G181D, G181H, E183Q, E183N, V185I, M186V, L187F, G194D, C195Y, R199T, R199A, R199S, P200S, P200A, P200T, P200L, Q202H, S204A, W209R, T210M, T210E, P212S, T213A, T213I, T213P, Q215K, Q215R, P219L, S221T, S221N, A226V, A226S, T227S, T227K, P228S, H230N, A232P, M241T, M241A, M241P, M241S, R244Q, G245D, G245A, G245H, G245R, G245S, D250N, D250S, D250E, D250G, L253V, L253A, L253M, N256D, A259V, A260E, Y261F, G262R, S264T, D265N, D265S, D265E, Q266E, L267M, L267T, Q269E, Q269L, M280T, M280A, K282R, K282A, K282T, K282insK, and K282insR.

In some embodiments, the building block substitutions to D1 are selected from human D1L1 and result in variants of human D1 which feature one or more of the following mutations: M1 G3del, K5G8delinsHYPT, A12F, L14Q15delinsAN, V21_K24delinsQAFR, A26C, I30A, T32_T36delinsRLTLA, M38_I47delinsVAREQVMDTL, Q49R, S52A, Y54C, A57_V59delinsMVL, R63V, H66_T68delinsSGS, V70_K72delinsIPL, D75_N76delinsRE, Q79delinsRF, A81_T84delinsGSGP, H86_V89delinsSTLS, E91_P92delinsPQ, N96_S97delinsST, K99M, R101T, L103_V105delinsVYF, P108_D115delinsSHKTQVLS, Y118V, D120N, G122_N128delinsED, T130V, A136_R139delinsFVAQ, F141_I152delinsSLPSNVLPSLVL, A157_A158delinsTT, G160_A164delinsKAVEK, I166_D167delinsLN, Y173F, D175E, G177_E179delinsQSK, M186L, G194D, S196_R207delinsASLTKKRLDKLE, W209R, S211E, T213G, Q215H, L217V, P219A, S221_A222delinsGE, A226_P228delinsVRAS, A232T, I236V, V238 A239delinsLH, M241_L243delinsERC, G245_S251delinsSLLHT, L253_P254delinsAA, N256D, Q259_G262delinsPTSQG, S264_L267delinsTEEE, Q269_A270delinsLN, M280E, and K282delinsKLSQAHSVQPLSLTVLLLLSLLSPQLCPAA.

In certain embodiments, the building block substitutions to D1 are selected from human D1L2 and result in variants of human D1 which feature one or more of the following mutations: R2G, M4 KSdelinsPRA, G8A, L11W, A14E, L16Q18delinsA, A20_S22delinsTAA, K24R, A26G, T32S, E35 T36delinsDS, M38V, N40_V44delinsDPACG, Y46I, V48_Q49delinsAK, S52_R53delinsAG, I56L, S65_H66delinsPD, T68S, S70_A71delinsGK, L74_L77delinsMEQI, Q79_T84delinsSVSEHE, H86_Y87delinsSF, V89S, E91Q, D95_Q96delinsNS, R101M, P108K, Q110A, A113V, S116T, Y118L, P119D, G122_N128delinsPE, T130V, N132S, A136_I137delinsFV, R139K, F141_F144delinsSAPG, E146_V153delinsGERAPPLPSRRALTPPLPAAAQNLVLI, G160_D161delinsHQ, Q177_E178delinsID, L182_E182delinsTD, V185_M188delinsMLFL, G194D, P200_Q202delinsAQD, S204_S205delinsAA, W209_T210delinsRS, P212_T213delinsEV, Q230K, A226_H230delinsVGNSD, V239_A240delinsAC, M241_L242delinsAR, G245_V248delinsRSLK, D250Q, L253_N256delinsTVHD, A259_Y262delinsEEF, S264_L267delinsDQTQ, Q269L, Y275F, M280T, and K282insFHR.

In some embodiments, the building block substitutions to D1 are selected from human DNASE1-LIKE 3 Isoform 1 (D1L3) and result in variants of human D1, which feature one or more of the following mutations: M1_L6delinsMSRE, G8_A9deinsAP, A12L, A14_G19delinsLLSIHS, V21_K24delinsLAMR, A26_A27delinsCS, I30_T32delinsVRS, S36T, M38_Y46delinsQEDKNAMDV, Q49_S52delinsKVIK, Y54C, A57I, Q60M, V62_R63delinsIK, H66_K72delinsNNRICPI, L74_N76delinsMEK, Q79_D83delinsRNSRRGI, H86N, V89I, E91_P92delinsSR, S97T, R101Q, L103A, V105L, R107 Q110delinsKEKL, A113_D115delinsVKR, Y118H, D120H, G122_N128delinsYQDGDA, T130V, N132S; A136_I137delinsFV, R139W, F141Q, R143_F144delinsPH, E146A, R148_E149delinsKD, A151V, V153I, A157_A 158delinsTT, G160_A162delinsETS, A164K, A168E, Y170_D171delinsVE, L174T, Q177_K179delinsKHR, G181_L182delinsKA, D184_L187delisNFIF, R199_Q202delisPKKA, S204_S205delinsKN, W209R, S211D, T213R, Q215V, P219G, S221_A222delinsQE, A226_P228delinsVKKS, H230N, V238_A239delinsLR, M241_A246delinsQEIVSS, D250K, A252_P254delinsNSV, N256D, A259K, G262K, S264_L267delinsTEEE, Q269_I271delinsLDV, Y275F, V279_M280delinsFK, and K282delinsQSSRAFTNSKKSVTLRKKTKSKRS.

In some embodiments, the building block substitutions to D1 are selected from human DNASE1-LIKE 3 Isoform 2

(D1L3-2) and result in variants of human D1, which feature one or more of the following mutations: M1_L6delinsMSRE, G8_A9deinsAP, A12L, A14_G19delinsLLSIHS, V21_K24delinsLAMR, A26_A27delinsCS, I30_T32delinsVRS, T36S, M38_Y46delinsQEDKNAMDV, Q49_S52delinsKVIK, Y52C, A57I, Q60M, V62_R63delinsIK, H66_K72delinsNNRICPI, L74N76delinsMEK, Q79_Y106deL, P108_Q110delinsEKL, A113_D11SdelinsVKR, Y118H, D120H, G122_N128delinsYQDGDA, T130V, N132S, A136_I137delinsFV, R139W, F141Q, R143_F144delinsPH, E146A, R148_E149delinsKD, A151V, VI531, A157_A158delinsAA, G160_A162delinsETS, A164K, Y170D171delinsVE, L174T, Q177_K179delinsKHR, G181_L 182delinsKA, D184_L 187delisNFIF, R199_Q202delisPKKA, S204_S205delinsKN, W209R, S211D, T231R, Q215V, P219G, S221_S222delinsQE, A226_P228delinsVKKS, H230N, V238_A239delinsLR, M241 _A246delinsQEIVSS, D250K, A252_P254delinsNSV, N256D, G262K. S264_L267delinsTEEE, Q269_I271delinsLDV, Y275F, V279_M280delinsFK, and K282delinsQSSRAFTNSKKSVTLRKKTKSKRS.

In various embodiments, the D1 variant evaluated in accordance with the disclosure comprises the D1 wildtype amino acid sequence or a variant sequence described herein, fused to the C-terminus of a carrier protein, with a linking amino acid sequence. In some embodiments, the carrier protein is Fc fragment or albumin. In some embodiments, the carrier protein is human albumin. The linking sequence can be a flexible linker predominately composed of Gly, or Gy and Ser. In some embodiments, the linker is composed of Gly and amino acids having hydrophilic side chains (e.g., Ser, Thr). In some embodiments, the linker is from 5 to 20 amino acids. An exemplary linker has the structure (GGGGS)$_3$.

In various embodiments, the peptide linker may be a flexible linker, a rigid linker, or in some embodiments a physiologically-cleavable linker (e.g., a protease-cleavable linker). In some embodiments, the linker is 5 to 100 amino acids in length, or is 5 to 50 amino acids in length.

Linkers, where present, can be selected from flexible, rigid, and cleavable peptide linkers. Flexible linkers are predominately or entirely composed of small, non-polar or polar residues such as Gly, Ser and Thr. An exemplary flexible linker comprises (Gly$_y$Ser)$_n$ linkers, where y is from 1 to 10 (e.g., from 1 to 5), and n is from 1 to about 10, and in some embodiments, is from 3 to about 6. In exemplary embodiments, y is from 2 to 4, and n is from 3 to 8. Due to their flexibility, these linkers are unstructured. More rigid linkers include polyproline or poly Pro-Ala motifs and α-helical linkers. An exemplary α-helical linker is A(EAAAK)$_n$A, where n is as defined above (e.g., from 1 to 10, or 2 to 6). Generally, linkers can be predominately composed of amino acids selected from Gly, Ser, Thr, Ala, and Pro. Exemplary linker sequences contain at least 10 amino acids, and may be in the range of 15 to 35 amino acids. Exemplary linker designs are provided as SEQ ID NOS: 41 to 51.

In some embodiments, the variant comprises a linker, wherein the amino acid sequence of the linker is predominately glycine and serine residues, or consists essentially of glycine and serine residues. In some embodiments, the ratio of Ser and Gly in the linker is, respectively, from about 1:1 to about 1:10, from about 1:2 to about 1:6, or about 1:4. Exemplary linker sequences comprise S(GGS)$_4$GSS (SEQ ID NO: 46), S(GGS)$_9$GS (SEQ ID NO: 47), (GGS)$_9$GS (SEQ ID NO: 48). In some embodiments, the linker has at least 10 amino acids, or at least 15 amino acids, or at least 20 amino acids, or at least 25 amino acids. For example, the linker may have a length of from 15 to 30 amino acids. In various embodiments, longer linkers of at least 15 amino acids can provide improvements in yield upon expression in *Pichia pastoris*.

In other embodiments, the linker is a physiologically-cleavable linker, such as a protease-cleavable linker. For example, the protease may be a coagulation pathway protease, such as activated Factor XII. In certain embodiments, the linker comprises the amino acid sequence of Factor XI (SEQ ID NO: 49) and/or prekallikrein (SEQ ID NO: 50 or 51) or a physiologically cleavable fragment thereof. In other embodiments, the linker includes a peptide sequence that is targeted for cleavage by a neutrophil specific protease, such as neutrophil elastase, cathepsin G, and proteinase 3.

In various embodiments, the human DNASE1-LIKE 1 (DIL1) variant evaluated and selected for use in therapy in accordance with embodiments of the invention comprise an amino acid sequence that is at least 80% identical to the enzyme defined by SEQ ID NO: 2, with one or more building block substitutions.

In some embodiments, the building block substitutions to D1L1 are selected from non-human D1L1 proteins and result in variants of human D1L1 which feature one or more of the following mutations: A26T, Q27H, A32T, A325, V34L, A35T, A35I, R36K, Q38S, Q38E, Q38H, Q38Y, Q38P, Q38D, M40K, M40L, T42I, L43F, R45Q, R45K, L47V, M53T, S61A, S62T, G63Q, G63D, G63N, G63S, S64N, S64A, S64K, S64T, A65T, P66L, P66S, L68F, R71Q, R71E, E72K, N74S, R75K, F76Y, D77K, D77Q, D77Y, D77G, G78A, G78S, G78N, G78D, G80R, G80K, P81S, P81F, P81C, S83R, T84F, T84S, L85H, S86N, S86K, P88S, P88D, Q89L, Q89M, S93N, S93G, T94A, M96V, M96K, T98K, V100A, F102I, H106D, K107R, K107E, K107R, T108A, Q109E, V110L, L111R, S112N, S112D, S112E, S113F, V115Q, V115L, V115M, N117D, N117E, N117P, N177S, E119T, E119Q, E119K, V122I, V122L, A124T, A130G, A130C, Q131H, Q131W, S133T, L134F, P135R, N137D, N137K, V138T, V138I, L142V, V143A, A153D, K156P, K156N, K156T, L159K, Y162H, D163E, D163T, E167D, V168A, S169Y, S169A, Q170R, Q170G, H171R, S174N, S174T, K175E, K175Q, S176N, V177M, V177I, A188T, T191A, T191N, D196K, D196N, D196S, D196A, D196G, E199L, E199A, E199V, E203K, E203D, E203Q, P204A, P204V, P204T, H207R, H207S, V209A, I210V, A211P, E214D, E241V, H223N, T225A, V229I, L231V, L231M, E234Q, E234V, R235G, R235T, R235L, C236L, R237Q, S238M, S238K, S238G, L240M, H241K, H241Q, H241S, H241R, T242A, T242S, T242N, T242G, A244T, D247N, T240K, T250R, Q250Q, S251T, S251R, Q252R, Q252G, T255N, T255S, E258Q, E259Q, N261R, N261K, M261T, I262V, E271D, K273S, K273N, K273D, K273A, L274del, S275Q, S275K, S275R, Q276A, A277T, A277V, H278P, H278Q, 5279G, S279N, S279R, C279S, I280V, A280V, Q281P, Q281L, L283H, L283P, S284Y, S284C, S284H, 5284G, T286A, T286S, T286V, V287T, V287A, F287F, G287V, L288A, L288S, L289S, L289V, L289M, S292L, S292P, S295P, S295T, S295A, P296S, Q297E, L298C, C299D, C299G, C299S, P300L, A301Q, A301V, and A302M.

In some embodiments, the building block substitutions to D1L1 are selected from human D1 and result in variants of human D1L1 which feature one or more of the following mutations: M1delinsMRGM, H2_T5delinsKLLG, F9A, A13_N14delinsLQ, Q17_R20delinsVLSK, C22A, A26I, R28_A32delinsTFGET, V34_L43delinsMSNATLVSYI, R45Q, A48S, C50Y, M53_L55delinsALV, V59R, S62_S64delisHLT, 166_L68delinsVGK, R71_E72delinsDN, R75_F76delinsQ, G78_P81delinsAPDT, S83_S86delinsHYVV, P88_Q89delinsEP, S93_T94delinsNS, M96K, T98R, V100_F102delinsLFV, S105_S112delinsPDQVSAVD, V115Y, N117D, E119_D120delinsGCEPCGN, V122T, F128_Q131 delinsAIVR, S133_L144delinsFSRFTEVREFAI, T149_T150delinsAA, K152_K156delinsGDAVA, L158_N159delinsID, F165Y, E167D, Q173_K175delinsGLE, M188L, D186G, A188_E199delinsSYVRPSQWSSIR, R201W, E203S, G205T, H207Q, V209L, A211P, G213_E214delinsSA, V218_S221delinsATP, T225A, V229I, L231_H232delinsVA, E234_C236delinsMLL, S238_T242delinsGAVVPDS, A244_A245delinsLP, D247N, P249_Q253delinsQAAYG, T255_E258delinsSDQL, L260_N261delinsQA, E271M, and L274_A302del.

In some embodiments, the building block substitutions to D1L1 are selected from human D1L2 and result in variants of human D1L1 which feature one or more of the following mutations: H2_Y3delinsGG, TSR, F9_L12delinsWALE, N14A, A16_Q17delinsTA, F19L, C22G, A26I, R28_A32delinsSFGDS, A35_R45delinsSDPACGSIIAK, R49_50CdelinsGY, 152_L55delinsLALV, V59R, S61_G63delinsPDL, I66_L68delinsVSA, L70_L73delinsMEQI, R75_P81delinsSVSEHE, T84_L85delinsFV, P88_Q89delinsQP, S93_T94delinsDQ, M96K, T98M, V100_F102delinsLFV, S105_Q109delinsKDAVS, L111_S113delinsVDT, V115L, N117P, E119_P120delinsPE, A124S, A130_Q131delinsVK, L134A, S136_V138delinsGTGERAPP, S141_L142insRRALTPPPLPAAAQN, V145I, T149_T150delinsAA, K152_K156delinsHQAVA, L158_N159delinsID, F165Y, E167D, S169_H171delinsIDK, V177_L179delinsMLF, A188_E199delinsSYVRAQDWAAIR, T202_G205delinsSSEV, H207K, V209L, A211P, G213_E214delinsSA, R219_H223delinsGNSD, T225A, V229I, L231_H232delinsAC, E234A, C236L, S238_L239delinsRS, H241_T242delinsKPQS, A244_F246delinsTVH, P249_S251delinsQEE, Q253G, T255_E258delinsDQTQ, N261A, Y266F, E271T, and L274_A302delinsFHR.

In some embodiments, the building block substitutions to D1L1 are selected from human DNASE1-LIKE 3 Isoform I (DIL3) and result in variants of human D1L1, which feature one or more of the following mutations: H2_T5delinsSREL, L7_L8insPLL, F9L, I11_G14delinsLSIHS, Q17L, F19M, A23S, A26_A32delinsVRSFGES, V34_V39delinsQEDKNA, T42_L43delinsVI, R45_A48delinsKVIK, M53_Q56delinsILVM, V58_V59delinsIK, S62_I66delinsNNRIC, L68I, L70_E72delinsMEK, F76_S79delinsNSRR, G80_P81delinsIT, S83_S86delinsNYVI, P88_Q89delinsPQ, S92N, M96K, T98Q, V100_F102delinsAFL, R104_Q109delinsKEKLVS, L111_S112delinsKR, V115H, N117H, E119_D120delinsYQDGDA, A124S, A130_Q131delinsVW, S133_L134delinsQS, S136L142delinsHTAVKDF, L144_V145delinsII, K152_E155delinsETSV, L158_A160delinsIDE, Y162_D163delinsVE, F165_E167delinsVTD, S169_H171delinsKHR, Q173_V177delinsKAENF, D186G, A188_T191delinsSYVP, R194_E199delinsAWKNIR, E203D, G205R, H207V, V209L, A211G, G213Q, R219_A220delinsKK, H223N, T225A, V229I, H232R, E234_R237delinsQEIV, L239_A245delinsSVVPKSNSV, P249_Q253delinsQKAYK, N261_I262delinsDV, Y266F, V270E271delinsFK, K273_L274delinsQS, Q276R, H278_L283delinsFTNSKK, L285V, and V287_A302delinsLRKKTKSKRS.

In some embodiments, the building block substitutions to D1L1 are selected from human DNASE1-LIKE 3 Isoform 2 (D1L3-2) and result in variants of human D1L1, which feature one or more of the following mutations: H2 T5delinsSREL, A7delinsPLL, F9L, I11_G14delinsLSIHS, Q17L, F19M, S23A, A26_A32delinsVRSFGES, V34_V39delinsQEDKNA, T42_L43delinsVI, R45_A48delinsKVIK, M53_Q56delinsILVM, V58_V59delinsIK, S62_I66delinsNNRIC, L68I, L70_E72delinsMEK, F75_Q103del, S105_Q109delinsEKLVS, L111_S112delinsKR, V115H, N117H, E119_D120delinsYQDGDA, A124S, A130_Q131delinsVW, S133_L134delinsQS, S136_L142delinsHTAVKDF, L144_V145delinsII, K152_E155delinsETSV, L158_A160delinsIDE, Y162_D163delinsVE, F165_E167delinsVTD, S169_H171 delinsKHR, Q173_V177delinsKAENF, D186G, A188_T191delinsSYVP, R194_E199delinsAWKNIR, E203D, G205R, H207V, V209L, A211G, G213Q, R219_A220delinsKK, H223N, T225A, V229I, H232R, E234_R237delinsQEIV, L239_A245delinsSVVPKSNSV, P249_Q253delinsQKAYK, N261_I262delinsDV, Y266F, V270_E271delinsFK, K273_L274delinsQS, Q276R, H278_L283delinsFTNSKK, L285V, and V287_A302delinsLRKKTKSKRS.

In certain embodiments, the D1L1 protein variant contains one or more amino acid substitutions, additions, or deletions in the C-terminal tail domain defined by SEQ ID NO: 8. The C-terminal tail domain or a portion thereof may be deleted. In some embodiments, at least 3, 5, 8, 10, 12, 15, 18, or 23 amino acids of the C-terminal tail domain are deleted.

In various embodiments, the D1L1 variant evaluated in accordance with the disclosure comprises the D1L1 wild-type amino acid sequence or a variant sequence described herein, fused to the C-terminus of a carrier protein, with a linking amino acid sequence. In some embodiments, the carrier protein is Fc fragment or albumin. In some embodiments, the carrier protein is human albumin. The linking sequence, which is also herein referred to as a peptide linker, or a linker, can be a flexible linker predominately composed of Gly, or Gy and Ser. In some embodiments, the linker is composed of Gly and amino acids having hydrophilic side chains (e.g., Ser, Thr). In some embodiments, the linker is from 5 to 20 amino acids. An exemplary linker has the structure $(GGGGS)_3$.

The peptide linker may be a flexible linker, a rigid linker, or in some embodiments a physiologically-cleavable linker (e.g., a protease-cleavable linker). In some embodiments, the linker is 5 to 100 amino acids in length, or is 5 to 50 amino acids in length.

Linkers, where present, can be selected from flexible, rigid, and cleavable peptide linkers. Flexible linkers are predominately or entirely composed of small, non-polar or polar residues such as Gly, Ser and Thr. An exemplary flexible linker comprises $(Gly_y Ser)_n$ linkers, where y is from 1 to 10 (e.g., from 1 to 5), and n is from 1 to about 10, and in some embodiments, is from 3 to about 6. In exemplary embodiments, y is from 2 to 4, and n is from 3 to 8. Due to their flexibility, these linkers are unstructured. More rigid linkers include polyproline or poly Pro-Ala motifs and α-helical linkers. An exemplary α-helical linker is A(EAAAK)$_n$A, where n is as defined above (e.g., from 1 to 10, or 2 to 6). Generally, linkers can be predominately composed of amino acids selected from Gly, Ser, Thr, Ala, and Pro. Exemplary linker sequences contain at least 10 amino acids, and may be in the range of 15 to 35 amino acids. Exemplary linker designs are provided as SEQ ID NOS: 41 to 51.

In some embodiments, the variant comprises a linker, wherein the amino acid sequence of the linker is predominately glycine and serine residues, or consists essentially of glycine and serine residues. In some embodiments, the ratio of Ser and Gly in the linker is, respectively, from about 1:1 to about 1:10, from about 1:2 to about 1:6, or about 1:4. Exemplary linker sequences comprise S(GGS)$_4$GSS (SEQ ID NO: 46), S(GGS)$_9$GS (SEQ ID NO: 47), (GGS)$_9$GS(SEQ ID NO: 48). In some embodiments, the linker has at least 10 amino acids, or at least 15 amino acids, or at least 20 amino acids, or at least 25 amino acids. For example, the linker may have a length of from 15 to 30 amino acids. In various embodiments, longer linkers of at least 15 amino acids can provide improvements in yield upon expression in *Pichia pastoris*.

In other embodiments, the linker is a physiologically-cleavable linker, such as a protease-cleavable linker. For example, the protease may be a coagulation pathway protease, such as activated Factor XII. In certain embodiments, the linker comprises the amino acid sequence of Factor XI (SEQ ID NO: 49) and/or prekallikrein (SEQ ID NO: 50 or 51) or a physiologically cleavable fragment thereof. In other embodiments, the linker includes a peptide sequence that is targeted for cleavage by a neutrophil specific protease, such as neutrophil elastase, cathepsin G, and proteinase 3.

In various embodiments, the human DNASE1-LIKE 1 (D1L2) variant evaluated and selected for therapy in accordance with this disclosure comprises an amino acid sequence that is at least 80% identical to the enzyme defined by SEQ ID NO: 3, with one or more building block substitutions.

In some embodiments, the building block substitutions to D1L2 are selected from non-human D1L2 proteins and result in variants of human D1L2, which feature one or more of the following mutations: L22K, I24V, I29V, S35N, S35H, S35R, 535T, V37A, S38L, A41D, A41V, A41G, G43I, S44G, S44i, I45V, K48Q, L55I, L55V, A56T, A56M, P64A, S70D, S70T, A71T, A71L, A71S, A71V, M73L, E74Q, N77H, S78R, E81K, E81R, E83N, S85G, S85N, Q90E, Q90K, Q96H, F103Y, V104I, K107D, A109V, A109T, A109K, V110A, V113L, V113M, D114S, D114E, L117Q, P119S, E122G, V124A, V124F, S126N, E128D, F134V, A136V, A136T, G138S, G138R, T139S, T139C, S148C, A151P, P154A, A159P, A160G, A161P, A161T, Q162D, Q162K, Q162R, Q162T, N163K, N163E, L164V, L164F, I167V, H174N, Q175H, A178T, A178V, D192N, G195N, T196S, D198V, M199L, M199I, S210K, R213K, Q215H, A218P, A219S, E226Q, V227I, S243T, A252V, C253S, A255S, A255V, R256H, L257M, R259K, S260T, L261V, Q264H, T267S, T267A, D270N, G276D, G276S, T280S, T280D, T280A, A284C, I286V, L295F, F297S, F297T, F297P, H298R, and R299del.

In some embodiments, the building block substitutions to D1L2 are selected from human D1 and result in variants of human D1L2, which feature one or more of the following mutations: G2R, P4_A6delinsMK, A9G, W12L, EISA, A16_G18delinsLLQ, T19_A21delinsAVS, R23K, G25A, S31T, D34_S35delinsET, V37M, D39_G43delinsNATLV, I45Y, A47_K48delinsVQ, A51_G52delinsSR, L55I, P64_D65delinsSH, S67T, S70_A71delinsGK, M73_I76delinsLDNL, S78_E83delinsQDAPDT, S85_F86delinsHY, S88V, Q90E, D95_Q96delinsNS, M100R, K107P, A109Q, V112A, T115S, L117Y, P119D, P121_E122delinsGCEPCGN, V124T, S126N, F130_V131delinsI, K133R, S135_G138delinsFSRF, G140I167delinsEVREFAIV, H174_Q175delinsGD, I191_D192delinsQE, T196_D197delinsLE, M199_L202delinsVMLM, D208G, A214_D216delinsPSQ, A218_A219delinsSS, R223_S224delinsWT, E226_V227delinsPT, K229Q, V240_D244delinsATPTH, A252_C253delinsVA, A225_R256delinsML, R259_K262delinsGAVV, Q264D, T267_D270delinsLPFN, E273_E275delinsAAY, D278_Q281delinsSDQL, L283Q, F283Y, T294M, and F297_R299del.

In some embodiments, the building block substitutions to D1L2 are selected from human D1L1 and result in variants of human D1L2, which feature one or more of the following mutations: G2_G3delinsHY, R5T, W12_E15delinsFLIL, A17N, T19_A20delinsAQ, L22F, G25C, I29A, S31_S35delinsRLTLA, S38_K48delinsAREQVMDTLVR, G52_Y53delinsRC, L55_V58delinsIMVL, R62V, P64_L66delinsSSG, V69_A71delinsIPL, M73_I76delinsLREL, S78_E83delinsRFDGSGP, F86_V87delinsTL, Q90_P91delinsPQ, D95_Q96delinsST, K98M, M100T, L102_V104delinsVYF, K107_S111delinsSHKTQ, V113_T115delinsLSS, L117V, P119N, P121_E122delinsED, S126A, V132_K133delinsAQ, A136L, G138_P145delinsSNV, R149_N163del, I167V, A171_A172delinsTT, H174_A178delinsKAVEK, I180_D181delinsLN, Y187F, D189E, I191_K193delinsSQH, M199_F201delinsVIL, S210_R221delinsASLTKKRLDKLE, S224_V227delinsTEPG, K229H, L231V, P233A, S235_A235delinsGE, G241_D244delinsRASTH, A246T, I250V, A252_C253delinsLH, A255E, L257C, R259_S260delinsSL, K262_S265delinsHT, T267_H269delinsAAF, Q272_E274delinsPTS, G276Q, D278_Q281delinsTEEE, A284N, F289Y, T294E, and F297_R299delinsLSQAHSVQPLSTVLLLLSLLSPQLCPAA.

In some embodiments, the building block substitutions to D1L2 are selected from human DNASE1-LIKE 3 Isoform 1 (D1L3) and result in variants of human D1L2, which feature one or more of the following mutations: G2_R5delinsSREL, L7P, A9_A10delinsL, W12_A13delinsLL, S15_A20delinsSIHSAL, L22M, G25_A26delinsCS, I29_Q30delinsVR, D34E, V37_S38delinsQE, P40_I45delinsKNAMDV, A47V, I49_Y53delinsVIKRS, L55_A56delinsII, Q59M, V61_R62delinsIK, P64_A71delinsSNNRICPI, Q75_I76delinsKL, N77_S78insRS, V79_E83delinsRRGIT, S85_F86delinsNY, S88I, Q90_P91delinsSR, D95_Q96delinsNT, M100Q, L102A, V104L, R106_A109delinsKEKL, V113_T115delinsKRS, L117H, P119H, P121_E122delinsYQDGDA, K133W, S135_A136delinsQS, G138H, G140_A159del, A161_L164delinsVKDF, L166I, A171_A172delinsTT, H174_A176delinsETS, A178K, A182E, Y184_D185delinsVE, L188T, I191_K193delinsKHR, G195_L200delinsKAENFI, L202M, D208G, R213_D126delinsPKKA, A218_A129delinsKN, S224_V227delinsTDPR, K229V, P233G, S235_A236delinsQE, G241_N242delinsKK, S243_D244insTN, A252_C253delinsLR, A255_R259delinsQEIVS, L261_K262delinsVV, Q264K, A266_T267delinsNS, H269F, E273_G276delinsKAYK, D278_Q281delinsTEEE, A284_I285delinDV, V293_T294delinsFK, K296_H298delinsQSS, and R295insAFTNSKKSVTLRKKTKSKRS.

In some embodiments, the building block substitutions to D1L2 are selected from human DNASE1-LIKE 3 Isoform 2 (D1L3-2) and result in variants of human D1L2, which feature one or more of the following mutations: G2 R5delinsSREL, L7P, A9 _A10delinsL, W12_A13delinsLL, S15_A20delinsSIHSAL, L22M, G25_A26delinsCS, I29_Q30delinsVR, D34E, V37_S38delinsQE, P40_I45delinsKNAMDV, A47V, I49_Y53delinsVIKRS, L55_A56delinsII, Q59M, V61_R62delinsIK, P64_A71delinsSNNRICPI, Q75_I76delinsKL, K107_A109delinsEKL, V113_T115delinsKRS, L117H, P119H, P121_E122delinsYQDGDA, K133W, S135_A136delinsQS, G138H, G140_A159del, A161_L164delinsVKDF, L166I, A171_A172delinsTT, H174_A176delinsETS, A178K, A182E, Y184_D185delinsVE, L188T, I191_K193delinsKHR, G195_L200delinsKAENFI, L202M, D208G, R213_D126delinsPKKA, A218_A129delinsKN, S224_V227delinsTDPR, K229V, P233G, S235_A236delinsQE, G241_N242delinsKK, S243_D244insTN, A252_C253delinsLR, A255_R259delinsQEIVS, L261_K262delinsVV, Q264K, A266_T267delinsNS, H269F, E273_G276delinsKAYK, D278_Q281delinsTEEE, A284_I285delinDV, V293_T294delinsFK, K296_H298delinsQSS, and R295insAFTNSKKSVTLRKKTKSKRS.

In certain embodiments, the D1L2 protein variant contains one or more amino acid substitutions, additions, or deletions in the proline-rich extension domain defined by SEQ ID NO: 9. The proline-rich extension domain or a portion thereof may be deleted, including a deletion (or truncation) of at least 3 amino acids, at least 5 amino acids, or at least 10 amino acids.

In various embodiments, the D1L2 variant evaluated in accordance with the disclosure comprises the D1L2 wild-type amino acid sequence or a variant sequence described herein, fused to the C-terminus of a carrier protein, with a linking amino acid sequence. In some embodiments, the carrier protein is Fc fragment or albumin. In some embodiments, the carrier protein is human albumin. The linking sequence can be a flexible linker predominately composed of Gly, or Gy and Ser. In some embodiments, the linker is composed of Gly and amino acids having hydrophilic side chains (e.g., Ser, Thr). In some embodiments, the linker is from 5 to 20 amino acids. An exemplary linker has the structure (GGGGS)$_3$.

The peptide linker may be a flexible linker, a rigid linker, or in some embodiments a physiologically-cleavable linker (e.g., a protease-cleavable linker). In some embodiments, the linker is 5 to 100 amino acids in length, or is 5 to 50 amino acids in length.

Linkers, where present, can be selected from flexible, rigid, and cleavable peptide linkers. Flexible linkers are predominately or entirely composed of small, non-polar or polar residues such as Gly, Ser and Thr. An exemplary flexible linker comprises (Gly$_y$Ser)n linkers, where y is from 1 to 10 (e.g., from 1 to 5), and n is from 1 to about 10, and in some embodiments, is from 3 to about 6. In exemplary embodiments, y is from 2 to 4, and n is from 3 to 8. Due to their flexibility, these linkers are unstructured. More rigid linkers include polyproline or poly Pro-Ala motifs and α-helical linkers. An exemplary α-helical linker is A(EAAAK)$_n$A, where n is as defined above (e.g., from 1 to 10, or 2 to 6). Generally, linkers can be predominately composed of amino acids selected from Gly, Ser, Thr, Ala, and Pro. Exemplary linker sequences contain at least 10 amino acids, and may be in the range of 15 to 35 amino acids. Exemplary linker designs are provided as SEQ ID NOS: 41 to 51.

In some embodiments, the variant comprises a linker, wherein the amino acid sequence of the linker is predominately glycine and serine residues, or consists essentially of glycine and serine residues. In some embodiments, the ratio of Ser and Gly in the linker is, respectively, from about 1:1 to about 1:10, from about 1:2 to about 1:6, or about 1:4. Exemplary linker sequences comprise S(GGS)$_4$GSS (SEQ ID NO: 46), S(GGS)$_9$GS (SEQ ID NO: 47), (GGS)$_9$GS (SEQ ID NO: 48). In some embodiments, the linker has at least 10 amino acids, or at least 15 amino acids, or at least 20 amino acids, or at least 25 amino acids. For example, the linker may have a length of from 15 to 30 amino acids. In various embodiments, longer linkers of at least 15 amino acids can provide improvements in yield upon expression in *Pichia pastoris*.

In other embodiments, the linker is a physiologically-cleavable linker, such as a protease-cleavable linker. For example, the protease may be a coagulation pathway protease, such as activated Factor XII. In certain embodiments, the linker comprises the amino acid sequence of Factor XI (SEQ ID NO: 49) and/or prekallikrein (SEQ ID NO: 50 or 51) or a physiologically cleavable fragment thereof. In other embodiments, the linker includes a peptide sequence that is targeted for cleavage by a neutrophil specific protease, such as neutrophil elastase, cathepsin G, and proteinase 3.

In some embodiments, the human DNASE1-LIKE 3 Isoform 1 (D1L3) variant evaluated and selected for use in therapy in accordance with embodiments of the invention may comprise an amino acid sequence that is at least 80% identical to the enzyme defined by SEQ ID NO: 4, and may have one or more building block substitutions. As further disclosed in U.S. Pat. No. 10,696,956 (which is incorporated herein by reference), the D1L3 variant may comprise an amino acid sequence that has at least 90%, or at least 95%, or at least 97%, or at least 98% sequence identity with with the DNase enzyme defined by SEQ ID NO: 4.

Figure 2:
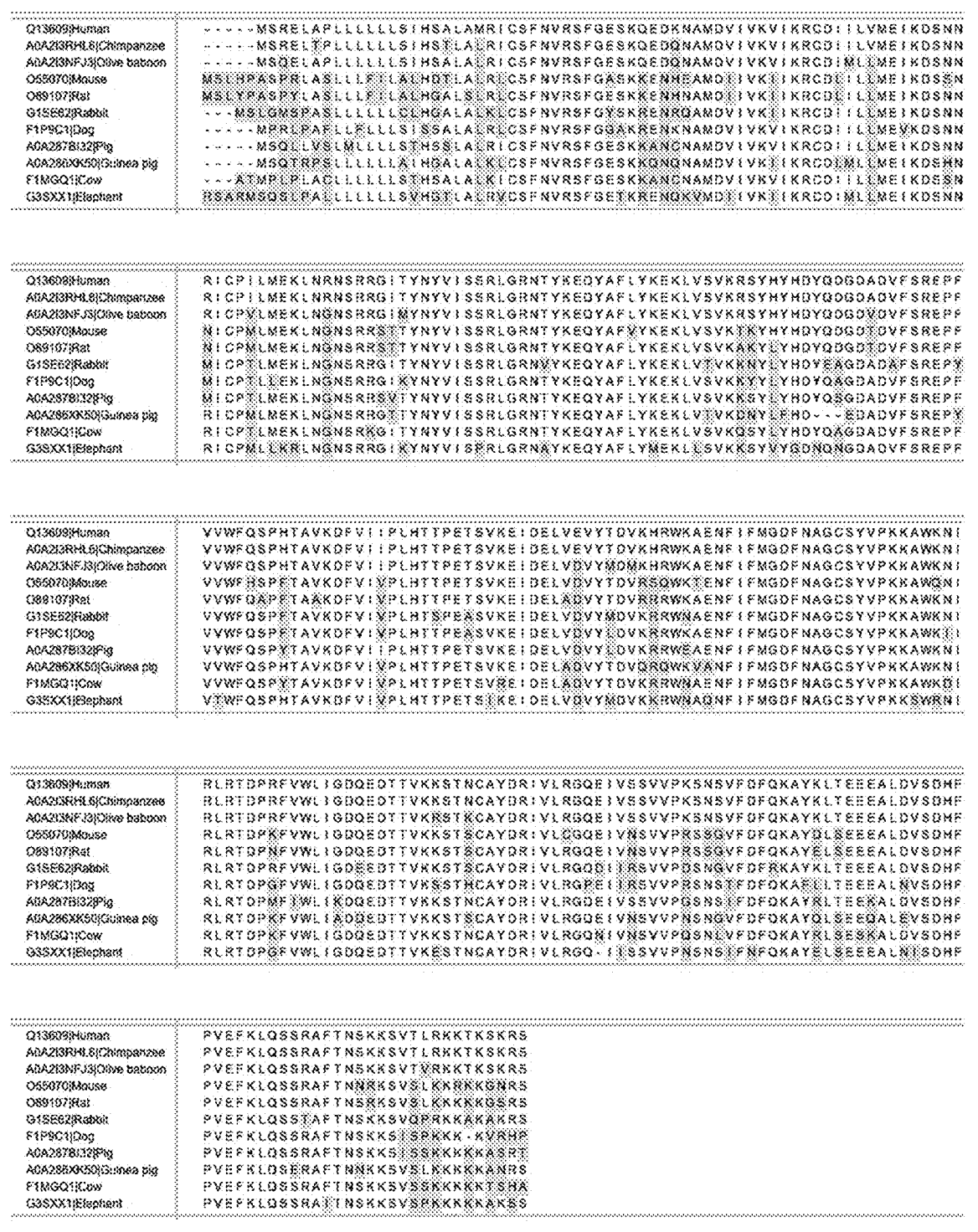

In some embodiments, the building block substitutions to D1L3 are selected from non-human D1L3 proteins, such as chimpanzee, olive baboon, mouse, rat, dog, pig, guinea pig, cow, and elephant (See FIG. 2). In various embodiments, the building block substitution resultd in variants of human D1L3 which feature one or more of the following mutations: M21L, K22R, I22L, I22V, E33A, E33Y, E33G, S34A, S34T, Q36K, Q36R, E37A, E37Q, D48N, K39Q, K39H, K39R, K39C, N40E, N40Q, N40K, A41V, V44I, V53I, I53L, I54M, V57L, I60V, N64S, H64S, R66N, R66M, I70V, I70M, I70T, M72L, E73K, K74R, R77G, R81K, G82S, I83V, I83T, T84M, T84K, S91P, T91V, T91A, L105V, K107M, V111L, S112T, R115T, R115A, R115K, R115D, R115Q, S116K, S116N, S116Y, H118L, H118V, Y119F, H120G, Y122N, Q123E, D124A, D124S, D124N, G125E, A127V, A127T, V129A, F135Y, V137T, Q140H, S141A, H143F, H143Y, V146A, I152V, T157S, T160A, V162I, K163R, V169A, E170D, T173M, T173L, V175M, K176R, K176Q, H177S, H177R, R178Q, K180E, K180N, K181T, K181V, E183A, E183Q, A201S, K203Q, K203R, R212K, R212N, R212G, R212M, V214I, G218K, G218A, Q220E, Q220D, K227R, K2275, K227E, N239K, N239S, N239H, R239C, Q241P, E242D, E242N, V244I, S245N, S245R, K250N, K250D, K250R, K250G, K250N, K250Q, N252S, S253G, S253L, V254T, V254I, D256N, Q258R, Y261F, K262D, K262E, K262L, K262R, K262Q, T264S, E266S, E267K, E267Q, E267K, D270N, D270E, V271I, S282E, R285T, F287I, S290N, K291R, V294I, T295S, T295Q, L296V, L296P, L296S, R297K, K299R, T300K, T300A, S302G, S302A, S302V, S302T, K303N, K303S, K303R, R304H, R304S, S305P, S305T, and S305A. In some embodiments, the C-terminal tail is a sequence from mouse or rat D1L3 (See FIG. 2).

In some embodiments, the building block substitutions to D1L3 are selected from human D1 and result in variants of human D1L3 which feature one or more of the following mutations: M1_E4delinsMRGMKL, A6_P7delinsGA, L10A, L12_S17delinsAALLQG, L19_R22delinsVSLK, C24_S25delinsAA, V28_S30delinsIQT, S34T, Q36_V44delinsMSNATLVSY, K47_K50delinsQILS, C52Y, I55A, M58Q, I60_K61delinsVR, N64_I70delinsHLTAVGK, M72_K74delinsLDN, R77_I83delinsQDAPD, N86H, I89V, S91_R92delinsEP, T97S, Q101R, A103L, L105V, K107_L110delinsRPDQ, V113_R115delinsAVD, H118Y, H120D, Y122_A127delinsGCEPCGN, V129T, S131N, F135_V136delinsAI, W138R, Q140F, P142_H143delinsRF, A145E, K147_D148delinsRE, V150A, I152V, T156_T157delinsAA, E159_S161delinsGDA, K163A, E167A, V169_E170delinsYD, T173L, K176_R178delinsQEK, K180_A181delinsGL, N183_F186delinsDVML, P198_A201delinsRPSQ, K203_N204delinsSS, R208W, D210S, R212T, V214Q, G218P, Q220_E221delinsSA, V225_S228delinsATP, N230H, L238_R239delinsVA, Q241_S246delinsMLLRGA, K250D, N252_V254delinsALP, D256N, K259A, K262G, T264_E267delinsSDQL, L269_V271delinsQAI, F275Y, F279_K280delinsVM, and Q282_S205delinsK.

In some embodiments, the building block substitutions to D1L3 are selected from human D1L1 and result in variants of human D1L3 which feature one or more of the following mutations: S2_L5delinsHYPT, P7_L9delinsL, L11F, L13_S17delinsILANG, L19delinsQ, M21F, S25A, V28_S34delinsAQRLTLA, Q36_A41delinsVAREQV, V44_I45delinsTL, K47_K50delinsRILA, I55_M58delinsMVLQ, I60_K61delinsVV, N6_C68delinsSGSAI, I70L, M72_L74delinsLRE, N78_R81delinsFDGS, I83_T84delinsP, N86_I89delinsSTLS, S91_R92delinsPQ, N96S, K99M, Q101T, A103_L105delinsVYF, K107_S112delinsRSHKTQ, K114_R115delinsLS, H118V, H120N, Y122_A127delinsED, S131A, V137_W138delinsAQ, Q140_S141delinsSL, H143_F149delinsSNVLPSL, I151_I152delinsLV, E159_V162delinsKAVE, I165_A167delinsLNA, V169_E170delinsYD, Y172_D174delinsFLE, K176_R178delinsSQH, K180_F184delinsQSKDV, G193D, S195_P198delinsASLT, A201_R206delinsRLDKLE, D210E, R212G, V214H, L216V, G218A, Q220G, K226_K227delinsRA, N230H, A232T, I236V, R239H, Q246_V249delinsERCR, S246_V254delinsLLHTAAA, Q258_K262delinsPTSFQ, D270_V271delinsNI, F275Y, F279_K280delinsVE, Q282_S283delinsKL, R285Q, F287_K292delinsHSVQPL, V294L, and L296_S205delinsVLLLLSLLSPQLCPAA.

In some embodiments, the building block substitutions to D1L3 are selected from human D1L2 and result in variants of human D1L3 which feature one or more of the following mutations: S2_L5delinsGGPR, P7L, L9delinsAA, L11_L12delinsWA, S14_L19delinsEAAGTA, M21L, C24_S25delinsGA, V28_R29delinsIQ, E33D, Q36_E37delinsVS, K39_V44delinsPACGSI, A47V, V48_C52delinsILAGY, I54_I55delinsLA, M58Q, 160_K61delinsVR, S63_I70delinsPDLSAVSA, K74_L75delinsQI, XX (deletion in Donor), R80_T84delinsVSEHE, N86_Y87delinsSF, 189S, S91_R92delinsQP, N96_T97delinsDQ, Q101M, A103L, L105V, K107_L110delinsRKDA, K114_S116delinsVDT, H118L, H120P, Y122_A127delinsPE, W138K, Q140_S141delinsSA, H143G, T144_A145insGERAPPLPSRRALTPPPLPA, V146_F149delinsAQNL, I151L, T156_T157delinsAA, E159_S161delinsHQA, K163A, E162A, V169_E170delinsYD, T173L, K176_R178delinsIDK, K180_I185delinsGTDDML, M187L, G193D, P198_A201delinsRAQD, K203_N204delinsAA, T209_R212delinsSSEV, V214K, G218P, Q220_E221delinsSA, K226_K227delinsGN, T229_N230delinsD, L238_R239delinsAC, Q241_S245delinsARLRR, V247_V248delinsLK, K250Q, N252_S253delinsAT, F255H, K259_K262delinsEEFG, T264_E267delinsDQTQ, D270_V271delinsAI, F279_K280delinsVT, Q282_S284delinsKFH, and A286_S305del.

In certain embodiments, the D1L3 protein variant contains one or more amino acid substitutions, additions, or deletions in the C-terminal tail amino acid sequence defined by SEQ ID NO: 10. The C-terminal tail domain or a portion thereof may be deleted. In some embodiments, at least 3, 5, 8, 10, 12, 15, 18, or 23 amino acids of the C-terminal tail domain are deleted. In some embodiments, such amino acid substitutions and/or deletions in the C-terminal tail (including building block substitutions of the C-terminal tail as disclosed above) reduce proteolysis in the C-terminal tail. In some embodiments, such substitutions can be made according to non-human D1L3 variants as described above, which may avoid one or more paired basic amino acid sites that are subject to protease cleavage.

In certain embodiments, the D1L3 protein variant contains one or more, e.g., 1, 2, 3, 4, 5, or more amino acid substitutions, additions, or deletions in the internal sequence defined by SEQ ID NO: 11 (which is absent from isoform 2), and which is optionally deleted in whole or in part.

In various embodiments, the D1L3 variant evaluated in accordance with the disclosure comprises the D1L3 wild-type amino acid sequence or a variant sequence described herein, fused to the C-terminus of a carrier protein, with a linking amino acid sequence. In some embodiments, the carrier protein is Fc fragment or albumin. In some embodiments, the carrier protein is human albumin. The linking sequence can be a flexible linker predominately composed of Gly, or Gy and Ser. In some embodiments, the linker is composed of Gly and amino acids having hydrophilic side chains (e.g., Ser, Thr). In some embodiments, the linker is from 5 to 20 amino acids. An exemplary linker has the structure $(GGGGS)_3$.

The peptide linker may be a flexible linker, a rigid linker, or in some embodiments a physiologically-cleavable linker (e.g., a protease-cleavable linker). In some embodiments, the linker is 5 to 100 amino acids in length, or is 5 to 50 amino acids in length.

Linkers, where present, can be selected from flexible, rigid, and cleavable peptide linkers. Flexible linkers are predominately or entirely composed of small, non-polar or polar residues such as Gly, Ser and Thr. An exemplary flexible linker comprises $(Gly_ySer)n$ linkers, where y is from 1 to 10 (e.g., from 1 to 5), and n is from 1 to about 10, and in some embodiments, is from 3 to about 6. In exemplary embodiments, y is from 2 to 4, and n is from 3 to 8. Due to their flexibility, these linkers are unstructured. More rigid linkers include polyproline or poly Pro-Ala motifs and α-helical linkers. An exemplary α-helical linker is A(EAAAK)$_n$A, where n is as defined above (e.g., from 1 to 10, or 2 to 6). Generally, linkers can be predominately composed of amino acids selected from Gly, Ser, Thr, Ala, and Pro. Exemplary linker sequences contain at least 10 amino acids, and may be in the range of 15 to 35 amino acids. Exemplary linker designs are provided as SEQ ID NOS: 41 to 51.

In some embodiments, the variant comprises a linker, wherein the amino acid sequence of the linker is predominately glycine and serine residues, or consists essentially of glycine and serine residues. In some embodiments, the ratio of Ser and Gly in the linker is, respectively, from about 1:1 to about 1:10, from about 1:2 to about 1:6, or about 1:4. Exemplary linker sequences comprise S(GGS)$_4$GSS (SEQ ID NO: 46), S(GGS)$_9$GS (SEQ ID NO: 47), (GGS)$_9$GS (SEQ ID NO: 48). In some embodiments, the linker has at least 10 amino acids, or at least 15 amino acids, or at least 20 amino acids, or at least 25 amino acids. For example, the linker may have a length of from 15 to 30 amino acids. In various embodiments, longer linkers of at least 15 amino acids can provide improvements in yield upon expression in *Pichia pastoris*. Further, longer linker sequences showed improved chromatin-degrading activity, as compared to shorter linker sequences.

In other embodiments, the linker is a physiologically-cleavable linker, such as a protease-cleavable linker. For example, the protease may be a coagulation pathway protease, such as activated Factor XII. In certain embodiments, the linker comprises the amino acid sequence of Factor XI (SEQ ID NO: 49) and/or prekallikrein (SEQ ID NO: 50 or 51) or a physiologically cleavable fragment thereof. In other embodiments, the linker includes a peptide sequence that is targeted for cleavage by a neutrophil specific protease, such as neutrophil elastase, cathepsin G, and proteinase 3.

In some embodiments, the DNASE1-LIKE 3 Isoform 2 (D1L3-2) variant evaluated and selected for use in therapy in accordance with embodiments of the invention comprise an amino acid sequence that is at least 80% identical to the enzyme defined by SEQ ID NO: 5, with one or more building block substitutions.

In some embodiments, the building block substitutions to D1L3-2 are selected from non-human D1L3 proteins and result in variants of human D1L3-2 which feature one or more of the following mutations: M21L, K22R, I22L, I22V, E33A, E33Y, E33G, S34A, S34T, Q36K, Q36R, E37A, E37Q, D48N, K39Q, K39H, K39R, K39C, N40E, N40Q, N40K, A41V, V44I, V53I, I53L, I54M, V57L, I60V, N64S, H64S, R66N, R66M, I70V, I70M, I70T, M72L, E73K, K74R, R77G, V81L, S82T, R85T, R85A, R85K, R85D, R85Q, S86K, S86N, S86Y, H88L, H88V, Y89F, H90G, Y92N, Q93E, D94A, D94S, D94N, G95E, A97V, A97T, V99A, F105Y, V107T, Q110H, S111A, H113F, H113Y, V116A, I122V, T127S, T130A, V132I, K133R, V139A, E140D, T143M, T143L, V145M, K146R, K146Q, H147S, H147R, R148Q, K150E, K150N, K151T, K151V, E153A, E153Q, A171S, K173Q, K173R, R182K, R182N, R182G, R182M, V184I, G188K, G188A, Q190E, Q190D, K197R, K197S, K197E, N209K, N209S, N209H, R209C, Q211P, E212D, E212N, V214I, S215N, S215R, K220R, K220D, K220P, K220G, K220N, K220Q, N222S, S223G, S223L, V224T, V224I, D226N, Q228R, Y231F, K232D, K232E, K232L, K232R, K232Q, T234S, E236S, E237K, E237Q, E237K, D240N, D240E, V241I, S252E, R255T, F257I, S260N, K261R, V264I, T265S, T265Q, L266V, L266P, L266S, R267K, K269R, T270K, T270A, S272G, S272A, S272V, S272T, K273N, K273S, K273R, R274H, R274S, S275P, S275T, and S275A.

In some embodiments, the building block substitutions to D1L3-2 are selected from human D1 and result in variants of human D1L3-2 which feature one or more of the following mutations: M1_E4delinsMRGMKLL, A6_P7delinsGA, L10A, L12_S17delinsAALLQG, L19_R22delinsVSLK, C24_S25delinsAA, V28_S30delinsIQT, S34T, Q36_V44delinsMSNATLVSY, K152_K156delinsGDAVA, C52Y, I55A, M58Q, I60_K61delinsVR, N64_I70delinsHLTAVGK, M72_K74delinsLDN, N76_R77in5QDAPDTYHYVVSEPLGRNSYKERYLFVY, E78_L80delinsPDQ, V83_R85delinsAVD, H88Y, H90D, Y92_A97delinsGCEPCGN, V99T, S101N, F105_V106delinsAI, W108R, Q110F, P112_H113delinsRF, A115E, K117_D118delinsRE, V120A, I122V, T126_T127delinsAA, E129_T131delinsGDA, K133A, V139_E140delinsYD, T143L, K146_R148delinsQEK, K150_A151delinsGL, N153_F156delinsDVML, P168_A171delinsRPSQ, K173_N1174delinsSS, R178W, D180S, R182T, V184Q, G188P, Q190_E191delinsSA, V195_S199delinsATP, N200H, L208_R209delinsVA, Q211_S216delinsMLLRGA, K220D, N222_V224delinsALP, D226N, K232G, T234_E237delinsSDQL, L239_V241delinsQAI, F245Y, F249_K250delinsVM, and Q252_S275delinsK.

In some embodiments, the building block substitutions to D1L3-2 are selected from human D1L1 and result in variants of human D1L3-2 which feature one or more of the following mutations: S2_L5delinsHYPT, P7_L9delinsA, L11F, L13_S17delinsILANG, L19delinsQ, M21F, S25A, V28_S34delinsAQRLTLA, Q36_A41delinsVAREQV, V44_I45delinsTL, K47_K50delinsRILA, I55_M58delinsMVLQ, I60_K61delinsVV, N6_C68delinsSGSAI, I70L, M72_L74delinsLRE, N76_R77insRFDGSGPYSTLSSPQLGRSTYME TYVYFYRSHKTQ, E78_S82delinsSHKTQ, K84_R85delinsLS, H88V, H90N, Y92_A97delinsED, S101A, V107_W108delinsAQ, Q110_S111delinsSL, H113_F119delinsSNVLPSL, I121_I122delinsLV, E129_V132delinsKAVE, I135_A137delinsLNA, V139_E140delinsYD, Y142_D144delinsFLE, K146_R148delinsSQH, K150_F154delinsQSKDV, G163D, S165_P168delinsASLT, A171_R176delinsRLDKLE, D180E, R182G, V184H, L186V, G188A, Q190G, K196_K227delinsRA, N200H, A192T, I206V, R209H, Q216_V219delinsERCR, S216_V224delinsLLHTAAA, Q228_K232delinsPTSFQ, D240_V241delinsN, F245Y, F249_K250delinsVE, Q252_S253delinsKL, R255Q, F257_K262delinsHSVQPL, V264L, and L266_S275delinsVLLLLSLLSPQLCPAA.

In some embodiments, the building block substitutions to D1L3-2 are selected from human D1L2 and result in variants of human D1L3-2 which feature one or more of the following mutations: S2_L5delinsGGPR, P7L, L9delinsAA, LL11_L12delinsWA, S14_L19delinsEAAGTA, M21L, C24_S25delinsGA, V28_R29delinsIQ, E33D, Q36_E37delinsVS, K39_V44delinsPACGSI, A47V, V48_C52delinsILAGY, I54_I55delinsLA, M58Q, I60_K61delinsVR, S63_I70delinsPDLSAVSA, K74_L75delinsQI, E78_L80delinsKDA, K84_S86delinsVDT, H88L, H90P, Y92_A97delinsPE, W108K, Q110_S111delinsSA, H113G, T114_A115insGERAPPLPSRRALTPPPLPA, V116_F119delinsAQNL, I121T, T126_T127delinsAA, E129_S141delinsHQA, K133A, E132A, V139_E140delinsYD, T143L, K146_R148delinsIDK, K150_I155delinsGTDDML, M157L, G163D, P168_A171delinsRAQD, K173_N174delinsAA, T179_R182delinsSSEV, V184K, G188P, Q190_E191delinsSA, K196_K197delinsGN, T199_N200delinsD, L208_R209delinsAC, Q211_S215delinsARLRR, V217_V218delinsLK, K220Q, N222_S223delinsAT, F225H, K229_K242delinsEEFG, T234_E237delinsDQTQ, D240_V241delinsAI, F249_K250delinsVT, and Q252_S254delinsKFH, A256_S275del.

In certain embodiments, the D1L3-2 protein variant contains one or more amino acid substitutions, additions, or deletions in the C-terminal tail domain defined by SEQ ID NO: 11. The C-terminal tail domain or a portion thereof may be deleted. In some embodiments, at least 3, 5, 8, 10, 12, 15, 18, or 23 amino acids of the C-terminal tail domain are deleted.

In various embodiments, the D1L3-2 variant evaluated in accordance with the disclosure comprises the D1L3-2 wild-type amino acid sequence or a variant sequence described herein, fused to the C-terminus of a carrier protein, with a linking amino acid sequence. In some embodiments, the carrier protein is Fc fragment or albumin. In some embodiments, the carrier protein is human albumin. The linking sequence can be a flexible linker predominately composed of Gly, or Gy and Ser. In some embodiments, the linker is composed of Gly and amino acids having hydrophilic side chains (e.g., Ser, Thr). In some embodiments, the linker is from 5 to 20 amino acids. An exemplary linker has the structure (GGGGS)$_3$.

The peptide linker may be a flexible linker, a rigid linker, or in some embodiments a physiologically-cleavable linker (e.g., a protease-cleavable linker). In some embodiments, the linker is 5 to 100 amino acids in length, or is 5 to 50 amino acids in length.

Linkers, where present, can be selected from flexible, rigid, and cleavable peptide linkers. Flexible linkers are predominately or entirely composed of small, non-polar or polar residues such as Gly, Ser and Thr. An exemplary flexible linker comprises (Gly$_y$Ser)$_n$ linkers, where y is from 1 to 10 (e.g., from 1 to 5), and n is from 1 to about 10, and in some embodiments, is from 3 to about 6. In exemplary embodiments, y is from 2 to 4, and n is from 3 to 8. Due to their flexibility, these linkers are unstructured. More rigid linkers include polyproline or poly Pro-Ala motifs and α-helical linkers. An exemplary α-helical linker is A(EAAAK)$_n$A, where n is as defined above (e.g., from 1 to 10, or 2 to 6). Generally, linkers can be predominately composed of amino acids selected from Gly, Ser, Thr, Ala, and Pro. Exemplary linker sequences contain at least 10 amino acids, and may be in the range of 15 to 35 amino acids. Exemplary linker designs are provided as SEQ ID NOS: 41 to 51.

In some embodiments, the variant comprises a linker, wherein the amino acid sequence of the linker is predominately glycine and serine residues, or consists essentially of glycine and serine residues. In some embodiments, the ratio of Ser and Gly in the linker is, respectively, from about 1:1 to about 1:10, from about 1:2 to about 1:6, or about 1:4. Exemplary linker sequences comprise S(GGS)$_4$GSS (SEQ ID NO: 46), S(GGS)$_9$GS (SEQ ID NO: 47), (GGS)$_9$GS (SEQ ID NO: 48). In some embodiments, the linker has at least 10 amino acids, or at least 15 amino acids, or at least 20 amino acids, or at least 25 amino acids. For example, the linker may have a length of from 15 to 30 amino acids. In various embodiments, longer linkers of at least 15 amino acids can provide improvements in yield upon expression in *Pichia pastoris*, and may provide for improved chromatin degrading activity.

In other embodiments, the linker is a physiologically-cleavable linker, such as a protease-cleavable linker. For example, the protease may be a coagulation pathway protease, such as activated Factor XII. In certain embodiments, the linker comprises the amino acid sequence of Factor XI (SEQ ID NO: 49) and/or prekallikrein (SEQ ID NO: 50 or 51) or a physiologically cleavable fragment thereof. In other embodiments, the linker includes a peptide sequence that is targeted for cleavage by a neutrophil specific protease, such as neutrophil elastase, cathepsin G, and proteinase 3.

In various embodiments, the DNASE2A (D2A) variant evaluated and selected for use in therapy in accordance with embodiments of the invention comprise an amino acid sequence that is at least 80% identical to the enzyme defined by SEQ ID NO: 6, with one or more building block substitutions.

In some embodiments, the building block substitutions to DNASE2A are selected from non-human D2A proteins and result in variants of human D2A, which feature one or more of the following mutations: Q25R, L38H, L38N, R39S, R39T, G40S, G42R, E43D, A44T, A44K, A44V, A45P, A45T, R47K, R47N, R47S, Q50T, Q50M, Q50R, L54M, L54F, E56Q, S57N, S57H, S57E, G59D, G59E, G60D, R62Q, R62S, R65V, R65A, A66G, L67Y, L67H, L67F, L67S, N69D, P71S, P71K, P71T, E72D, E72T, V75L, R77L, Q80L, R84Q, S85K, S85N, T87S, T87N, L93V, Q101K, P102S, P102Y, S103R, K104S, K104E, K104G, A105S, Q106R, Q106K, D107H, S109T, M110G, M110S, M110N, R111H, H122Q, D123E, V129I, N134R, P137S, P138R, A139S, A142G, A143V, S145T, H148P, S149N, S149G, C151Q, C151R, T152K, Y153F, L158I, F162L, F164L, A165T, A165S, S168A, S168P, S168L, K169R, K169G, K169D, K169N, M170I, G171S, K172R, W180L, W180M, N183D, Y184H, Q185K, Q185R, I180F, I180D, Q192R, E193K, F194L, D196Y, N199T, N199E, V201I, V201T, G203N, G203Q, S207L, S207R, Q208H, Q208R, E209G, I215V, T216I, Q220R, Q220K, A221K, A223T, V224T, V224S, F231C, S232G, K233N, A244S, A245E, T249S, N250T, H257Q, H257P, T259S, V260P, V260S, V260A, D269G, I270A, I270T, 1270V, W271Y, W271H, W271Q, Q272K, Q272H, V273I, L274F, N275D, N277T, Q278E, I279I, A280G, A285S, G286R, P287L, S288T, S288A, S288N, N290S, S291A, S301A, S301T, K303Q, K303E, G304R, I307A, I307V, Q316K, G317A, G317R, E319T, Q320H, L326V, A328T, L330V, L330M, A332S, L333F, Q338R, Q338K, P339S, N343D, N343A, Y344W, Y344C, Q345K, and Q345E.

In some embodiments, the building block substitutions to D2A are selected from human DNASE2B (D2B) and result in variants of human D2A, which feature one or more of the following mutations: 12 L6delinsKQKMM, A8R, C11_P13delinsRTSFALLFLGLFGVLG, G15 T18delinsATIS, Y20 S23delinsRNEE, Q25_P26delinsKA, V31_V32delinsTF, A37_L38delinsK, G40_G42delinsQNK, A44_R47delinsSGET, Q50E, K52L, E56_G60delinsSTIRS, D62_A66delinsKSEQ, I68M, S70_V75delinsDTKSVL, S78T, P81Q, R84delinsEAYA, N86_L90delinsKSNNT, F92Y, L94I, Q108_P109delinsGV, Q101K, S103_D107delinsVNK, V117L, L120_G124delinsWNRVQ, V129I, V132I, N134Q, P136del, A139_A143delinsIPEEG, S145_W146delinsDY, H148_Y153delinsPTGRRN, T156_L158delinsSGI, V160_S161delinsIT, P163_A165delinsKYN, F167_K172delinsYEAIDS, T175_Y178delinsLVCN, W180N, N183_I89delinsSCSIPAT, A192H, F194_V194delinsLIHMPQLCTRASS, Q208_E209delinsEI, W211_I215delinsGRLLT, T218Q, Q220_A221delnsAQ, A223_V224delinsQK, Q226_S227delinsLH, F231_K233delinsSDS, G235L, L238_G241delinsIFAA, L243M, A245_A246delinsQR, G248K, N250H, Q252_F255delinsLTET, H257_I262delinsQRKRQE, D269_Q272delinsLPYH, L274Y, Y276_Q278delinsIKA, A280_S288delinsKLSRHSY, N290S, T292_E293delinsYQ, S296A, V300I, P302Q, P305delinsTKNR, V309I, M312L, N315_Q320deinsSPHQAF, G322S, T325_L326delinsFI, L330_K335delinsNWQIYQ, P339G, K342_N343delinsLY, Q345_P346delinsES, and N348_I360delinsK.

In various embodiments, the D2A variant evaluated in accordance with the disclosure comprises the D2A wildtype amino acid sequence or a variant sequence described herein, fused to the C-terminus of a carrier protein, with a linking amino acid sequence. In some embodiments, the carrier protein is Fc fragment or albumin. In some embodiments, the carrier protein is human albumin. The linking sequence can be a flexible linker predominately composed of Gly, or Gy and Ser. In some embodiments, the linker is composed of Gly and amino acids having hydrophilic side chains (e.g., Ser, Thr). In some embodiments, the linker is from 5 to 20 amino acids. An exemplary linker has the structure $(GGGGS)_3$.

The peptide linker may be a flexible linker, a rigid linker, or in some embodiments a physiologically-cleavable linker (e.g., a protease-cleavable linker). In some embodiments, the linker is 5 to 100 amino acids in length, or is 5 to 50 amino acids in length.

Linkers, where present, can be selected from flexible, rigid, and cleavable peptide linkers. Flexible linkers are predominately or entirely composed of small, non-polar or polar residues such as Gly, Ser and Thr. An exemplary flexible linker comprises $(Gly_y Ser)n$ linkers, where y is from 1 to 10 (e.g., from 1 to 5), and n is from 1 to about 10, and in some embodiments, is from 3 to about 6. In exemplary embodiments, y is from 2 to 4, and n is from 3 to 8. Due to their flexibility, these linkers are unstructured. More rigid linkers include polyproline or poly Pro-Ala motifs and α-helical linkers. An exemplary α-helical linker is $A(EAAAK)_nA$, where n is as defined above (e.g., from 1 to 10, or 2 to 6). Generally, linkers can be predominately composed of amino acids selected from Gly, Ser, Thr, Ala, and Pro. Exemplary linker sequences contain at least 10 amino acids, and may be in the range of 15 to 35 amino acids. Exemplary linker designs are provided as SEQ ID NOS: 41 to 51.

In some embodiments, the variant comprises a linker, wherein the amino acid sequence of the linker is predominately glycine and serine residues, or consists essentially of glycine and serine residues. In some embodiments, the ratio of Ser and Gly in the linker is, respectively, from about 1:1 to about 1:10, from about 1:2 to about 1:6, or about 1:4. Exemplary linker sequences comprise $S(GGS)_4GSS$ (SEQ ID NO: 46), $S(GGS)_9GS$ (SEQ ID NO: 47), $(GGS)_9GS$ (SEQ ID NO: 48). In some embodiments, the linker has at least 10 amino acids, or at least 15 amino acids, or at least 20 amino acids, or at least 25 amino acids. For example, the linker may have a length of from 15 to 30 amino acids. In various embodiments, longer linkers of at least 15 amino acids can provide improvements in yield upon expression in *Pichia pastoris*.

In other embodiments, the linker is a physiologically-cleavable linker, such as a protease-cleavable linker. For example, the protease may be a coagulation pathway protease, such as activated Factor XII. In certain embodiments, the linker comprises the amino acid sequence of Factor XI (SEQ ID NO: 49) and/or prekallikrein (SEQ ID NO: 50 or 51) or a physiologically cleavable fragment thereof. In other embodiments, the linker includes a peptide sequence that is targeted for cleavage by a neutrophil specific protease, such as neutrophil elastase, cathepsin G, and proteinase 3.

In some embodiments, the DNASE2B (D2B) variant evaluated and selected for therapy in accordance with embodiments of this disclosure comprise an amino acid sequence that is at least 80% identical to the enzyme defined by SEQ ID NO: 7, with one or more building block substitutions.

In some embodiments, the building block substitutions to D2B are selected from non-human D2B proteins and result in variants of human D2B, which feature one or more of the following mutations: A28P, A28T, T29E, T29V, T29K, S31A, R33I, N34S, E36Y, E36D, A37P, T44I, T44A, T44V, K50R, R51Q, R51K, Q52T, N53S, N53D, N53E, K54R, E55A, E55G, S56G, G57E, G57T, G57R, T59A, T59M, E62Q, E62D, E62G, T70R, T70M, T70I, R71Q, S72T, R74N, R74S, R74K, K75R, E77L, E77H, E77K, Q78Y, Q78H, Q78L, M80I, M80V, D82T, D82S, D82A, T83S, K84R, K84D, V86A, V86S, Q92E, Q93H, E96D, A97T, Y98H, Y98N, Y98C, A99D, A99H, S100A, SF, K101E, S102T, S102N, S102D,N104D,N104S, L108V, I109L, G113A, V114I, K116G, K116A, P117S, V118A, N119T, N119G, N119S, Y120C, R122G, K123Q, K123N, Y124F, T127A, L132V, V136T, V136I, I145V, Q147K, Q147R, I151V, I151T, E154H, E154K, D157E, P160T, P160S, T161S, R164Q, N165Y, N165H, G166A, S168T, S168A, S168N, I170L, I170M, F174L, K175G, K175R, N178S, Y179F, A181E, A181T, S184F, V188I, C189L, C189F, C189Y, N190Q, V192I, S195R, S197F, A200S, A200N, A200T, T201I, T201A, H203R, Q204W, Q204M, E205K, 1207V, 1207F, H208Y, H208Y, M209L, Q211R, L212M, T214A, R215K, R215G, A216S, S217T, S217H, S218A, S219L, E220K, G223V, G223S, R224Q, L225Y, L225R, L225H, T227A, T228E, T228V, T228S, Q230H, Q233R, Q235L, K236N, K236S, L238V, L238I, S243F, D244S, D244T, S245F, F246Y, L247T, L247H, A252T, A252V, A253G, M255I, R258K, R258H, R258Q, T261V, T265A, T265V, E266Q, T267S, R270K, R272K, R272N, R272G, Q273H, Y283H, C285I, I288V, A290S, K292G, K292R, L293V, L293G, L293I, R295G, R295S, R295L, R295H, H296K, H296Q, Y298D, S300P, Y302R, Y302H, Q303H, A306S, I310V, Q312I, Q312T, Q312R, Q312L, G314D, G314R, T315S, K316A, K316Q, N317A, R318H, P329L, H330Y, F333L, F333S, S335G, T341S, T341N, Q342K, W344H, W344R, W344Q, Q345H, Q345Y, Q345R, Q345N, Q349H, Q351H, Q351D, Q351E, G352K, G352R, V354Y, L355S, Y356R, Y356H, Y357H, E358G, E358A, S359F, S359N, S359D, and K361N.

In others embodiments, the building block substitutions to D2B are selected from human DNASE2A (D2A) and result in variants of human D2B, which feature one or more of the following mutations: K2_M6delinsIPLLL, R8A, R11_G21delinsCVP, A28_S31delinsGALT, R33_E36delinsYGDS, K38_A39delinsQP, T44_F45delinsVV, K50delinsAL, Q52_K54delinsGSG, S56_T59delinsAAQR, E62Q, L64K, S70_S72delinsESSGG, K75_Q78delinsDGRA, M80I, D82_K87delinsSPEGAV, T90S, Q93P, E96_Y99delinsR, K101_T105delinsNTSQL, Y107F, I109L, G113_V114delinsQP, K106Q, V118_Y120delinsSKAQD, L130V, W133_Q137delinsLDHDG, I142V, I145V, Q147N, F148_P149insP, I15I_G155delinsASSAA, D157 Y158delinsSW, P160_N165delinsHSACTY, S168_I170delinsTLL, I172_T173delinsVS, K175_N177delinsPFA, Y179_s184delinsFSKMGK, L187_N190delinsTYTY, N192W, S195_T201delinsNYQLEGI, H203A, L206_S218delinsFPDLENVVKGHHV, E220_I221delinsQE, G223_T227delinsWNSSI, A232_Q233delinsQA, Q236_K236delinsAV, L238_H239delinsQS, S243_S2456delinsFSK, L247G, 1250_A253delinsLYSG, M255L, Q257_R258delinsAA, K260G, H262N, L264_T267delinsQVQF, Q269_E274delinsHKTVGI, L281_Y284delinsDIWQ, Y286L, 1288_A290delinsVNQ, K292_Y298delinsAFPGAGPS, S300N, Y302_Q303delinsTE, A306S, 1310V, Q312P, T315_R318delinsP, I322V, L325M, S328_F333delinsNQGEEQ, S335G, F338 I339delinsTL, N343_Q348delinsLPALWK, G353P, L355_Y356delinsKN, E358_S359delinsQP, and K361 delinsNG-MARKPSRAYKI.

In various embodiments, the D2B variant evaluated in accordance with the disclosure comprises the D2B wildtype amino acid sequence or a variant sequence described herein, fused to the C-terminus of a carrier protein, with a linking amino acid sequence. In some embodiments, the carrier protein is Fc fragment or albumin. In some embodiments, the carrier protein is human albumin. The linking sequence can be a flexible linker predominately composed of Gly, or Gy and Ser. In some embodiments, the linker is composed of Gly and amino acids having hydrophilic side chains (e.g., Ser, Thr). In some embodiments, the linker is from 5 to 20 amino acids. An exemplary linker has the structure (GGGGS)$_3$.

The peptide linker may be a flexible linker, a rigid linker, or in some embodiments a physiologically-cleavable linker (e.g., a protease-cleavable linker). In some embodiments, the linker is 5 to 100 amino acids in length, or is 5 to 50 amino acids in length.

Linkers, where present, can be selected from flexible, rigid, and cleavable peptide linkers. Flexible linkers are predominately or entirely composed of small, non-polar or polar residues such as Gly, Ser and Thr. An exemplary flexible linker comprises $(Gly_ySer)_n$ linkers, where y is from 1 to 10 (e.g., from 1 to 5), and n is from 1 to about 10, and in some embodiments, is from 3 to about 6. In exemplary embodiments, y is from 2 to 4, and n is from 3 to 8. Due to their flexibility, these linkers are unstructured. More rigid linkers include polyproline or poly Pro-Ala motifs and α-helical linkers. An exemplary α-helical linker is $A(EAAAK)_nA$, where n is as defined above (e.g., from 1 to 10, or 2 to 6). Generally, linkers can be predominately composed of amino acids selected from Gly, Ser, Thr, Ala, and Pro. Exemplary linker sequences contain at least 10 amino acids, and may be in the range of 15 to 35 amino acids. Exemplary linker designs are provided as SEQ ID NOS: 41 to 51.

In some embodiments, the variant comprises a linker, wherein the amino acid sequence of the linker is predominately glycine and serine residues, or consists essentially of glycine and serine residues. In some embodiments, the ratio of Ser and Gly in the linker is, respectively, from about 1:1 to about 1:10, from about 1:2 to about 1:6, or about 1:4. Exemplary linker sequences comprise $S(GGS)_4GSS$ (SEQ ID NO: 46), $S(GGS)_9GS$ (SEQ ID NO: 47), $(GGS)_9GS$ (SEQ ID NO: 48). In some embodiments, the linker has at least 10 amino acids, or at least 15 amino acids, or at least 20 amino acids, or at least 25 amino acids. For example, the linker may have a length of from 15 to 30 amino acids. In various embodiments, longer linkers of at least 15 amino acids can provide improvements in yield upon expression in *Pichia pastoris*.

In other embodiments, the linker is a physiologically-cleavable linker, such as a protease-cleavable linker. For example, the protease may be a coagulation pathway protease, such as activated Factor XII. In certain embodiments, the linker comprises the amino acid sequence of Factor XI (SEQ ID NO: 49) and/or prekallikrein (SEQ ID NO: 50 or 51) or a physiologically cleavable fragment thereof. In other embodiments, the linker includes a peptide sequence that is targeted for cleavage by a neutrophil specific protease, such as neutrophil elastase, cathepsin G, and proteinase 3.

In some embodiments, the DNase variant (e.g., a variant of DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), DNASE2A (D2A), and DNASE2B (D2B)) comprises an N-terminal or C-terminal fusion to a half-life extending moiety, such as albumin, transferrin, an Fc, or elastin-like protein. See U.S. Pat. No. 9,458,218, which is hereby incorporated by reference in its entirety. In some embodiments, the DNase variant is dimerized by an immunoglobulin hinge region. For example, the engineered enzymes described herein may also include an Fc-fusion domain (e.g. a hinge and CH2 domains and CH3 domains of an immunoglobulin). In other cases, the engineered DNase variant is fused to albumin, e.g., human albumin (SEQ ID NO: 12) or a fragment thereof. See WO 2015/066550; U.S. Pat. No. 9,221,896, which are hereby incorporated by reference in its entirety. Albumin can be fused at the N-terminus or the C-terminus of the engineered DNase variant, and may optionally comprise an amino acid linker. In some embodiments, two DNase variants are dimerized by an Fc hinge region, creating a dimeric molecule with synergistic functional properties for degrading NETs.

In some embodiments, human albumin and a flexible linker is fused to the N-terminus of DNASE1 (e.g., SEQ ID NO: 13), DNASE1-LIKE 1 (e.g., SEQ ID NO: 14), DNASE1-LIKE 2 (e.g., SEQ ID NO: 15), DNASE1-LIKE 3 Isoform 1 (e.g., SEQ ID NO: 16), DNASE1-LIKE 3 Isoform 2 (e.g., SEQ ID NO: 17), DNASE2A (e.g., SEQ ID NO: 18), and DNASE2B (e.g., SEQ ID NO: 19).

In some embodiments, the recombinant DNase variant comprises one or more polyethylene glycol (PEG) moieties, which may be conjugated at one or more of positions or the C-terminus. In some embodiments, the native amino acid at that position is substituted with an amino acid having a side chain suitable for crosslinking with hydrophilic moieties, to facilitate linkage of the hydrophilic moiety to the peptide. In other embodiments, an amino acid modified to comprise a hydrophilic group is added to the peptide at the C-terminus. The PEG chain(s) may have a molecular weight in the range of about 500 to about 40,000 Daltons. In some embodiments, the PEG chain(s) have a molecular weight in the range of about 500 to about 5,000 Daltons. In some embodiments, the PEG chain(s) have a molecular weight of about 10,000 to about 20,000 Daltons.

The extracellular DNase variants can be screened in assays for altered properties, including altered pH and temperature optimum, requirement for divalent cations for enzymatic activity, mechanisms of enzymatic inhibition (e.g. salt, divalent cations, actin, heparin, proteases), substrate affinity and specificity (e.g. single-stranded DNA, double-stranded DNA, chromatin, NETs, plasmid DNA, mitochondrial DNA), localization upon secretion (e.g. membrane-bound, extracellular matrix), localization signals (e.g. nuclear localization signal, membrane anchor), glycosylation sites, disulfide-bonds and unpaired cysteines, compatibility with GMP-compliant in vitro expression systems (e.g. bacteria. yeast, mammalian cells), compatibility with carriers (e.g. PEGylation, Fc fragment, albumin), compatibility with GMP-compliant purification methods (e.g. anion exchange resins, cation exchange resins), toxicological profile, tissue penetration, pharmacokinetics and pharmacodynamics.

In some embodiments, the DNase variants are evaluated using an in vitro nucleic acid degradation assay, which can employ single or double-stranded DNA, plasmid DNA, mitochondrial DNA, NETs, or may employ chromatin. In some embodiments, the assay is a NET-degrading assay. The in vitro assay can be performed under different conditions including varying pH, temperature, divalent cations, and/or salt, to evaluate the enzyme characteristics for clinical applications. In some embodiments, enzyme activity is evaluated with fusion to carrier proteins such as albumin or Fc, or with PEGylation.

In some embodiments, the DNase variants are evaluated for their expression potential in prokaryotic and/or eukaryotic (including mammalian and non-mammalian) expression systems, including their ease of expression, yield of recombinant enzyme, ability to be secreted as active protein, the lack of inclusion bodies, the presence of and identification of sites of glycosylation, and ease of purification with or without purification tags. In some embodiments, enzyme expression is evaluated with fusion to carrier proteins such as albumin or Fc. In some embodiments, DNase variants are evaluated with substitution of any unpaired Cysteines.

In some embodiments, the DNase variants are evaluated for short term and/or long term stability (e.g., upon storage for several months at 4° C. and/or room temperature). Stability can be evaluated by formation of aggregates, change of composition color, and/or enzyme activity.

In some embodiments, the DNase variants are evaluated in animal models, including for immunogenic potential (e.g., presence of anti-DNase variant antibodies), half-life in circulation, protease resistance, bioavailability, and/or NET-degrading activity. In some embodiments, activity is evaluated in disease models. Exemplary animal models may include rodent models (mouse, rat, rabbit) or primate models (e.g., chimpanzee).

In some embodiments, at least one DNase variant is evaluated in a genetically modified mouse deficient in D1 and D1L3 activity, the mouse further having a heterologous expression of a G-CSF polynucleotide (e.g., in hepatocyte cells) or induction of a sustained endogenous G-CSF expression (e.g., via repetitive administration of microbial compounds). This mouse model accumulates NETs and rapidly develops NET-related vascular occlusions. In these embodiments, the invention comprises selecting DNase enzyme that reduces the accumulation of NETs. The selected enzyme is formulated (as described) for administration to a human patient. One skilled in the art recognizes standard methods for generating double knockout Dnase1$^{-/-}$, Dnase1l3$^{-/-}$ mice. Detailed descriptions can be found in, for example, U.S. Application Publication No. US 2019/0350178 and PCT International Patent Publication No. WO 2019/036719, the disclosure of which is incorporated herein by reference the in its entirety.

The invention further provides pharmaceutical compositions comprising extracellular DNase variant as described herein, or optionally the polynucleotide or the vector as described, and a pharmaceutically acceptable carrier. The pharmaceutical composition may be formulated for any administration route, including topical, parenteral, or pulmonary administration. In various embodiments, the composition is formulated for intradermal, intramuscular, intraperitoneal, intraarticular, intravenous, subcutaneous, intraarterial, oral, sublingual, pulmonary, or transdermal administration.

In various embodiments, a selected DNase variant is formulated with a "pharmaceutically acceptable carrier", which includes any carrier that does not interfere with the effectiveness of the biological activity and is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

In other aspects, the invention provides a method for treating a subject in need of extracellular DNA degradation, extracellular chromatin degradation, extracellular trap (ET) degradation and/or neutrophil extracellular trap (NET) degradation. The method comprises administering a therapeutically effective amount of the extracellular DNase variant or composition described herein. Exemplary indications where a subject is in need of extracellular DNA or chromatin degradation (including ET or NET degradation) are disclosed in PCT/US18/47084 (corresponding to WO 2019/036719 and U.S. Pat. No. 10,696,956).

In some embodiments, the subject exhibits impaired NET degradation and/or exhibits pathological NET accumulation. In some embodiments, the subject has a chronic or acute inflammatory disorder. In some embodiments, the subject has an acute or chronic infection.

In various embodiments, the present invention pertains to the treatment of diseases or conditions characterized by the presence or accumulation of NETs. Such diseases or conditions include, but are not limited to, diseases associated with chronic neutrophilia (e.g., an increase in the number of neutrophils), neutrophil aggregation and leukostasis, thrombosis and vascular occlusion (e.g. sickle cell disease), ischemia-reperfusion injury (e.g. midgut volvulus, testicular torsion, limb ischemia reperfusion, vital organ ischemia-reperfusion, organ transplantation), surgical and traumatic tissue injury, an acute or chronic inflammatory reaction or disease, an autoimmune disease (e.g. systemic lupus erythematosus (SLE), lupus nephritis, rheumatoid arthritis, vasculitis, systemic sclerosis), cardiovascular disease (e.g., myocardial infarction, stroke, atherosclerosis, venous thromboembolism, including thrombolytic therapy), metabolic disease (e.g., diabetes), systemic inflammation (e.g., systemic inflammatory response syndrome (SIRS), sepsis, septic shock, disseminated intravascular coagulation (DIC), and thrombotic microangiopathy (TMA)), inflammatory diseases of the respiratory tract (e.g. cystic fibrosis, chronic obstructive pulmonary disease (COPD), acute lung injury (ALI), smoke induced lung injury, transfusion induced lung injury (TRALI), acute respiratory distress syndrome (ARDS), and asthma, atelectasis, bronchitis, empyema), renal inflammatory diseases (acute and chronic kidney diseases, including acute kidney injury (AKI) and chronic kidney disease (CKD), inflammatory diseases related to transplated tissue (e.g. graft-versus-host disease) and cancer (e.g. leukemia, tumor metastasis, and solid tumors).

In some embodiments, the subject has or is at risk of NETs occluding ductural systems. The present invention can be administered to a subject to treat pancreatitis, cholangitis, conjunctivitis, mastitis, dry eye disease, obstructions of vas deferens, or renal diseases. In some embodiments, the ductal system is bile duct, tear duct, lactiferous duct, cystic duct, hepatic duct, ejaculatory duct, parotid duct, submandibular duct, major sublingual duct, bartholin's duct, cerebral aqueduct, pancreas, mammary gland, vas deferens, ureter, urinary bladder, gallbladder, and liver. For example, the subject may have pancreatitis, cholangitis (e.g., primary sclerosing cholangitis), conjunctivitis, mastitis, dry eye disease, an obstruction of the vas deferens, or renal disease. In some embodiments, the DNase enzyme is administered by intravenous, intraarterial, or intraperitoneal administration. In various embodiments, the DNase when applied, for example, intravenously, will be present in enzymatically active form in various ductal systems, such as in bile fluid.

In some embodiments, the subject has or is at risk of NETs accumulating on endothelial surfaces (e.g., surgical adhesions), the skin (e.g. wounds/scarring), or in synovial joints (e.g. gout and arthritis). The present invention can be administered to a subject to treat a condition characterized by an accumulation of NETs on an endothelial surface such as, but not limited to, a surgical adhesion. In various embodiments, the present invention can be administered to a subject to treat a condition characterized by an accumulation of NETs on skin such as, but not limited to, wounds and scars. In certain embodiments, the present invention can be administered to a subject to treat a condition characterized by an accumulation of NETs in a synovial joint such as, but not limited to, gout and arthritis.

In various embodiments, the subject has a disease that is or has been treated with wild-type DNases, including D1 and streptodornase. Such diseases or conditions include thrombosis, stroke, sepsis, lung injury, atherosclerosis, viral infection, sickle cell disease, myocardial infarction, ear infection, wound healing, liver injury, endocarditis, liver infection, pancreatitis, primary graft dysfunction, limb ischemia reperfusion, kidney injury, blood clotting, alum-induced inflammation, hepatorenal injury, pleural exudations, hemotorax, intrabiliary blood clots, post pneumatic anemia, ulcers, otolaryngological conditions, oral infections, minor injuries, sinusitis, post-operative rhinoplasties, infertility, bladder catheter, wound cleaning, skin reaction test, pneumococcal meningitis, gout, leg ulcers, cystic fibrosis, Kartegener's syndrome, asthma, lobar atelectasis, chronic bronchitis, bronchiectasis, lupus, primary cilliary dyskinesia, bronchiolitis, empyema, pleural infections, cancer, dry eyes disease, lower respiratory tract infections, chronic hematomas, Alzheimer's disease, and obstructive pulmonary disease.

In certain embodiments, the present invention pertains to the treatment of diseases or conditions characterized by deficiency of D1, deficiency of D1L3, and deficiency of D1 and D1L3. In some cases, the subject has a mutation in the Dnase1 and/or the Dnasell3 gene. Such subjects can also have an autoimmune disease (e.g., SLE, systemic sclerosis) or an inflammatory disease. In some cases, the subject has an acquired inhibitor of Dl (e.g., anti-DNase1 -antibody and actin) and/or the D1L3 (e.g., anti-DNasell3-antibody). Such subjects can also have an autoimmune disease (e.g., SLE, systemic sclerosis) or an inflammatory disease (e.g., sepsis and ischemia-reperfusion injury).

The invention is further described with reference to the following non-limiting examples.

EXAMPLES

Example 1

The Approach Used for Engineering DNase Variants for Therapeutic Applications

DNASE1 (D1) forms along with DNASE1-LIKE 1 (D1L1), DNASE1-LIKE 2 (D1L2) and DNASE1-LIKE 3 (D1L3), the DNASE1-protein family, a group of homologous secreted DNase enzymes. DNASE2A and DNASE2B form an additional group of homologous DNase enzymes. DNASE1- and DNASE2-protein family members are evolutionary conserved and expressed in various species, including humans. In general, all extracellular DNase enzymes provide drug candidates for therapies of diseases that are associated NETs. However, the physical, enzymatic, toxicological, and pharmacokinetic properties of these enzymes are not ideal for clinical applications.

An engineered D1 variant that is resistant to actin has been generated. Actin is an inhibitor of wild type D1. In brief, the 3D structure of the actin-DNASE1 complex was generated and actin binding sites in D1 were identified. Next, recombinant D1 variants with amino acids substitutions in the actin binding sites were expressed and tested for their sensitivity towards actin inhibition. The mutation A136F in SEQ ID NO: 1 was identified to generate the best actin-resistant D1 variants. See Ulmer et al., *PNAS USA* Vol. 93, pp 8225-8229 (1996).

Rats express a D1 variant that is naturally resistant to actin inhibition due to mutations in actin binding sites. Furthermore, the enzymatic activity of human D1L2 and D1L3 is not inhibited by actin. Indeed, human D1L3 features an F139, which corresponds to A136 in human D1 and likely causes the actin-resistance of D1L3.

Without being bound by theory, it was proposed that enzymatic properties that are favorable for development of therapy with extracellular DNase enzymes can be transferred to human extracellular DNase enzymes from extracellular DNase enzymes expressed in other species (e.g. rat) or from other members of the same extracellular DNase protein family (e.g. DNASE1-protein family comprised of DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), and DNASE1-protein family comprised of DNASE2A (D2A), and DNASE2B (D2B)).

A protein engineering technology, termed Building Block Protein Engineering, can be applied to members of the DNASE1 and DNASE2 protein family and an extracellular DNase (e.g. D1, D1L1, D1L2, D1L3, D1L3-2, D2A, D2B). Building Block Protein Engineering is based on the following steps: providing a protein-protein alignment of donor and recipient DNase enzymes; identifying variable amino acid(s) for transfer, the variable amino acid(s) being flanked by one or more conserved amino acids in the donor and recipient DNase enzymes; substituting the variable amino acid(s) of the recipient DNase with the variable amino acid(s) of the donor DNase to create a chimeric DNase; and recombinantly producing the chimeric DNase.

Figure 1:
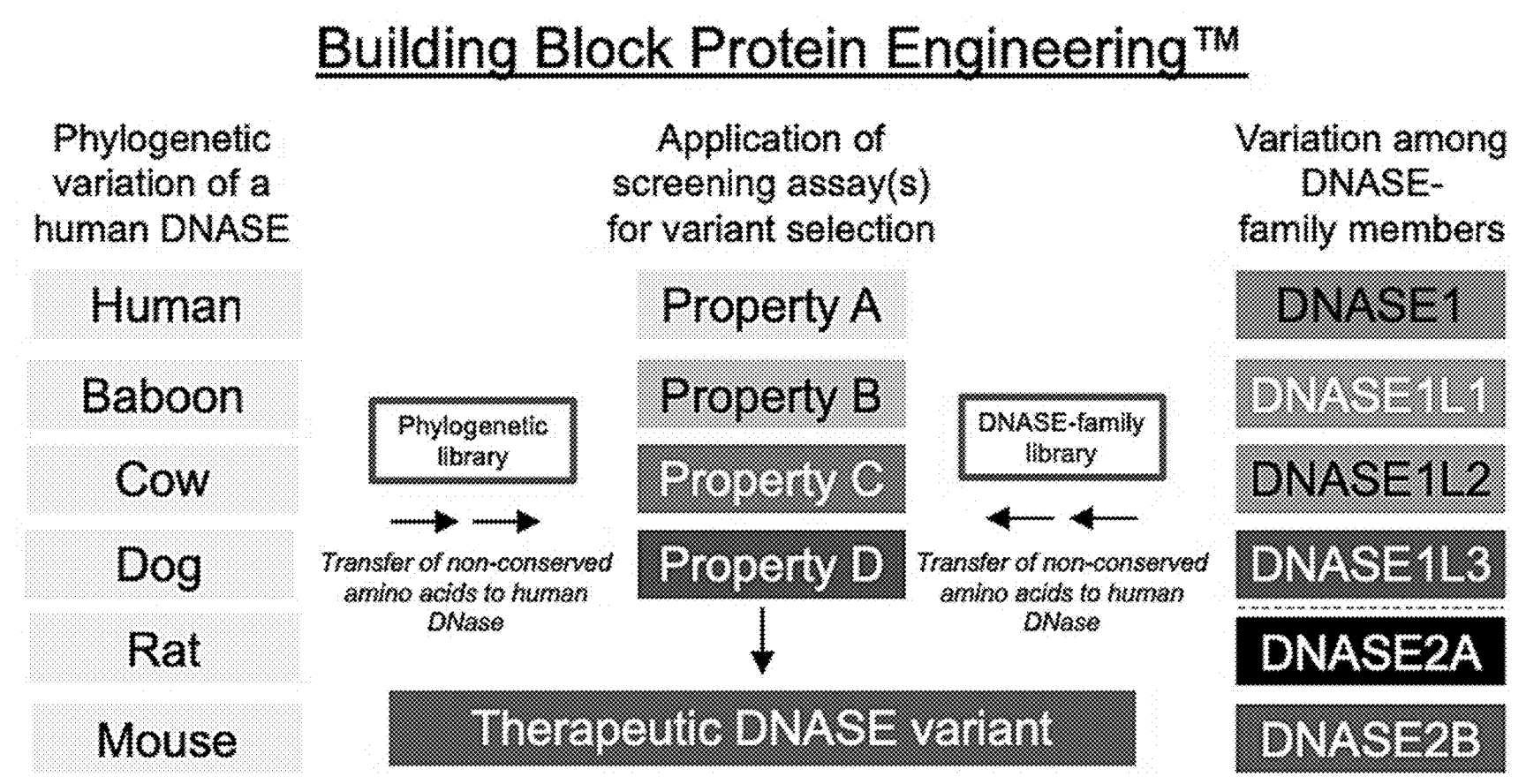

This approach can generate two distinct types of libraries with variants of extracellular DNase enzymes: a library based on phylogenetic variation of a human extracellular DNase, and a library that is based on variation among DNase-family members (FIG. 1).

For example, FIG. 2 shows the alignment of human D1L3, with D1L3 from other species, including chimpanzee, baboon, mouse, rat, rabbit, dog, pig, guinea pig, cow, and elephant, and which identifies non-conserved amino acids (Building Blocks) that when transferred to human D1L3 result in phylogenetic variants of human D1L3. These feature the following mutations: M21L, K22R, I22L, I22V, E33A, E33Y, E33G, S34A, S34T, Q36K, Q36R, E37A, E37Q, D48N, K39Q, K39H, K39R, K39C, N40E, N40Q, N40K, A41V, V44I, V53I, I53L, I54M, V57L, I60V, N64S, H64S, R66N, R66M, I70V, I70M, I70T, M72L, E73K, K74R, R77G, R81K, G82S, I83V, I83T, T84M, T84K, S91P, T91V, T91A, L105V, K107M, V111L, S112T, R115T, R115A, R115K, R115D, R115Q, S116K, S116N, S116Y, H118L, H118V, Y119F, H120G, Y122N, Q123E, D124A, D124S, D124N, G125E, A127V, A127T, V129A, F135Y, V137T, Q140H, S141A, H143F, H143Y, V146A, I152V, T157S, T160A, V162I, K163R, V169A, E170D, T173M, T173L, V175M, K176R, K176Q, H177S, H177R, R178Q, K180E, K180N, K181T, K181V, E183A, E183Q, A201S, K203Q, K203R, R212K, R212N, R212G, R212M, V214I, G218K, G218A, Q220E, Q220D, K227R, K227S, K227E, N239K, N239S, N239H, R239C, Q241P, E242D, E242N, V244I, S245N, S245R, K250R, K250D, K250R, K250G, K250N, K250Q, N252S, S253G, S253L, V254T, V254I, D256N, Q258R, Y261F, K262D, K262E, K262L, K262R, K262Q, T264S, E266S, E267K, E267Q, E267K, D270N, D270E, V271I, S282E, R285T, F287I, S290N, K291R, V294I, T295S, T295Q, L296V, L296P, L296S, R297K, K299R, T300K, T300A, S302G, S302A, S302V, S302T, K303N, K303S, K303R, R304H, R304S, S305P, S305T, and S305A.

FIG. 3 shows the alignment of human D1L3 with human D1L1, and identifies non-conserved amino acids (Building Blocks) that when transferred to human D1L3 result in variants of human D1L3. These feature the following mutations: S2_L5delinsHYPT, P7_L9delinsL, L11F, L13 S17delinsILANG, L19delinsQ, M21F, S25A, V28_S34delinsAQRLTLA, Q36_A41delinsVAREQV, V44_I45delinsTL, K47_K50delinsRILA, 155_M58delinsMVLQ, I60_K61delinsVV, N6_C68delinsSGSAI, 170L, M72_L74delinsLRE, N78_R81delinsFDGS, 183_T84delinsP, N86_I89delinsSTLS, S91_R92delinsPQ, N96S, K99M, Q101T, A103_L105delinsVYF, K107_S112delinsRSHKTQ, K114_R115delinsLS, H118V, H120N, Y122_A127delinsED, S131A, V137_W138delinsAQ, Q140_S141delinsSL, H143_F149delinsSNVLPSL, I151_I152delinsLV, E159_V162delinsKAVE, I165_A167delinsLNA, V169_E170delinsYD, Y172_D174delinsFLE, K176_R178delinsSQH, K180_F184delinsQSKDV, G193D, S195_P198delinsASLT, A201_R206delinsRLDKLE, D210E, R212G, V214H, L216V, G218A, Q220G, K226_K227delinsRA, N230H, A232T, I236V, R239H, Q246_V249delinsERCR, S246_V254delinsLLHTAAA, Q258_K262delinsPTSFQ, D270_V271delinsNI, F275Y, F279_K280delinsVE, Q282_S283delinsKL, R285Q, F287_K292delinsHSVQPL, V294L, L296_S205delinsVLLLLSLLSPQLCPAA.

Such extracellular DNase variants can be screened in assays for altered properties, including altered pH and temperature optimum, requirement for divalent cations for enzymatic activity, mechanisms of enzymatic inhibition (e.g. salt, divalent cations, actin, heparin, proteases), substrate affinity and specificity (e.g. single-stranded DNA, double-stranded DNA, chromatin, NETs, plasmid DNA, mitochondrial DNA), localization upon secretion (e.g. membrane-bound, extracellular matrix), localization signals (e.g. nuclear localization signal, membrane anchor), glycosylation sites, disulfide-bonds and unpaired cysteines, compatibility with GMP-compliant in vitro expression systems (e.g. bacteria. yeast, mammalian cells), compatibility with carriers (e.g. PEGylation, Fc fragment, albumin), compatibility with GMP-compliant purification methods (e.g. anion exchange resins, cation exchange resins), toxicological profile, tissue penetration, pharmacokinetics and pharmacodynamics.

An extracellular DNase with altered profile can provide a drug candidate for diseases that are associated with NETs.

Example 2

Development of Building Block Engineering of DNaseI-Protein Family Members

D1L3 features three sites that contain additional amino acids: the C-terminal tail starting after Q282 (NH2-SSRAFTBSKKSVTLRKKTKSKRS-COOH) (SEQ ID NO: 21), and at two sites within the enzyme at S79/R80 and at K226. The 23 amino acids of the C-terminal tail of D1L3 have been attached to the C-terminus of D1. It was observed that the insertion of an arginine-residue at position 226 of DNase1 (A226_T227insK) generated a D1-variant with reduced enzymatic activity to degrade dsDNA, while no such effect was observed with the substitution T227K. Thus, an insertion of a K/R-residue goes along with a risk of reducing D1 function. The insertion of a charged amino acid may influence the local protein structure. Given that D1 is a globular enzyme that comprises one amino acid chain, it is conceivable that such local alteration may render the whole enzyme inactive. Indeed, numerous non-conservative mutations throughout the D1 amino acid sequence inactivate the enzyme. Without being bound by theory, it was hypothesized that the transfer of local protein structures by implanting not only single arginine and lysine residues but also the neighboring amino acids sequences reduces the risk of inactivation. Conserved amino acids were searched within D1 and D1L3 for in the vicinity of A226 T227insK that can be used as anchors for the insertion. A D223/T224/T225 motif and a conserved T229 in D1 as N-terminal and C-terminal anchors, respectively were identified. 3 amino acids within D1 (ATP) were replaced with 4 amino acids, including K226, from D1L3 (VKKS) in silico. Expression of the cDNA of the new D1-variant (A226_P228delinsVKKS) in HEK239 cells revealed a functionally active enzyme with a similar dsDNA-degrading activity, when compared to wild-type D1. The data suggest that the variable amino acids between conserved amino acids are interchangeable between D1 and D1L3.

We conceptualized a building block-technology to transfer enzymatic properties from one member of the Dl-protein family to another. The following cardinal steps characterize the technology (FIG. 4):

(1) Provide protein-protein alignment of donor and recipient DNase (2) Identify variable amino acid or amino acid sequence for transfer (building block)

(3) Identify conserved amino acids in donor and recipient DNase that are located up and downstream of building block (anchors), respectively.

(4) Replace cDNA encoding for building block between C- and N-anchors in recipient DNase, with cDNA between the anchors in donor DNase.
(5) Synthesize cDNA of chimeric DNase, followed by in vitro/in vivo expression into a recipient organism that is preferably deficient in both donor and recipient DNase (e.g. CHO cells or Dnase1$^{-/-}$Dnase1$^{-/-}$mice).

Example 3

Engineering DNase1 Variants Through Building Block Technology

Figure 5:
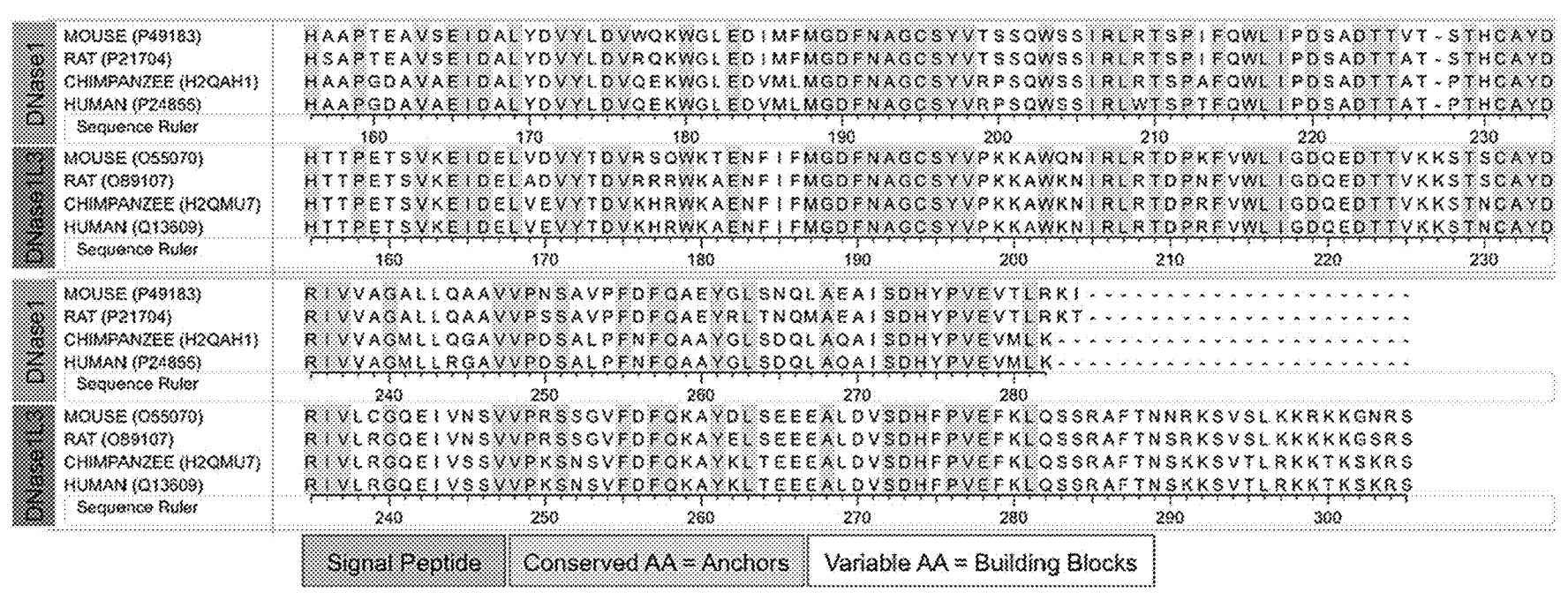
Figure 6A:
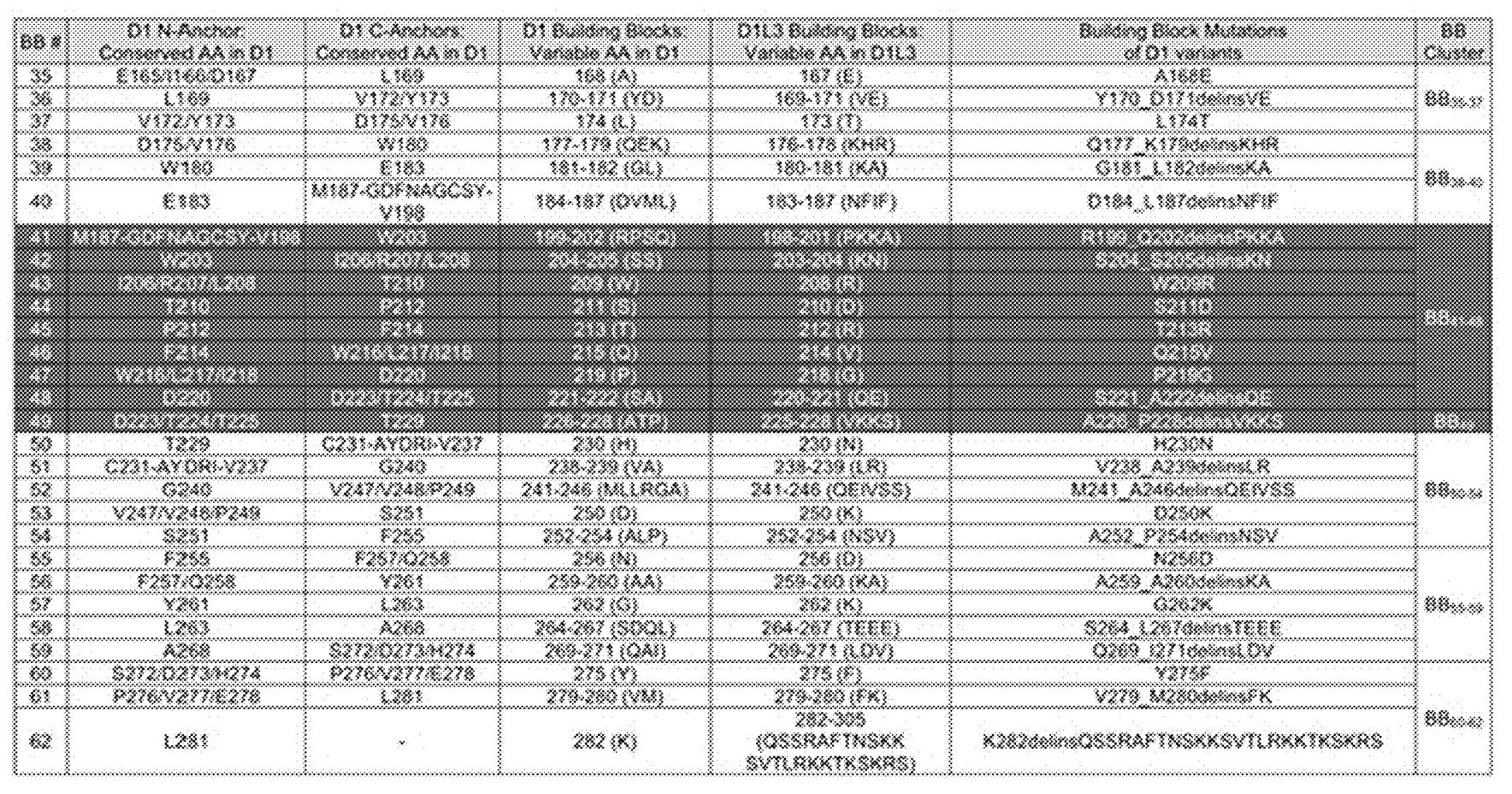
Figure 6B:
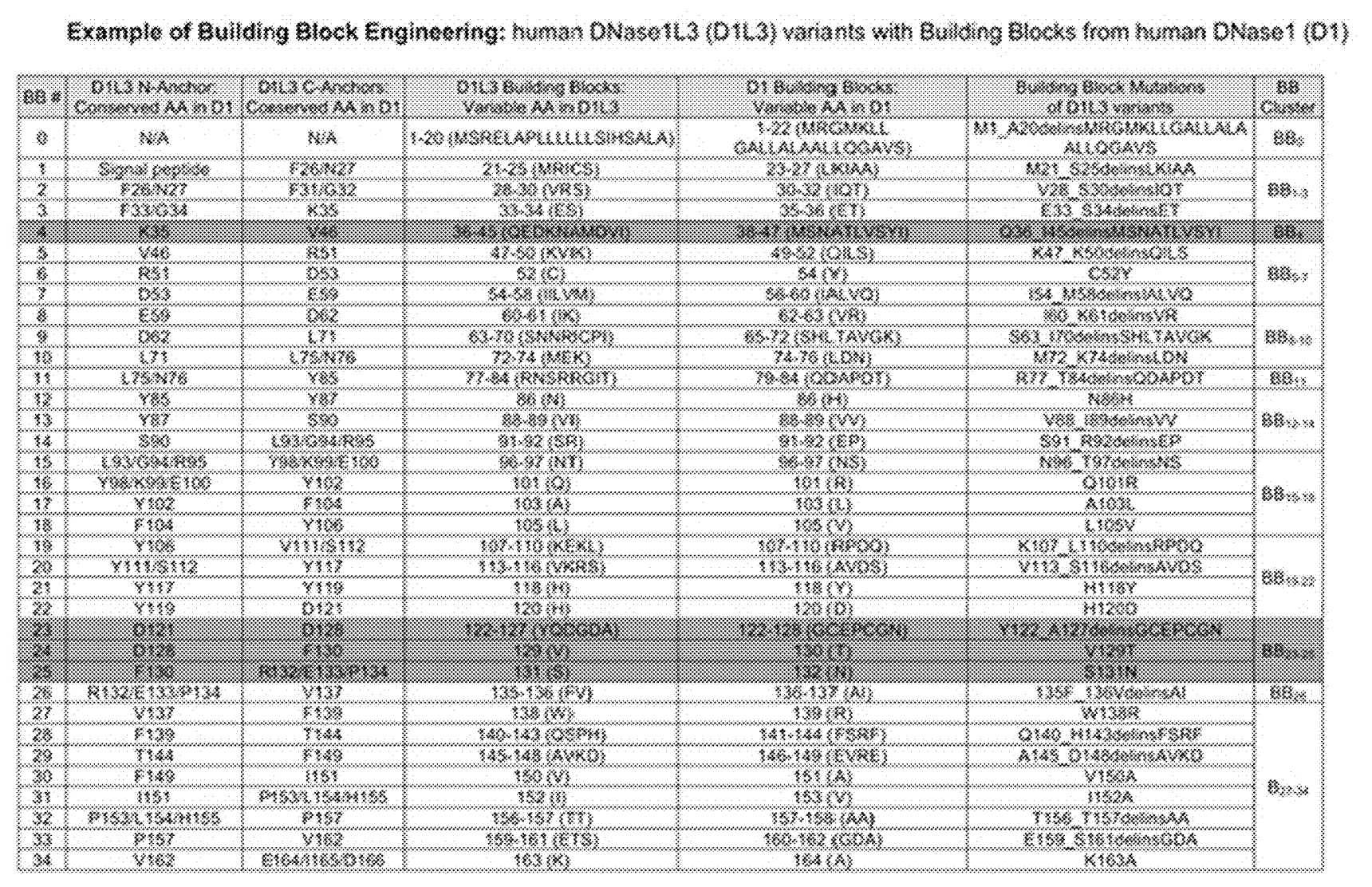

A multiple-species alignment of D1 and D1L3 from human, mouse, rat, and chimpanzee (FIG. 5), showed that N- and C-terminal anchors are conserved among these species. These anchor amino acids or amino acid sequences flank 62 building blocks of variable amino acids and amino acid sequences, which include the amino acid sequence in D1 (ATP) and D1L3 (VKKS) from building blocks #49 (FIGS. 6A-6B).

The transfer of these building blocks from D1L3 into D1 generates D1-variants with the following mutations (FIGS. 6A-6B):
1M_S22delinsMSRELAPLLLLLLSIHSALA,
L23_A27delinsMRICS,
I30_T32delinsVRS, E35_T36delinsES, M38_I47delinsQEDKNAMDVI,
Q49_S52delinsKVIK, Y54C, I56_Q60delinsIILVM, V62_R63delinsIK,
S65_K72delinsSNNRICPI, L74_N76delinsMEK, Q79_T84delinsRNSRRGIT, H86N,
V88_V89delinsVI, E91_P92delinsSR, N96_S97delinsNT, R101Q, L103A, V105L,
R107_Q110delinsKEKL, A113_S116delinsVKRS, Y118H, D120H,
G122_N128delinsYQDGDA, T130S, N132S, A136_I137delinsFV, R139W,
F141_F144delinsQSPH, E146_E149delinsAVKD, A151V, V153I,
A157_A158delinsTT, G160_A162delinsETS, A164K, A168E, Y170 D171delinsVE,
L174T, Q177_K179delinsKHR, G181L182delinsKA, D184_L187delinsNFIF,
R199_Q202delinsPKKA, S204_S205delinsKN, W209R, S211D, T213R, Q215V,
P219G, S221_A222delinsQE, A226_P228delinsVKKS, H230N, V238_A239delinsLR,
M241_A246delinsQEIVSS, D250K, A252_P254delinsNSV, N256D,
A259_A260delinsKA, G262K, S264_L267delinsTEEE, Q269_I271delinsLDV,
Y275F, V279_M280delinsFK, and K282delinsQSSRAFTNSKKSVTLRKKTKSKRS.

The following D1L3-variants are generated if the building blocks are transferred from D1 to D1L3 (FIGS. 6A-6B):
M1_A20delinsMRGMKLLGALLALAALLQGAVS,
M21_S25delinsLKIAA,
V28_S30delinsIQT, E33_S34delinsET, Q36_I45delinsMSNATLVSYI,
K47_K50delinsQILS, C52Y, I54_M58delinsIALVQ, I60_K61delinsVR,
S63_I70delinsSHLTAVGK, M72_K74delinsLDN, R77_T84delinsQDAPDT, N86H,
V88_I89delinsVV, S91_R92delinsEP, N96_T97delinsNS, Q101R, A103L, L105V,
K107_L110delinsRPDQ, V113_S116delinsAVDS, H118Y, H120D,
Y122_A127delinsGCEPCGN, V129T, S131N, 135F_136VdelinsAI, W138R,
Q140_H143delinsFSRF, A145_D148delinsAVKD, V150A, I152A,
T156_T157delinsAA, E159_S161delinsGDA, K163A, E167A, V169_E170delinsYD,
T173L, K176_R178delinsQEK, K180_A181delinsGL, N183_F186delinsDVML,
P198_A20delinsRPSQ, K203_N204delinsSS, R208W, D210S, R212T, V214Q,
G218P, Q220_E221delinsSA, V225_S228delinsATP, N230H, L238_R239delinsVA,
Q241_S246delinsMLLRGA, K250D, N252_V254delinsALP, D256N,
K259_A260delinsAA, K262G, T264_E267delinsSDQL, L269_V271delinsVA,
F275Y, F279_K280delinsVM, and Q282_S305delinsK.

Next, we conceptualized a sequential approach to engineer D1-variants with D1L3 activity that starts with the transfer of multiple adjacent building blocks (clusters), continues with the transfer of individual building blocks, and ends with a transfer of individual amino acids or the combination of multiple building blocks into new chimeric enzymes (FIG. 7). This approach reduces the number of D1-D1L3-chimera in the initial screening.

To test our method, we designed a total of 19 D1-variants comprising either individual building blocks or clusters of building block cluster from D1L3 (FIG. 6). These D1-variants feature the following amino acid mutations:
1M_S22delinsMSRELAPLLLLLLSIHSALA,
L23_A27delinsMRICS/I30_T32delinsVRS/ E35_T36delinsES,
M38_I47delinsQEDKNAMDVI, Q49_S52delinsKVIK/ Y54C/I56_Q60delinsIILVM,
V62_R63delinsIK/S65_K72delinsSNNRICPI/ L74_N76delinsMEK,
Q79_T84delinsRNSRRGIT, H86N/V88_V89delinsVI/ E91_P92delinsSR,
N96_S97delinsNT/R101Q/L103A/V105L,
R107_Q110delinsKEKL/A113_S116delinsVKRS/Y118H/ D120H,
G122_N128delinsYQDGDA/T130S/N132S, A136_I137delinsFV,
R139W/F141_F144delinsQSPH/E146_E149delinsAVKD/ A151VN153I/A157_A158d
elinsTT/G160_A162delinsETS/A164K, A168E/ Y170_D171 delinsVE/L174T,
Q177_K179delinsKHR/G181_L182delinsKA/ D184_L187delinsNFIF,
R199_Q202delinsPKKA/S204_S205delinsKN/W209R/ S211D/T213R/Q215V/P219G/
S221_A222delinsQE, A226_P228delinsVKKS,
H230N/V238_A239delinsLR/M241_A246delinsQEIVSS/ D250K/A252_P254delinsNS
N256D/A259_A260delinsKA/G262K/ S264_L267delinsTEEE/Q269_I271delinsLDV,
and Y275F/V279_M280delinsFK/ K282delinsQSSRAFTNSKKSVTLRKKTKSKRS.

Next, we cloned the cDNA into an expression vector, which was transfected into HEK293 cells. Analysis of the cell supernatants showed dsDNA degradation by all samples (FIG. 8). Furthermore, we observed that the transfer of building blocks (BB) 11, BB 12-14, BB 26, BB 41-48, and BB 49 from D1L3 to D1 resulted in enzymes with increased chromatin degrading activity. All of these chimeric enzymes exhibited the same or more activity to degrade dsDNA substrates than wild-type D1. The building blocks 11 and 49 from D1L3 contain R80/R81 and K227, respectively, which are not present in D1. The D1L3-BB cluster 41-48 features 5 additional arginine and lysine residues than its counterpart in D1. These additional cationic amino acids may be responsible for the hyperactivity. The D1-building blocks 12-14 and 26 contain the amino acid sequences H86 to R95 and A136 to V138 in SEQ ID NO: 1, which includes amino acid residues that are required for binding of the D1-inhibitor actin. Thus, replacement of these amino acid sequences with the respective building blocks from D1L3, which do not interact with actin, likely generates actin-resistant variants of D1. We now combined BB 11, 14, 26, 41-19 in one novel D1-variant. We observed that the combination of these gain-of-function BBs increased the chromatin degrading of the D1 variant to levels of wild-type D1L3 (FIG. 8). Thus, the BB technology provides a robust method to generate hyperactive D1 variants.

Example 4

Expression and Characterization of D1L3 with Basic Domain Deletion (BDD) in Chinese Hamster Ovarian (CHO) Cells and in *Pichia pastoris*

DNASE1 and DNASE1L3 preferentially cleave protein-free DNA and DNA-histone-complexes (i.e. chromatin), respectively. Previous studies suggest that a basic domain (BD) at the C-terminus of DNASE1L3, which is absent in DNASE1, is responsible for the distinct substrate specificities of both enzymes (Sisirak et al., Cell, 2016; Keyel, Developmental Biology, 2017).

To characterize the amino acids that are responsible for chromatin-degrading activity ("chromatinase" activity), wild-type D1L3 was substituted with building block substitutions from D1, as disclosed in PCT/US2018/047084. The building block substitutions to D1L3 are selected from human D1 and result in variants of human D1L3, which feature the following mutations: M21_R22delinsLK, C24_S25delinsAA, V28_S30delinsIQT, S34T, Q36_V44delinsMSNATLVSY, K47_K50delinsQILS, C52Y, I55_M58delinsIALVQE, I60K61delinsVR, N64I70delinsHLTAVGK, M72K74delinsLDN, R77_I83delinsQDAPD, N86H, I89V, S91_R92delinsEP, T97S, Q101R, A103L, L105V, K107_L110delinsRPDQ, V113_R115delinsAVD, H118Y, H120D, Y122_A127delinsGCEPCGN, V129T, S131N, F135_V136delinsAI, W138R, Q140_H143delinFSRF, A145_D148delinsEVRE, V150A, I152V, T156_T157delinsAA, E159_S161delinsGDA, K163A, E167A, V169_E170delinsYD, T173L, K176_R178delinsQEK, K180_A181delinsGL, N183_F186delinsDVML, P198A201delinsRPSQ, K203_N204delinsSS, R208W, D210S, R212T, V214Q, G218P, Q220_E221delinsSA, V225_S228delinsATP, N230H, L238_R239delinsVA, Q241_S246delinsMLLRGA, K250D, N252_V254delinsALP, D256N, K259A, K262G, T264E267delinsSDQL, L269_V271delinsQA, F275Y, F279_K280delinsVM, Q282_S205delinsK with respect to human D1L3, Isoform 1.

These 63 D1L3variants were screened for loss or gain of chromatin-degrading activity. In brief, D1L3 variants were transiently expressed in CHO cells using an in vitro expression vector. Culture supernatants were collected and tested for chromatin-degrading activity using purified nuclei as a source of chromatin. As shown in FIG. 9, the building block substitution #63 from D1 significantly improved the degradation of high-molecular weight (HMW) chromatin to small fragments, when compared to wild-type D1L3. Building block substitution #63 causes the mutation Q282_S305delinsK, which deletes the full C-terminal BD of D1L3 from amino acid position 283 to 305 and replaces glutamine (Q) at position 282 with lysine.

Example 5

The Paired Basic Amino Acid Cleaving Enzyme Furin Regulates D1L3

The BD domain of D1L3 contains an NLS and three paired basic amino acids that are potentially responsible for the inhibitory effects on enzymatic activity (FIG. 10). The NLS is located between amino acids L286 to S302 [LRKKTKS; Reference: Q13609 (Uniprot)] and therefore absent in all identified hyperactive D1L3 mutants that lack 12 amino acids or more.

Without being bound by theory, it was hypothesized that three sets of paired basic amino acids are K291/1K292, R297/K298/K299, and K303/R304 and may serve as proteolytic cleavage sites of the Paired Basic Amino Acid Cleaving Enzyme (PACE). Furin is a well-characterized PACE, which is involved in the maturation of pro-enzymes. To test the possibility of furin generating active D1L3, and to understand the possible role of furin in activation of chromatinase activity of D1L3, furin-overexpressing CHO cells were transiently transfected with wild-type and BD-deleted D1L3 (S283_S305del mutant). CHO cells without overexpression of furin were included as control. Culture supernatants were collected and tested by western blot using an antibody that targets the N-terminus of D1L3. As shown in FIG. 11, two bands of D1L3 were detected in furin-overexpressing CHO cells. The top band corresponded to D1L3 expressed by CHO cells without overexpression of furin, whereas the lower band corresponded to the BD-deleted D1L3 (FIG. 11). The data suggest that furin and/or other proteases may directly or indirectly delete the BD and thus cause the maturation of D1L3 into its enzymatically active form. This cleavage activity further suggests that C-terminal fusion to carrier proteins will require deletions or amino acid substitutions within the BD to avoid proteolytic cleavage in vivo.

Example 6

Heterologous Expression of Wild-Type D1L3

We analyzed molecular modifications of the C-terminal BD of D1L3 following the heterologous expression of wild-type D1L3.

In the first study, we expressed a wild-type D1L3 that was linked to the Fc fragment via a flexible glycine-serine linker in CHO cells (FIG. 12A). As a control, we used an Fc fusion protein of a Basic Domain Deleted-D1L3. CHO cells were transiently transfected with either DNA construct. We collected supernatants and purified the Fc fusion proteins using protein A. Analysis of purified proteins by SDS-PAGE showed bands of approximately 65-70 kDa, which reflects the molecular weight of the full-length proteins (FIG. 12B). An additional lower molecular weight band (between 29-44 kDa) was observed in proteins purified from CHO cells expressing the WT-DNASE1L3 construct. Using LC-MS and LC/MS/MS, we identified that the N- and C-terminal amino acid sequence of the upper band corresponds to mature DNASE1L3 and Fc fragment, respectively. As seen by others, clipping of the C-terminal lysine residue of the Fc fragment was observed. Surprisingly, analysis of the lower band showed that the N-terminus of the protein contained the serine from the C-terminus of DNASE1L3, i.e. Serine 305 in SEQ ID NO: 4. Collectively these data suggest that the expression of wild-type DNASE1L3 leads to the clipping of the C-terminal serine residue.

In the second study, we expressed a wild-type D1L3 and a D1L3 linked at the N-terminus to albumin via a flexible glycine-serine linker in *Pichia pastoris*. We collected fermentation supernatants and purified the proteins using affinity chromatography. Surprisingly, we observed no full-length D1L3 protein with either expression construct, but various degrees of C-terminal truncations as identified by LC-MS and LC/MS/MS. The expression of wild-type D1L3 produced deletions of 13, 14, and 15 amino acids. Additional proteins with deletions of 8 and 9 amino acids were detected in samples of the wild-type D1L3 albumin fusion protein. In summary, the heterologous expression of wild-type D1L3 leads to the secretion of D1L3 variants with distinct deletions in the C-terminal basic domain. Importantly, the deletions occur after, within, or before the three clusters of basic amino acids (FIG. 13). In further studies, we expressed a wild-type D1L3 linked at the C-terminus to albumin via a flexible glycine-serine linker in *Pichia pastoris* and observed two proteins with a molecular weight similar to D1L3 and albumin, indicating the proteolytic cleavage of the fusion protein in the linker region that contains the BD. Collectively, our data identified the 1(291/1(292, R297/K298/K299, and K303/R304 in SEQ ID NO: 4 as sites for post-translational modifications of wild-type DNASE1L3.

INCORPORATION BY REFERENCE

All patents and publications referenced herein are hereby incorporated by reference in their entireties.

```
Amino Acid Sequences of
Wild-Type Human DNASES
                                       SEQ ID NO: 1
DNASE1 (NP_005212.2):
Signal Peptide, Mature Protein:
MRGMKLLGALLALAALLQGAVSLKIAAFN

IQTFGETKMSNATLVSYIVQILSRYDIAL

VQEVRDSHLTAVGKLLDNLNQDAPDTYHY

VVSEPLGRNSYKERYLFVYRPDQVSAVDS

YYYDDGCEPCGNDTFNREPAIVRFFSRFT

EVREFAIVPLHAAPGDAVAEIDALYDVYL

DVQEKWGLEDVMLMGDFNAGCSYVRPSQW

SSIRLWTSPTFQWLIPDSADTTATPTHCA

YDRIVVAGMLLRGAVVPDSALPFNFQAAY

GLSDQLAQAISDHYPVEVMLK

DNASE1-LIKE 1 (NP_006721.1):
Signal Peptide; Mature Protein:
                                       SEQ ID NO: 2
MHYPTALLFLILANGAQAFRICAFNAQRL

TLAKVAREQVMDTLVRILARCDIMVLQEV

VDSSGSAIPLLLRELNRFDGSGPYSTLSS

PQLGRSTYMETYVYFYRSHKTQVLSSYVY

NDEDDVFAREPFVAQFSLPSNVLPSLVLV

PLHTTPKAVEKELNALYDVFLEVSQHWQS

KDVILLGDFNADCASLTKKRLDKLELRTE

PGFHWVIADGEDTTVRASTHCTYDRVVLH

GERCRSLLHTAAAFDFPTSFQLTEEEALN

ISDHYPVEVELKLSQAHSVQPLSLTVLLL

LSLLSPQLCPAA

DNASE1-LIKE 2 (NP_001365.1):
Signal Peptide, Mature Protein:
                                       SEQ ID NO: 3
MGGPRALLAALWALEAAGTAALRIGAFNI

QSFGDSKVSDPACGSILAKILAGYDLALV

QEVRDPDLSAVSALMEQINSVSEHEYSFV

SSQPLGRDQYKEMYLFVYRKDAVSVVDTY

LYPDPEDVFSREPFVVKFSAPGTGERAPP

LPSRRALTPPPLPAAAQNLVLIPLHAAPH

QAVAEIDALYDVYLDVIDKWGTDDMLFLG

DFNADCSYVRAQDWAAIRLRSSEVFKWLI

PDSADTTVGNSDCAYDRIVACGARLRRSL

KPQSATVHDFQEEFGLDQTQALAISDHFP

VEVTLKFHR

DNASE1-LIKE 3; Isoform 1 (NP_004935.1):
Signal Peptide, Mature Protein:
                                       SEQ ID NO: 4
MSRELAPLLLLLLSIHSALAMRICSFNVR

SFGESKQEDKNAMDVIVKVIKRCDIILVM

EIKDSNNRICPILMEKLNRNSRRGITYNY

VISSRLGRNTYKEQYAFLYKEKLVSVKRS

YHYHDYQDGDADVFSREPFVVWFQSPHTA

VKDFVIIPLHTTPETSVKEIDELVEVYTD

VKHRWKAENFIFMGDFNAGCSYVPKKAWK

NIRLRTDPRFVWLIGDQEDTTVKKSINCA

YDRIVLRGQEIVSSVVPKSNSVFDFQKAY

KLTEEEALDVSDHFPVEFKLQSSRAFTNS

KKSVTLRKKTKSKRS

DNASE1-LIKE 3, Isoform 2 (NP_001243489.1):
Signal Peptide; Mature Protein:
                                       SEQ ID NO: 5
MSRELAPLLLLLLSIHSALAMRICSFNVR

SFGESKQEDKNAMDVIVKVIKRCDIILVM

EIKDSNNRICPILMEKLNREKLVSVKRSY

HYHDYQDGDADVFSREPFVVWFQSPHTAV

KDFVIIPLHTTPETSVKEIDELVEVYTDV

KHRWKAENFIFMGDFNAGCSYVPKKAWKN
```

-continued

IRLRTDPRFVWLIGDQEDTTVKKSTNCAY

DRIVLRGQEIVSSVVPKSNSVFDFQKAYK

LTEEEALDVSDHFPVEFKLQSSRAFTNSK

KSVTLRKKTKSKRS

DNASE2A (O00115):
Signal Peptide; Mature Protein:
SEQ ID NO: 6

MIPLLLAALLCVPAGALTCYGDSGQPVDW

FVVYKLPALRGSEAAQRGLQYKYLDESS

GGWRDGRALINSPEGAVGRSLQPLYRSNT

SQLAFLLYNDQPPQPSKAQDSSMRGHTKG

VLLLDHDGGFWLVHSVPNFPPPASSAAYS

WPHSACTYGQTLLCVSFPFAQFSKMGKQL

TYTYPWVYNYQLEGIFAQEFPDLENVVKG

HHVSQEPWNSSITLTSQAGAVFQSFAKFS

KFGDDLYSGWLAAALGTNLQVQFWHKTVG

ILPSNCSDIWQVLNVNQIAFPGPAGPSFN

STEDHSKWCVSPKGPWICVGDMNRNQGEE

QRGGGILCAQLPALWKAFQPLVKNYQPCN

GMARKPSRAYKI

DNASE2B (Q8WZ79):
Signal Peptide; Mature Protein:
SEQ ID NO: 7

MKQKMMARLLRTSFALLFLGLFGVLGAAT

ISCRNEEGKAVDWFTFYKLPKRQNKESGE

TGLEYLYLDSTTRSWRKSEQLMNDTKSVL

GRTLQQLYEAYASKSNNTAYLIYNDGVPK

PVNYSRKYGHTKGLLLLWNRVQGFWLIHSI

PQFPPIPEEGYDYPPTGRRNGQSGICITF

KYNQYEAIDSQLLVCNPNVYSCSIPATFH

QELIHMPQLCTRASSSEIPGRLLTTLQSA

QGQKFLHFAKSDSFLDDIFAAWMAQRLKT

HLLTETWQRKRQELPSNCSLPYHVYNIKA

IKLSRHSYFSSYQDHAKWCISQKGTKNRW

TCIGDLNRSPHQAFRSGGFICTQNWQIYQ

AFQGLVLYYESCK

Selected Amino Acid Sequences of
Human Wild-Type DNASES
C-terminal tail of human DNASE1-
LIKE 1 (NP_006721.1):
SEQ ID NO: 8

KLSQAHSVQPLSLTVLLLLSLLSPQLCPAA

Proline-rich extension of human
DNASE1-LIKE 2 (NP_001365.1):
SEQ ID NO: 9

SAPGTGERAPPLPSRRALTPPPLPAAAQN

LVLIPL

C-terminal tail of human
DNASE1-LIKE 3; Isoform 1
(NP_004935.1):
SEQ ID NO: 10

SSRAFTNSKKSVTLRKKTKSKRS

Internal sequence of human
DNASE1-LIKE 3; Absent in
Isoform 2 (NP_004935.1):
SEQ ID NO: 11

RNSRRGITYNYVISSRLGRNTYKEQYAFL
YK

Carrier Protein
Human Albumin (P02768):
Signal Peptide + Propeptide;
Mature Protein:
SEQ ID NO: 12

MKWVTFISLLFLFSSAYSRGVFRRDAHKS

EVAHRFKDLGEENFKALVLIAFAQYLQQC

PFEDHVKLVNEVTEFAKTCVADESAENCD

KSLHTLFGDKLCTVATLRETYGEMADCCA

KQEPERNECFLQHKDDNPNLPRLVRPEVD

VMCTAFHDNEETFLKKYLYEIARRHPYFY

APELLFFAKRYKAAFTECCQAADKAACLL

PKLDELRDEGKASSAKQRLKCASLQKFGE

RAFKAWAVARLSQRFPKAEFAEVSKLVTD

LTKVHTECCHGDLLECADDRADLAKYICE

NQDSISSKLKECCEKPLLEKSHCIAEVEN

DEMPADLPSLAADFVESKDVCKNYAEAKD

VFLGMFLYEYARRHPDYSVVLLLRLAKTY

ETTLEKCCAAADPHECYAKVFDEFKPLVE

EPQNLIKQNCELFEQLGEYKFQNALLVRY

TKKVPQVSTPTLVEVSRNLGKVGSKCCKH

PEAKRMPCAEDYLSVVLNQLCVLHEKTPV

SDRVTKCCTESLVNRRPCFSALEVDETYV

PKEFNAETFTFHADICTLSEKERQIKKQT

ALVELVKHKPKATKEQLKAVMDDFAAFVE

KCCKADDKETCFAEEGKKLVAASQAALGL

Amino Acid Sequences of Human
ALBUMIN-DNASE-Fusion proteins
Albumin-Linker-DNASE1;
Signal Peptide + Propeptide,
Albumin, Flexible Linker,
mature DNASE1:
SEQ ID NO: 13

MKWVTFISLLFLFSSAYSRGVFRRDAH

KSEVAHRFKDLGEENFKALVLIAFAQY

LQQCPFEDHVKLVNEVTEFAKTCVADE

SAENCDKSLHTLFGDKLCTVATLRETY

GEMADCCAKQEPERNECFLQHKDDNPN

LPRLVRPEVDVMCTAFHDNEETFLKKY

LYEIARRHPYFYAPELLFFAKRYKAAF

TECCQAADKAACLLPKLDELRDEGKAS
SAKQRLKCASLQKFGERAFKAWAVARL
SQRFPKAEFAEVSKLVTDLTKVHTECC
HGDLLECADDRADLAKYICENQDSISS
KLKECCEKPLLEKSHCIAEVENDEMPA
DLPSLAADFVESKDVCKNYAEAKDVFL
GMFLYEYARRHPDYSVVLLLRLAKTYE
TTLEKCCAAADPHECYAKVFDEFKPLV
EEPQNLIKQNCELFEQLGEYKFQNALL
VRYTKKVPQVSTPTLVEVSRNLGKVGS
KCCKHPEAKRMPCAEDYLSVVLNQLCV
LHEKTPVSDRVTKCCTESLVNRRPCFS
ALEVDETYVPKEFNAETFTFHADICTL
SEKERQIKKQTALVELVKHKPKATKEQ
LKAVMDDFAAFVEKCCKADDKETCFAE
EGKKLVAASQAALGLGGGGSGGGGSGG
GGSLKIAAFNIQTFGETKMSNATLVSY
IVQILSRYDIALVQEVRDSHLTAVGKL
LDNLNQDAPDTYHYVVSEPLGRNSYKE
RYLFVYRPDQVSAVDSYYYDDGCEPCG
NDTFNREPAIVRFFSRFTEVREFAIVP
LHAAPGDAVAEIDALYDVYLDVQEKWG
LEDVMLMGDFNAGCSYVRPSQWSSIRL
WTSPTFQWLIPDSADTTATPTHCAYDR
IVVAGMLLRGAVVPDSALPFNFQAAYG
LSDQLAQATSDHYPVEVMLK

Albumin-Linker-DNASE1-LIKE 1;
Signal Peptide + Propeptide,
Albumin, Flexible Linker,
mature DNASE1-LIKE 1:
SEQ ID NO: 14

<u>MKWVTFISLLFLFSSAYSRGVFRRDAH</u>
KSEVAHRFKDLGEENFKALVLIAFAQY
LQQCPFEDHVKLVNEVTEFAKTCVADE
SAENCDKSLHTLFGDKLCTVATLRETY
GEMADCCAKQEPERNECFLQHKDDNPN
LPRLVRPEVDVMCTAFHDNEETFLKKY
LYEIARRHPYFYAPELLFFAKRYKAAF
TECCQAADKAACLLPKLDELRDEGKAS
SAKQRLKCASLQKFGERAFKAWAVARL
SQRFPKAEFAEVSKLVTDLTKVHTECC
HGDLLECADDRADLAKYICENQDSISS
KLKECCEKPLLEKSHCIAEVENDEMPA
DLPSLAADFVESKDVCKNYAEAKDVFL
GMFLYEYARRHPDYSVVLLLRLAKTYE
TTLEKCCAAADPHECYAKVFDEFKPLV
EEPQNLIKQNCELFEQLGEYKFQNALL
VRYTKKVPQVSTPTLVEVSRNLGKVGS
KCCKHPEAKRMPCAEDYLSVVLNQLCV
LHEKTPVSDRVTKCCTESLVNRRPCFS
ALEVDETYVPKEFNAETFTFHADICTL
SEKERQIKKQTALVELVKHKPKATKEQ
LKAVMDDFAAFVEKCCKADDKETCFAE
EGKKLVAASQAALGLGGGGSGGGGSGG
GGSFRICAFNAQRLTLAKVAREQVMDT
LVRILARCDIMVLQEVVDSSGSAIPLL
LRELNRFDGSGPYSTLSSPQLGRSTYM
ETYVYFYRSHKTQVLSSYVYNDEDDVF
AREPFVAQFSLPSNVLPSLVLVPLHTT
PKAVEKELNALYDVFLEVSQHWQSKDV
ILLGDFNADCASLTKKRLDKLELRTEP
GFHWVIADGEDTTVRASTHCTYDRVVL
HGERCRSLLHTAAAFDFPTSFQLTEEE
ALNISDHYPVEVELKLSQAHSVQPLSL
TVLLLLSLLSPQLCPAA

Albumin-Linker-DNASE1-LIKE 2;
Signal Peptide + Propeptide,
Albumin, Flexible Linker,
mature DNASE1-LIKE 2:
SEQ ID NO: 15

<u>MKWVTFISLLFLFSSAYSRGVFRRDAH</u>
KSEVAHRFKDLGEENFKALVLIAFAQY
LQQCPFEDHVKLVNEVTEFAKTCVADE
SAENCDKSLHTLFGDKLCTVATLRETY
GEMADCCAKQEPERNECFLQHKDDNPN
LPRLVRPEVDVMCTAFHDNEETFLKKY
LYEIARRHPYFYAPELLFFAKRYKAAF
TECCQAADKAACLLPKLDELRDEGKAS
SAKQRLKCASLQKFGERAFKAWAVARL
SQRFPKAEFAEVSKLVTDLTKVHTECC
HGDLLECADDRADLAKYICENQDSISS
KLKECCEKPLLEKSHCIAEVENDEMPA
DLPSLAADFVESKDVCKNYAEAKDVFL
GMFLYEYARRHPDYSVVLLLRLAKTYE
TTLEKCCAAADPHECYAKVFDEFKPLV
EEPQNLIKQNCELFEQLGEYKFQNALL

VRYTKKVPQVSTPTLVEVSRNLGKVGS

KCCKHPEAKRMPCAEDYLSVVLNQLCV

LHEKTPVSDRVTKCCTESLVNRRPCFS

ALEVDETYVPKEFNAETFTFHADICTL

SEKERQIKKQTALVELVKHKPKATKEQ

LKAVMDDFAAFVEKCCKADDKETCFAE

EGKKLVAASQAALGLGGGGSGGGGSGG

GGSLRIGAFNIQSFGDSKVSDPACGSI

IAKILAGYDLALVQEVRDPDLSAVSAL

MEQINSVSEHEYSFVSSQPLGRDQYKE

MYLFVYRKDAVSVVDTYLYPDPEDVFS

REPFVVKFSAPGTGERAPPLPSRRALT

PPPLPAAAQNLVLIPLHAAPHQAVAEI

DALYDVYLDVIDKWGTDDMLFLGDFNA

DCSYVRAQDWAAIRLRSSEVFKWLIPD

SADTTVGNSDCAYDRIVACGARLRRSL

KPQSATVHDFQEEFGLDQTQALAISDH

FPVEVTLKFHR

Albumin-Linker-DNASE1-LIKE 3;
Signal Peptide + Propeptide,
Albumin, Flexible Linker,
mature DNASE1-LIKE 3:

SEQ ID NO: 16

MMKWVTFISLLFLFSSAYSRGVFRRDAH

KSEVAHRFKDLGEENFKALVLIAFAQY

LQQCPFEDHVKLVNEVTEFAKTCVADE

SAENCDKSLHTLFGDKLCTVATLRETY

GEMADCCAKQEPERNECFLQHKDDNPN

LPRLVRPEVDVMCTAFHDNEETFLKKY

LYEIARRHPYFYAPELLFFAKRYKAAF

TECCQAADKAACLLPKLDELRDEGKAS

SAKQRLKCASLQKFGERAFKAWAVARL

SQRFPKAEFAEVSKLVTDLTKVHTECC

HGDLLECADDRADLAKYICENQDSISS

KLKECCEKPLLEKSHCIAEVENDEMPA

DLPSLAADFVESKDVCKNYAEAKDVFL

GMFLYEYARRHPDYSVVLLLRLAKTYE

TTLEKCCAAADPHECYAKVFDEFKPLV

EEPQNLIKQNCELFEQLGEYKFQNALL

VRYTKKVPQVSTPTLVEVSRNLGKVGS

KCCKHPEAKRMPCAEDYLSVVLNQLCV

LHEKTPVSDRVTKCCTESLVNRRPCFS

ALEVDETYVPKEFNAETFTFHADICTL

SEKERQIKKQTALVELVKHKPKATKEQ

LKAVMDDFAAFVEKCCKADDKETCFAE

EGKKLVAASQAALGLGGGGSGGGGSGG

GGSMRICSFNVRSFGESKQEDKNAMDV

IVKVIKRCDIILVMEIKDSNNRICPIL

MEKLNRNSRRGITYNYVISSRLGRNTY

KEQYAFLYKEKLVSVKRSYHYHDYQDG

DADVFSREPFVVWFQSPHTAVKDFVII

PLHTTPETSVKEIDELVEVYTDVKHRW

KAENFIFMGDFNAGCSYVPKKAWKNIR

LRTDPRFVWLIGDQEDTTVKKSTNCAY

DRIVLRGQEIVSSVVPKSNSVFDFQKA

YKLTEEEALDVSDHFPVEFKLQSSRAF

TNSKKSVTLRKKTKSKRS

Albumin-Linker-DNASE1-LIKE 3,
Isoform 2;
Signal Peptide + Propeptide,
Albumin, Flexible Linker,
mature DNASE1-LIKE 3
Isoform 2:

SEQ ID NO: 17

MKWVTFISLLFLFSSAYSRGVFRRDAH

KSEVAHRFKDLGEENFKALVLIAFAQY

LQQCPFEDHVKLVNEVTEFAKTCVADE

SAENCDKSLHTLFGDKLCTVATLRETY

GEMADCCAKQEPERNECFLQHKDDNPN

LPRLVRPEVDVMCTAFHDNEETFLKKY

LYEIARRHPYFYAPELLFFAKRYKAAF

TECCQAADKAACLLPKLDELRDEGKAS

SAKQRLKCASLQKFGERAFKAWAVARL

SQRFPKAEFAEVSKLVTDLTKVHTECC

HGDLLECADDRADLAKYICENQDSISS

KLKECCEKPLLEKSHCIAEVENDEMPA

DLPSLAADFVESKDVCKNYAEAKDVFL

GMFLYEYARRHPDYSVVLLLRLAKTYE

TTLEKCCAAADPHECYAKVFDEFKPLV

EEPQNLIKQNCELFEQLGEYKFQNALL

VRYTKKVPQVSTPTLVEVSRNLGKVGS

KCCKHPEAKRMPCAEDYLSVVLNQLCV

LHEKTPVSDRVTKCCTESLVNRRPCFS

ALEVDETYVPKEFNAETFTFHADICTL

SEKERQIKKQTALVELVKHKPKATKEQ

LKAVMDDFAAFVEKCCKADDKETCFAE

EGKKLVAASQAALGLGGGGSGGGGSGG

```
GGSMRICSFNVRSFGESKQEDKNAMDV
IVKVIKRCDIILVMEIKDSNNRICPIL
MEKLNREKLVSVKRSYHYHDYQDGDAD
VFSREPFVVWFQSPHTAVKDFVIIPLH
TTPETSVKEIDELVEVYTDVKHRWKAE
NFIFMGDFNAGCSYVPKKAWKNIRLRT
DPRFVWLIGDQEDTTVKKSTNCAYDRI
VLRGQEIVSSVVPKSNSVFDFQKAYKL
TEEEALDVSDHFPVEFKLQSSRAFTNS
KKSVTLRKKTKSKRS

Albumin-Linker-DNASE2A;
Signal Peptide + Propeptide,
Albumin, Flexible Linker,
mature DNASE2A:
                                        SEQ ID NO: 18
MKWVTFISLLFLFSSAYSRGVFRRDAH
KSEVAHRFKDLGEENFKALVLIAFAQY
LQQCPFEDHVKLVNEVTEFAKTCVADE
SAENCDKSLHTLFGDKLCTVATLRETY
GEMADCCAKQEPERNECFLQHKDDPN
LPRLVRPEVDVMCTAFHDNEETFLKKY
LYEIARRHPYFYAPELLFFAKRYKAAF
TECCQAADKAACLLPKLDELRDEGKAS
SAKQRLKCASLQKFGERAFKAWAVARL
SQRFPKAEFAEVSKLVTDLTKVHTECC
HGDLLECADDRADLAKYICENQDSISS
KLKECCEKPLLEKSHCIAEVENDEMPA
DLPSLAADFVESKDVCKNYAEAKDVFL
GMFLYEYARRHPDYSVVLLLRLAKTYE
TTLEKCCAAADPHECYAKVFDEFKPLV
EEPQNLIKQNCELFEQLGEYKFQNALL
VRYTKKVPQVSTPTLVEVSRNLGKVGS
KCCKHPEAKRMPCAEDYLSVVLNQLCV
LHEKTPVSDRVTKCCTESLVNRRPCFS
ALEVDETYVPKEFNAETFTFHADICTL
SEKERQIKKQTALVELVKHKPKATKEQ
LKAVMDDFAAFVEKCCKADDKETCFAE
EGKKLVAASQAALGLGGGGSGGGGSGG
GGSCYGDSGQPVDWFVVYKLPALRGSG
EAAQRGLQYKYLDESSGGWRDGRALIN
SPEGAVGRSLQPLYRSNTSQLAFLLYN
DQPPQPSKAQDSSMRGHTKGVLLLDHD
GGFWLVHSVPNFPPPASSAAYSWPHSA CTYGQTLLCVSFPFAQFSKMGKQLTYT
YPWVYNYQLEGIFAQEFPDLENVVKGH
HVSQEPWNSSITLTSQAGAVFQSFAKF
SKFGDDLYSGWLAAALGTNLQVQFWHK
TVGILPSNCSDIWQVLNVNQTAFPGPA
GPSFNSTEDHSKWCVSPKGPWTCVGDM
NRNQGEEQRGGGTLCAQLPALWKAFQP
LVKNYQPCNGMARKPSRAYKI Albumin-Linker-DNASE2B;
Signal Peptide + Propeptide,
Albumin, Flexible Linker,
mature DNASE2B:
                                        SEQ ID NO: 19
MKWVTFISLLFLFSSAYSRGVFRRDAH
KSEVAHRFKDLGEENFKALVLIAFAQY
LQQCPFEDHVKLVNEVTEFAKTCVADE
SAENCDKSLHTLFGDKLCTVATLRETY
GEMADCCAKQEPERNECFLQHKDDPN
LPRLVRPEVDVMCTAFHDNEETFLKKY
LYEIARRHPYFYAPELLFFAKRYKAAF
TECCQAADKAACLLPKLDELRDEGKAS
SAKQRLKCASLQKFGERAFKAWAVARL
SQRFPKAEFAEVSKLVTDLTKVHTECC
HGDLLECADDRADLAKYICENQDSISS
KLKECCEKPLLEKSHCIAEVENDEMPA
DLPSLAADFVESKDVCKNYAEAKDVFL
GMFLYEYARRHPDYSVVLLLRLAKTYE
TTLEKCCAAADPHECYAKVFDEFKPLV
EEPQNLIKQNCELFEQLGEYKFQNALL
VRYTKKVPQVSTPTLVEVSRNLGKVGS
KCCKHPEAKRMPCAEDYLSVVLNQLCV
LHEKTPVSDRVTKCCTESLVNRRPCFS
ALEVDETYVPKEFNAETFTFHADICTL
SEKERQIKKQTALVELVKHKPKATKEQ
LKAVMDDFAAFVEKCCKADDKETCFAE
EGKKLVAASQAALGLGGGGSGGGGSGG
GGSATISCRNEEGKAVDWFTFYKLPKR
QNKESGETGLEYLYLDSTTRSWRKSEQ
LMNDTKSVLGRTLQQLYEAYASKSNNT
AYLIYNDGVPKPVNYSRKYGHTKGLLL
WNRVQGFWLIHSIPQFPPIPEEGYDYP
PTGRRNGQSGICITFKYNQYEAIDSQL
LVCNPNVYSCSIPATFHQELIHMPQLC
```

```
TRASSSEIPGRLLTTLQSAQGQKFLHF

AKSDSFLDDIFAAWMAQRLKTHLLTET

WQRKRQELPSNCSLPYHVYNIKAIKLS

RHSYFSSYQDHAKWCISQKGTKNRWTC

IGDLNRSPHQAFRSGGFICTQNWQIYQ

AFQGLVLYYESCK

SEQ ID NO: 20
(Intentionally left blank)
                                SEQ ID NO: 21
(Intentionally left blank)
                                SEQ ID NO: 23
(Intentionally left blank)
                                SEQ ID NO: 24
(Intentionally left blank)
                                SEQ ID NO: 25
(Intentionally left blank)
                                SEQ ID NO: 26
(Intentionally left blank)
                                SEQ ID NO: 27
(Intentionally left blank)
                                SEQ ID NO: 28
(Intentionally left blank)
Human DNASE1L3 variants
                                SEQ ID NO: 29
(Intentionally left blank)
DNASE1L3, Q282_S305delinksK
(Signal Peptide; Mature Protein):
                                SEQ ID NO: 30
MSRELAPLLLLLLSIHSALAMRICSFN

VRSFGESKQEDKNAMDVIVKVIKRCDI

ILVMEIKDSNNRICPILMEKLNRNSRR

GITYNYVISSRLGRNTYKEQYAFLYKE

KLVSVKRSYHYDYQDGDADVFSREPF

VVWFQSPHTAVKDFVIIPLHTTPETSV

KEIDELVEVYTDVKHRWKAENFIFMGD

FNAGCSYVPKKAWKNIRLRTDPRFVWL

IGDQEDTTVKKSINCAYDRIVLRGQEI

VSSVVPKSNSVFDFQKAYKLTEEEALD

VSDHFPVEFKLK

Murine DNase1L3 (O55070):
Amino acid sequence
(Signal Peptide; Mature Protein):
                                SEQ ID NO: 31
MSLHPASPRLASLLLFILALHDTLALR

LCSFNVRSFGASKKENHEAMDIIVKII

KRCDLILLMEIKDSSNNICPMLMEKLN

GNSRRSTTYNYVISSRLGRNTYKEQYA

FVYKEKLVSVKTKYHYDYQDGDTDVF
```

```
SREPFVVWFHSPFTAVKDFVIVPLHTT

PETSVKEIDELVDVYTDVRSQWKTENF

IFMGDFNAGCSYVPKKAWQNIRLRTDP

KFVWLIGDQEDTTVKKSTSCAYDRIVL

CGQEIVNSVVPRSSGVFDFQKAYDLSE

EEALDVSDHFPVEFKLQSSRAFTNNRK

SVSLKKRKKGNRS

Rat DNase1L3 (O89107):
Amino acid sequence
(Signal Peptide; Mature Protein):
                                SEQ ID NO: 32
MSLYPASPYLASLLLFILALHGALSLR

LCSFNVRSFGESKKENHNAMDIIVKII

KRCDLILLMEIKDSNNNICPMLMEKLN

GNSRRSTTYNYVISSRLGRNTYKEQYA

FLYKEKLVSVKAKYLYHDYQDGDTDVF

SREPFVVWFQAPFTAAKDFVIVPLHTT

PETSVKEIDELADVYTDVRRRWKAENF

IFMGDFNAGCSYVPKKAWKNIRLRTDP

NFVWLIGDQEDTTVKKSTSCAYDRIVL

RGQEIVNSVVPRSSGVFDFQKAYELSE

EEALDVSDHFPVEFKLQSSRAFTNSRK

SVSLKKKKKGSRS

Chimpanzee DNase1L3 (H2QMU7):
Amino acid sequence
(Signal Peptide;
Mature Protein):
                                SEQ ID NO: 33
MSRELTPLLLLLLSIHSTLALRICSFN

VRSFGESKQEDQNAMDVIVKVIKRCDI

ILVMEIKDSNNRICPILMEKLNRNSRR

GITYNYVISSRLGRNTYKEQYAFLYKE

KLVSVKRSYHYDYQDGDADVFSREPF

VVWFQSPHTAVKDFVIIPLHTTPETSV

KEIDELVEVYTDVKHRWKAENFIFMGD

FNAGCSYVPKKAWKNIRLRTDPRFVWL

IGDQEDTTVKKSINCAYDRIVLRGQEI

VSSVVPKSNSVFDFQKAYKLTEEEALD

VSDHFPVEFKLQSSRAFTNSKKSVTLR

KKTKSKRS

Olive baboon DNase1L3 (A0A2I3NFJ3):
Amino acid sequence
(Signal Peptide; Mature
Protein):
                                SEQ ID NO: 34
MSQELAPLLLLLLSIHSALALRICSFN

VRSFGESKQEDQNAMDVIVKVIKRCDI

MLLMEIKDSNNRICPVLMEKLNGNSRR
```

GIMYNYVISSRLGRNTYKEQYAFLYKE

KLVSVKRSYHYHDYQDGDVDVFSREPF

VVWFQSPHTAVKDFVIIPLHTTPETSV

KEIDELVDVYMDMKHRWKAENFIFMGD

FNAGCSYVPKKAWKNIRLRTDPRFVWL

IGDQEDTTVKRSTKCAYDRIVLRGQEI

VSSVVPKSNSVFDFQKAYKLTEEEALD

VSDHFPVEFKLQSSRAFTNSKKSVTVR

KKTKSKRS

Rabbit DNase1L3 (A0A2I3NFJ3):
Amino acid sequence
(Signal Peptide; Mature
Protein):
SEQ ID NO: 35

MSLGMSPASLLLLLLCLHGALALKLCS

FNVRSFGYSKRENRQAMDVIVKIIKRC

DIILLMEIKDSNNMICPTLMEKLNGNS

RRGITYNYVISSRLGRNVYKEQYAFLY

KEKLVTVKKNYLYHDYEAGDADAFSRE

PYVVWFQSPFTAVKDFVIVPLHTSPEA

SVKEIDELVDVYMDVKRRWNAENFIFM

GDFNAGCSYVPKKAWKNIRLRTDPRFV

WLIGDEEDTTVKKSTSCAYDRIVLRGQ

DIIRSVVPDSNGVFDFRKAYKLTEEEA

LDVSDHFPVEFKLQSSTAFTNSKKSVQ

PRKKAKAKRS

Dog DNase1L3 (F1P9C1):
Amino acid sequence (Signal
Peptide; Mature Protein):
SEQ ID NO: 36

MPRLPAFLLFLLLSISSALALRLCSFN

VRSFGGAKRENKNAMDVIVKVIKRCDI

ILLMEVKDSNNMICPTLLEKLNGNSRR

GIKYNYVISSRLGRNTYKEQYAFLYKE

KLVSVKKYYLYHDYQAGDADVFSREPF

VVWFQSPFTAVKDFVIVPLHTTPEASV

KEIDELVDVYLDVKRRWKAENFIFMGD

FNAGCSYVPKKAWKIIRLRTDPGFVWL

IGDQEDTTVKSSTHCAYDRIVLRGPEI

IRSVVPRSNSTFDFQKAFLLTEEEALN

VSDHFPVEFKLQSSRAFTNSKKSISPK

KKKVRHP

Pig DNase1L3 (A0A287B132):
Amino acid sequence (predicted
Signal Peptide; Mature Protein):
SEQ ID NO: 37

MSQLLVSLMLLLLSTHSSLALRICSFN

VRSFGESKKANCNAMDVIVKVIKRCDI

ILLMEIKDSNNMICPTLMEKLNGNSRR

SVTYNYVISSRLGRNTYKEQYAFLYKE

KLVSVKKSYLYHDYQSGDADVFSREPF

VVWFQSPYTAVKDFVIIPLHTTPETSV

KEIDELVDVYLDVKRRWEAENFIFMGD

FNAGCSYVPKKAWKNIRLRTDPMFIWL

IKDQEDTTVKKSINCAYDRIVLRGQEI

VSSVVPGSNSIFDFQKAYRLTEEKVRL

SFCLSVSPSGEDGVVSPRGIQATTGDT

LGHLTLSFKANDSLT

Guinea pig DNase1L3 (A0A286XK50):
Amino acid sequence
(Signal Peptide; Mature
Protein):
SEQ ID NO: 38

MSQTRPSLLLLLLAIHGALALKLCSFN

VRSFGESKKQNQNAMDVIVKIIKRCDL

MLLMEIKDSHNRICPMLMEKLNGNSRR

GTTYNYVISSRLGRNTYKEQYAFLYKE

KLVTVKDNYLFHDEDADVFSREPYVVW

FQSPHTAVKDFVIVPLHTTPETSVKEI

DELADVYTDVQRQWKVANFIFMGDFNA

GCSYVPKKAWKNIRLRTDPKFVWLIAD

DEDTTVKKSTSCAYDRIVLRGQEIVNS

VVPNSNGVFDFQKAYQLSEEQALEVSD

HFPVEFKLQSERAFTNNKKSVSLKKKK

KANRS

Cow DNase1L3 (F1MGQ1):
Amino acid sequence (Signal
Peptide; Mature Protein):
SEQ ID NO: 39

MPLPLACLLLLLLSTHSALALKICSFN

VRSFGESKKANCNAMDVIVKVIKRCDI

ILLMEIKDSSNRICPTLMEKLNGNSRK

GITYNYVISSRLGRNTYKEQYAFLYKE

KLVSVKQSYLYHDYQAGDADVFSREPF

VVWFQSPYTAVKDFVIVPLHTTPETSV

REIDELADVYTDVKRRWNAENFIFMGD

FNAGCSYVPKKAWKDIRLRTDPKFVWL

IGDQEDTTVKKSINCAYDRIVLRGQNI

VNSVVPQSNLVFDFQKAYRLSESKALD

VSDHFPVEFKLQSSRAFTNSKKSVSSK

KKKKTSHA

Elephant DNase1L3 (G3SXX1):
Amino acid sequence
(Signal Peptide; Mature Protein):
SEQ ID NO: 40

RSARMSQSLPALLLLLLLSVHGTLALR

VCSFNVRSFGETKRENQKVMDIIVKII

KRCDIMLLMEIKDSNNRICPMLLKRLN

GNSRRGIKYNYVISPRLGRNAYKEQYA

FLYMEKLLSVKKSYVYGDNQNGDADVF

SREPFVTWFQSPHTAVKDFVIVPLHTT

PETSIKEIDELVDVYMDVKKRWNAQNF

IFMGDFNAGCSYVPKKSWRNIRLRTDP

GFVWLIGDQEDTTVKESTNCAYDRIVL

RGQIISSVVPNSNSIFNFQKAYELSEE

EALNISDHFPVEFKLQSSRAIINSKKS

VSPKKKKKAKSS

LINKER SEQUENCES

SEQ ID NO: 41
GGGGS

SEQ ID NO: 42
GGGGSGGGGSGGGGS

SEQ ID NO: 43
APAPAPAPAPAPAP

SEQ ID NO: 44
AEAAAKEAAAKA

SEQ ID NO: 45
SGGSGSS

SEQ ID NO: 46
SGGSGGSGGSGGSGSS

SEQ ID NO: 47
SGGSGGSGGSGGSGGSGGSGGSGGSG

GSGS

SEQ ID NO: 48
GGSGGSGGSGGSGGSGGSGGSGGSGG

SGS

ACTIVATABLE LINKER SEQUENCES
FXIIa-susceptible linker
(Factor XI peptide):
SEQ ID NO: 49
CTTKIKPRIVGGTASVRGEWPWQVT FXIIa-susceptible linker
(Prekallikrein peptide):
SEQ ID NO: 50
STRIVGG FXIIa-susceptible linker
(Prekallikrein peptide):
SEQ ID NO: 51
VCTIKTSTRIVGGINSSWGEWPWQVS

---

What is claimed is:

1. A method for treating a subject in need of extracellular DNA degradation, extracellular chromatin degradation, extracellular trap (ET) degradation and/or neutrophil extracellular trap (NET) degradation, the method comprising administering a therapeutically effective amount of a DNASE enzyme comprising an amino acid sequence that has at least 90% sequence identity to SEQ ID NO: 4, and having one or more amino acid substitutions of the C-terminal tail defined by SEQ ID NO: 10, and a C-terminal fusion to a carrier protein optionally through a linking sequence.

2. The method of claim 1, wherein the DNASE enzyme has at least two amino acid substitutions in the C-terminal tail.

3. The method of claim 1, wherein the DNASE enzyme has at least five amino acid substitutions in the C-terminal tail.

4. The method of claim 1, wherein the DNASE enzyme has one or more amino acid substitutions of the C-terminal tail selected from: S282E, R285T, F287I, S290N, K291R, V294I, T295S, T295Q, L296V, L296P, L296S, R297K, K299R, T300K, T300A, S302G, S302A, S302V, S302T, K303N, K303S, K303R, R304H, R304S, S305P, S305T, and S305A.

5. The method of claim 1, wherein the DNASE enzyme has one or more amino acid substitutions of the C-terminal tail selected from:
 (a) V294I;
 (b) T295S and T295Q;
 (c) L296V, L296P, and L296S;
 (d) R297K;
 (e) K299R;
 (f) T300K;
 (g) S302G, S302A, S302V, and S302T;
 (h) K303N, K303S, and K303R;
 (i) R304H and R304S; and
 (j) S305P, S305T, and S305A.

6. The method of claim 4, wherein the DNASE enzyme has one or more amino acid substitutions of the C-terminal tail selected from K303N and K303S.

7. The method of claim 1, further comprising the deletion of at least 3 amino acids of the C-terminal tail.

8. The method of claim 7, wherein at least 5 amino acids of the C-terminal tail are deleted.

9. The method of claim 7, wherein at least 12 amino acids of the C-terminal tail are deleted.

10. The method of claim 1, wherein the carrier protein is albumin.

11. The method of claim 1, wherein the carrier protein is an Fc domain.

12. The method of claim 2, wherein the linking sequence is a flexible linker.

13. The method of claim 12, wherein the linking sequence is composed predominately of Gly and/or Ser residues.

14. The method of claim 2, wherein the linking sequence is a rigid linker.

15. The method of claim 14, wherein the linking sequence comprises Pro or Pro-Ala motifs.

16. The method of claim 14, wherein the linking sequence is an α-helical linker.

17. The method of claim 1, wherein the DNASE enzyme exhibits protease resistance.

18. The method of claim 1, wherein the DNASE enzyme is administered by parenteral administration.

19. The method of claim 18, wherein the DNASE enzyme is administered by a route selected from intradermal, intramuscular, intraperitoneal, intraarticular, intravenous, and subcutaneous administration.

20. The method of claim 1, wherein the subject has a chronic or acute inflammatory disorder.

21. The method of claim 20, wherein the subject has an acute or chronic infection.

22. The method of claim 1, wherein the subject has neutrophilia.

23. The method of claim 1, wherein the subject has thrombosis or vascular occlusion.

24. The method of claim 1, wherein the subject has an autoimmune disease.

25. The method of claim 24, wherein the subject has systemic lupus erythematosus (SLE), lupus nephritis, rheumatoid arthritis, vasculitis, or systemic sclerosis.

26. The method of claim 1, wherein the subject has diabetes mellitus.

27. The method of claim 1, wherein the subject has sepsis.

28. The method of claim 1, wherein the subject has an inflammatory disease of the respiratory tract.

29. The method of claim 1, wherein the subject has a renal inflammatory disease, inflammatory disease related to transplated tissue, or cancer.

30. The method of claim 1, wherein the subject has or is at risk of Nets occluding ductural systems.

* * * * *

SEQUENCE LISTING

<160> NUMBER OF SEQ ID NOS: 51

<210> SEQ ID NO 1
<211> LENGTH: 282
<212> TYPE: PRT
<213> ORGANISM: Homo sapiens

<400> SEQUENCE: 1

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
            275                 280

<210> SEQ ID NO 2
<211> LENGTH: 302
<212> TYPE: PRT
<213> ORGANISM: Homo sapiens

<400> SEQUENCE: 2

Met His Tyr Pro Thr Ala Leu Leu Phe Leu Ile Leu Ala Asn Gly Ala
1               5                   10                  15

Gln Ala Phe Arg Ile Cys Ala Phe Asn Ala Gln Arg Leu Thr Leu Ala
                20                  25                  30

Lys Val Ala Arg Glu Gln Val Met Asp Thr Leu Val Arg Ile Leu Ala
            35                  40                  45

Arg Cys Asp Ile Met Val Leu Gln Glu Val Val Asp Ser Ser Gly Ser
        50                  55                  60

Ala Ile Pro Leu Leu Leu Arg Glu Leu Asn Arg Phe Asp Gly Ser Gly
65                  70                  75                  80

Pro Tyr Ser Thr Leu Ser Ser Pro Gln Leu Gly Arg Ser Thr Tyr Met
                85                  90                  95

Glu Thr Tyr Val Tyr Phe Tyr Arg Ser His Lys Thr Gln Val Leu Ser
                100                 105                 110

Ser Tyr Val Tyr Asn Asp Glu Asp Asp Val Phe Ala Arg Glu Pro Phe
            115                 120                 125

Val Ala Gln Phe Ser Leu Pro Ser Asn Val Leu Pro Ser Leu Val Leu
        130                 135                 140

Val Pro Leu His Thr Thr Pro Lys Ala Val Glu Lys Glu Leu Asn Ala
145                 150                 155                 160

Leu Tyr Asp Val Phe Leu Glu Val Ser Gln His Trp Gln Ser Lys Asp
                165                 170                 175

Val Ile Leu Leu Gly Asp Phe Asn Ala Asp Cys Ala Ser Leu Thr Lys
            180                 185                 190

Lys Arg Leu Asp Lys Leu Glu Leu Arg Thr Glu Pro Gly Phe His Trp
        195                 200                 205

Val Ile Ala Asp Gly Glu Asp Thr Thr Val Arg Ala Ser Thr His Cys
    210                 215                 220

Thr Tyr Asp Arg Val Val Leu His Gly Glu Arg Cys Arg Ser Leu Leu

```
225                 230                 235                 240

His Thr Ala Ala Ala Phe Asp Phe Pro Thr Ser Phe Gln Leu Thr Glu
                245                 250                 255

Glu Glu Ala Leu Asn Ile Ser Asp His Tyr Pro Val Glu Val Glu Leu
            260                 265                 270

Lys Leu Ser Gln Ala His Ser Val Gln Pro Leu Ser Leu Thr Val Leu
        275                 280                 285

Leu Leu Leu Ser Leu Leu Ser Pro Gln Leu Cys Pro Ala Ala
    290                 295                 300

<210> SEQ ID NO 3
<211> LENGTH: 299
<212> TYPE: PRT
<213> ORGANISM: Homo sapiens

<400> SEQUENCE: 3

Met Gly Gly Pro Arg Ala Leu Leu Ala Leu Trp Ala Leu Glu Ala
1               5                   10                  15

Ala Gly Thr Ala Ala Leu Arg Ile Gly Ala Phe Asn Ile Gln Ser Phe
            20                  25                  30

Gly Asp Ser Lys Val Ser Asp Pro Ala Cys Gly Ser Ile Ile Ala Lys
        35                  40                  45

Ile Leu Ala Gly Tyr Asp Leu Ala Leu Val Gln Glu Val Arg Asp Pro
    50                  55                  60

Asp Leu Ser Ala Val Ser Ala Leu Met Glu Gln Ile Asn Ser Val Ser
65                  70                  75                  80

Glu His Glu Tyr Ser Phe Val Ser Ser Gln Pro Leu Gly Arg Asp Gln
                85                  90                  95

Tyr Lys Glu Met Tyr Leu Phe Val Tyr Arg Lys Asp Ala Val Ser Val
            100                 105                 110

Val Asp Thr Tyr Leu Tyr Pro Asp Pro Glu Asp Val Phe Ser Arg Glu
        115                 120                 125

Pro Phe Val Val Lys Phe Ser Ala Pro Gly Thr Gly Glu Arg Ala Pro
    130                 135                 140

Pro Leu Pro Ser Arg Arg Ala Leu Thr Pro Pro Pro Leu Pro Ala Ala
145                 150                 155                 160

Ala Gln Asn Leu Val Leu Ile Pro Leu His Ala Ala Pro His Gln Ala
                165                 170                 175

Val Ala Glu Ile Asp Ala Leu Tyr Asp Val Tyr Leu Asp Val Ile Asp
            180                 185                 190

Lys Trp Gly Thr Asp Asp Met Leu Phe Leu Gly Asp Phe Asn Ala Asp
        195                 200                 205

Cys Ser Tyr Val Arg Ala Gln Asp Trp Ala Ala Ile Arg Leu Arg Ser
    210                 215                 220

Ser Glu Val Phe Lys Trp Leu Ile Pro Asp Ser Ala Asp Thr Thr Val
225                 230                 235                 240

Gly Asn Ser Asp Cys Ala Tyr Asp Arg Ile Val Ala Cys Gly Ala Arg
                245                 250                 255

Leu Arg Arg Ser Leu Lys Pro Gln Ser Ala Thr Val His Asp Phe Gln
            260                 265                 270

Glu Glu Phe Gly Leu Asp Gln Thr Gln Ala Leu Ala Ile Ser Asp His
        275                 280                 285

Phe Pro Val Glu Val Thr Leu Lys Phe His Arg
    290                 295
```

<210> SEQ ID NO 4
<211> LENGTH: 305
<212> TYPE: PRT
<213> ORGANISM: Homo sapiens

<400> SEQUENCE: 4

```
Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
290                 295                 300

Ser
305
```

<210> SEQ ID NO 5
<211> LENGTH: 275
<212> TYPE: PRT
<213> ORGANISM: Homo sapiens

<400> SEQUENCE: 5

```
Met Ser Arg Glu Leu Ala Pro Leu Leu Leu Leu Leu Ser Ile His
1               5                   10                  15
```

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
 50                  55                  60

Asn Arg Ile Cys Pro Ile Leu Met Glu Lys Leu Asn Arg Glu Lys Leu
65                  70                  75                  80

Val Ser Val Lys Arg Ser Tyr His Tyr His Asp Tyr Gln Asp Gly Asp
                85                  90                  95

Ala Asp Val Phe Ser Arg Glu Pro Phe Val Val Trp Phe Gln Ser Pro
            100                 105                 110

His Thr Ala Val Lys Asp Phe Val Ile Ile Pro Leu His Thr Thr Pro
        115                 120                 125

Glu Thr Ser Val Lys Glu Ile Asp Glu Leu Val Glu Val Tyr Thr Asp
130                 135                 140

Val Lys His Arg Trp Lys Ala Glu Asn Phe Ile Phe Met Gly Asp Phe
145                 150                 155                 160

Asn Ala Gly Cys Ser Tyr Val Pro Lys Lys Ala Trp Lys Asn Ile Arg
                165                 170                 175

Leu Arg Thr Asp Pro Arg Phe Val Trp Leu Ile Gly Asp Gln Glu Asp
            180                 185                 190

Thr Thr Val Lys Lys Ser Thr Asn Cys Ala Tyr Asp Arg Ile Val Leu
        195                 200                 205

Arg Gly Gln Glu Ile Val Ser Ser Val Val Pro Lys Ser Asn Ser Val
210                 215                 220

Phe Asp Phe Gln Lys Ala Tyr Lys Leu Thr Glu Glu Ala Leu Asp
225                 230                 235                 240

Val Ser Asp His Phe Pro Val Glu Phe Lys Leu Gln Ser Ser Arg Ala
                245                 250                 255

Phe Thr Asn Ser Lys Lys Ser Val Thr Leu Arg Lys Lys Thr Lys Ser
            260                 265                 270

Lys Arg Ser
        275

<210> SEQ ID NO 6
<211> LENGTH: 360
<212> TYPE: PRT
<213> ORGANISM: Homo sapiens

<400> SEQUENCE: 6

Met Ile Pro Leu Leu Ala Ala Leu Leu Cys Val Pro Ala Gly Ala
1               5                   10                  15

Leu Thr Cys Tyr Gly Asp Ser Gly Gln Pro Val Asp Trp Phe Val Val
            20                  25                  30

Tyr Lys Leu Pro Ala Leu Arg Gly Ser Gly Glu Ala Ala Gln Arg Gly
        35                  40                  45

Leu Gln Tyr Lys Tyr Leu Asp Glu Ser Ser Gly Gly Trp Arg Asp Gly
    50                  55                  60

Arg Ala Leu Ile Asn Ser Pro Glu Gly Ala Val Gly Arg Ser Leu Gln
65                  70                  75                  80

Pro Leu Tyr Arg Ser Asn Thr Ser Gln Leu Ala Phe Leu Leu Tyr Asn
                85                  90                  95

Asp Gln Pro Pro Gln Pro Ser Lys Ala Gln Asp Ser Ser Met Arg Gly
            100                 105                 110

His Thr Lys Gly Val Leu Leu Asp His Asp Gly Phe Trp Leu
            115                 120                 125

Val His Ser Val Pro Asn Phe Pro Pro Ala Ser Ser Ala Ala Tyr
    130                 135                 140

Ser Trp Pro His Ser Ala Cys Thr Tyr Gly Gln Thr Leu Leu Cys Val
145                 150                 155                 160

Ser Phe Pro Phe Ala Gln Phe Ser Lys Met Gly Lys Gln Leu Thr Tyr
                165                 170                 175

Thr Tyr Pro Trp Val Tyr Asn Tyr Gln Leu Glu Gly Ile Phe Ala Gln
            180                 185                 190

Glu Phe Pro Asp Leu Glu Asn Val Val Lys Gly His His Val Ser Gln
        195                 200                 205

Glu Pro Trp Asn Ser Ser Ile Thr Leu Thr Ser Gln Ala Gly Ala Val
    210                 215                 220

Phe Gln Ser Phe Ala Lys Phe Ser Lys Phe Gly Asp Asp Leu Tyr Ser
225                 230                 235                 240

Gly Trp Leu Ala Ala Ala Leu Gly Thr Asn Leu Gln Val Gln Phe Trp
                245                 250                 255

His Lys Thr Val Gly Ile Leu Pro Ser Asn Cys Ser Asp Ile Trp Gln
            260                 265                 270

Val Leu Asn Val Asn Gln Ile Ala Phe Pro Gly Pro Ala Gly Pro Ser
        275                 280                 285

Phe Asn Ser Thr Glu Asp His Ser Lys Trp Cys Val Ser Pro Lys Gly
    290                 295                 300

Pro Trp Thr Cys Val Gly Asp Met Asn Arg Asn Gln Gly Glu Glu Gln
305                 310                 315                 320

Arg Gly Gly Gly Thr Leu Cys Ala Gln Leu Pro Ala Leu Trp Lys Ala
                325                 330                 335

Phe Gln Pro Leu Val Lys Asn Tyr Gln Pro Cys Asn Gly Met Ala Arg
            340                 345                 350

Lys Pro Ser Arg Ala Tyr Lys Ile
        355                 360

<210> SEQ ID NO 7
<211> LENGTH: 361
<212> TYPE: PRT
<213> ORGANISM: Homo sapiens

<400> SEQUENCE: 7

Met Lys Gln Lys Met Met Ala Arg Leu Leu Arg Thr Ser Phe Ala Leu
1               5                   10                  15

Leu Phe Leu Gly Leu Phe Gly Val Leu Gly Ala Ala Thr Ile Ser Cys
                20                  25                  30

Arg Asn Glu Glu Gly Lys Ala Val Asp Trp Phe Thr Phe Tyr Lys Leu
            35                  40                  45

Pro Lys Arg Gln Asn Lys Glu Ser Gly Glu Thr Gly Leu Glu Tyr Leu
        50                  55                  60

Tyr Leu Asp Ser Thr Thr Arg Ser Trp Arg Lys Ser Glu Gln Leu Met
65                  70                  75                  80

Asn Asp Thr Lys Ser Val Leu Gly Arg Thr Leu Gln Gln Leu Tyr Glu
                85                  90                  95

Ala Tyr Ala Ser Lys Ser Asn Asn Thr Ala Tyr Leu Ile Tyr Asn Asp
            100                 105                 110

Gly Val Pro Lys Pro Val Asn Tyr Ser Arg Lys Tyr Gly His Thr Lys

```
            115                 120                 125
Gly Leu Leu Leu Trp Asn Arg Val Gln Gly Phe Trp Leu Ile His Ser
    130                 135                 140

Ile Pro Gln Phe Pro Pro Ile Pro Glu Glu Gly Tyr Asp Tyr Pro Pro
145                 150                 155                 160

Thr Gly Arg Arg Asn Gly Gln Ser Gly Ile Cys Ile Thr Phe Lys Tyr
                165                 170                 175

Asn Gln Tyr Glu Ala Ile Asp Ser Gln Leu Leu Val Cys Asn Pro Asn
            180                 185                 190

Val Tyr Ser Cys Ser Ile Pro Ala Thr Phe His Gln Glu Leu Ile His
        195                 200                 205

Met Pro Gln Leu Cys Thr Arg Ala Ser Ser Glu Ile Pro Gly Arg
    210                 215                 220

Leu Leu Thr Thr Leu Gln Ser Ala Gln Gly Lys Phe Leu His Phe
225                 230                 235                 240

Ala Lys Ser Asp Ser Phe Leu Asp Asp Ile Phe Ala Ala Trp Met Ala
                245                 250                 255

Gln Arg Leu Lys Thr His Leu Leu Thr Glu Thr Trp Gln Arg Lys Arg
            260                 265                 270

Gln Glu Leu Pro Ser Asn Cys Ser Leu Pro Tyr His Val Tyr Asn Ile
        275                 280                 285

Lys Ala Ile Lys Leu Ser Arg His Ser Tyr Phe Ser Tyr Gln Asp
    290                 295                 300

His Ala Lys Trp Cys Ile Ser Gln Lys Gly Thr Lys Asn Arg Trp Thr
305                 310                 315                 320

Cys Ile Gly Asp Leu Asn Arg Ser Pro His Gln Ala Phe Arg Ser Gly
                325                 330                 335

Gly Phe Ile Cys Thr Gln Asn Trp Gln Ile Tyr Gln Ala Phe Gln Gly
            340                 345                 350

Leu Val Leu Tyr Tyr Glu Ser Cys Lys
        355                 360

<210> SEQ ID NO 8
<211> LENGTH: 30
<212> TYPE: PRT
<213> ORGANISM: Homo sapiens

<400> SEQUENCE: 8

Lys Leu Ser Gln Ala His Ser Val Gln Pro Leu Ser Leu Thr Val Leu
1               5                   10                  15

Leu Leu Leu Ser Leu Leu Ser Pro Gln Leu Cys Pro Ala Ala
            20                  25                  30

<210> SEQ ID NO 9
<211> LENGTH: 35
<212> TYPE: PRT
<213> ORGANISM: Homo sapiens

<400> SEQUENCE: 9

Ser Ala Pro Gly Thr Gly Glu Arg Ala Pro Pro Leu Pro Ser Arg Arg
1               5                   10                  15

Ala Leu Thr Pro Pro Pro Leu Pro Ala Ala Ala Gln Asn Leu Val Leu
            20                  25                  30

Ile Pro Leu
        35
```

<210> SEQ ID NO 10
<211> LENGTH: 23
<212> TYPE: PRT
<213> ORGANISM: Homo sapiens

<400> SEQUENCE: 10

Ser Ser Arg Ala Phe Thr Asn Ser Lys Lys Ser Val Thr Leu Arg Lys
1               5                   10                  15

Lys Thr Lys Ser Lys Arg Ser
            20

<210> SEQ ID NO 11
<211> LENGTH: 31
<212> TYPE: PRT
<213> ORGANISM: Homo sapiens

<400> SEQUENCE: 11

Arg Asn Ser Arg Arg Gly Ile Thr Tyr Asn Tyr Val Ile Ser Ser Arg
1               5                   10                  15

Leu Gly Arg Asn Thr Tyr Lys Glu Gln Tyr Ala Phe Leu Tyr Lys
            20                  25                  30

<210> SEQ ID NO 12
<211> LENGTH: 609
<212> TYPE: PRT
<213> ORGANISM: Homo sapiens

<400> SEQUENCE: 12

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

```
Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
        260                 265                 270

Asp Leu Leu Glu Cys Ala Asp Asp Arg Ala Asp Leu Ala Lys Tyr Ile
    275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu
```

<210> SEQ ID NO 13
<211> LENGTH: 884
<212> TYPE: PRT
<213> ORGANISM: Artificial Sequence
<220> FEATURE:
<223> OTHER INFORMATION: Synethetic Sequence

<400> SEQUENCE: 13

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
```

```
                       405                 410                 415
Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
            450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
            595                 600                 605

Leu Gly Gly Gly Gly Ser Gly Gly Gly Ser Gly Gly Gly Gly Ser
610                 615                 620

Leu Lys Ile Ala Ala Phe Asn Ile Gln Thr Phe Gly Glu Thr Lys Met
625                 630                 635                 640

Ser Asn Ala Thr Leu Val Ser Tyr Ile Val Gln Ile Leu Ser Arg Tyr
                645                 650                 655

Asp Ile Ala Leu Val Gln Glu Val Arg Asp Ser His Leu Thr Ala Val
                660                 665                 670

Gly Lys Leu Leu Asp Asn Leu Asn Gln Asp Ala Pro Asp Thr Tyr His
            675                 680                 685

Tyr Val Val Ser Glu Pro Leu Gly Arg Asn Ser Tyr Lys Glu Arg Tyr
            690                 695                 700

Leu Phe Val Tyr Arg Pro Asp Gln Val Ser Ala Val Asp Ser Tyr Tyr
705                 710                 715                 720

Tyr Asp Asp Gly Cys Glu Pro Cys Gly Asn Asp Thr Phe Asn Arg Glu
                725                 730                 735

Pro Ala Ile Val Arg Phe Phe Ser Arg Phe Thr Glu Val Arg Glu Phe
                740                 745                 750

Ala Ile Val Pro Leu His Ala Ala Pro Gly Asp Ala Val Ala Glu Ile
            755                 760                 765

Asp Ala Leu Tyr Asp Val Tyr Leu Asp Val Gln Glu Lys Trp Gly Leu
            770                 775                 780

Glu Asp Val Met Leu Met Gly Asp Phe Asn Ala Gly Cys Ser Tyr Val
785                 790                 795                 800

Arg Pro Ser Gln Trp Ser Ser Ile Arg Leu Trp Thr Ser Pro Thr Phe
                805                 810                 815

Gln Trp Leu Ile Pro Asp Ser Ala Asp Thr Thr Ala Thr Pro Thr His
            820                 825                 830
```

```
Cys Ala Tyr Asp Arg Ile Val Val Ala Gly Met Leu Leu Arg Gly Ala
            835                 840                 845

Val Val Pro Asp Ser Ala Leu Pro Phe Asn Phe Gln Ala Ala Tyr Gly
850                 855                 860

Leu Ser Asp Gln Leu Ala Gln Ala Ile Ser Asp His Tyr Pro Val Glu
865                 870                 875                 880

Val Met Leu Lys

<210> SEQ ID NO 14
<211> LENGTH: 908
<212> TYPE: PRT
<213> ORGANISM: Artificial Sequence
<220> FEATURE:
<223> OTHER INFORMATION: Synethetic Sequence

<400> SEQUENCE: 14

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300
```

-continued

```
Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
                355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
                435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu Gly Gly Gly Ser Gly Gly Gly Ser Gly Gly Gly Ser
    610                 615                 620

Phe Arg Ile Cys Ala Phe Asn Ala Gln Arg Leu Thr Leu Ala Lys Val
625                 630                 635                 640

Ala Arg Glu Gln Val Met Asp Thr Leu Val Arg Ile Leu Ala Arg Cys
                645                 650                 655

Asp Ile Met Val Leu Gln Glu Val Val Asp Ser Ser Gly Ser Ala Ile
                660                 665                 670

Pro Leu Leu Leu Arg Glu Leu Asn Arg Phe Asp Gly Ser Gly Pro Tyr
                675                 680                 685

Ser Thr Leu Ser Ser Pro Gln Leu Gly Arg Ser Thr Tyr Met Glu Thr
    690                 695                 700

Tyr Val Tyr Phe Tyr Arg Ser His Lys Thr Gln Val Leu Ser Ser Tyr
705                 710                 715                 720

Val Tyr Asn Asp Glu Asp Asp Val Phe Ala Arg Glu Pro Phe Val Ala
```

```
                        725                 730                 735
Gln Phe Ser Leu Pro Ser Asn Val Leu Pro Ser Leu Val Leu Val Pro
            740                 745                 750
Leu His Thr Thr Pro Lys Ala Val Glu Lys Glu Leu Asn Ala Leu Tyr
            755                 760                 765
Asp Val Phe Leu Glu Val Ser Gln His Trp Gln Ser Lys Asp Val Ile
            770                 775                 780
Leu Leu Gly Asp Phe Asn Ala Asp Cys Ala Ser Leu Thr Lys Lys Arg
785                 790                 795                 800
Leu Asp Lys Leu Glu Leu Arg Thr Glu Pro Gly Phe His Trp Val Ile
                805                 810                 815
Ala Asp Gly Glu Asp Thr Thr Val Arg Ala Ser Thr His Cys Thr Tyr
            820                 825                 830
Asp Arg Val Val Leu His Gly Glu Arg Cys Arg Ser Leu Leu His Thr
            835                 840                 845
Ala Ala Ala Phe Asp Phe Pro Thr Ser Phe Gln Leu Thr Glu Glu Glu
            850                 855                 860
Ala Leu Asn Ile Ser Asp His Tyr Pro Val Glu Val Glu Leu Lys Leu
865                 870                 875                 880
Ser Gln Ala His Ser Val Gln Pro Leu Ser Leu Thr Val Leu Leu Leu
                885                 890                 895
Leu Ser Leu Leu Ser Pro Gln Leu Cys Pro Ala Ala
            900                 905

<210> SEQ ID NO 15
<211> LENGTH: 902
<212> TYPE: PRT
<213> ORGANISM: Artificial Sequence
<220> FEATURE:
<223> OTHER INFORMATION: Synethetic Sequence

<400> SEQUENCE: 15

Met Lys Trp Val Thr Phe Ile Ser Leu Leu Phe Leu Phe Ser Ser Ala
1               5                   10                  15
Tyr Ser Arg Gly Val Phe Arg Arg Asp Ala His Lys Ser Glu Val Ala
                20                  25                  30
His Arg Phe Lys Asp Leu Gly Glu Glu Asn Phe Lys Ala Leu Val Leu
            35                  40                  45
Ile Ala Phe Ala Gln Tyr Leu Gln Gln Cys Pro Phe Glu Asp His Val
        50                  55                  60
Lys Leu Val Asn Glu Val Thr Glu Phe Ala Lys Thr Cys Val Ala Asp
65                  70                  75                  80
Glu Ser Ala Glu Asn Cys Asp Lys Ser Leu His Thr Leu Phe Gly Asp
                85                  90                  95
Lys Leu Cys Thr Val Ala Thr Leu Arg Glu Thr Tyr Gly Glu Met Ala
            100                 105                 110
Asp Cys Cys Ala Lys Gln Glu Pro Glu Arg Asn Glu Cys Phe Leu Gln
        115                 120                 125
His Lys Asp Asp Asn Pro Asn Leu Pro Arg Leu Val Arg Pro Glu Val
    130                 135                 140
Asp Val Met Cys Thr Ala Phe His Asp Asn Glu Glu Thr Phe Leu Lys
145                 150                 155                 160
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
```

```
            180                 185                 190
Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
        260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
        340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
        420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
        500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
        580                 585                 590

Ala Glu Glu Gly Lys Lys Leu Val Ala Ala Ser Gln Ala Ala Leu Gly
        595                 600                 605
```

Leu Gly Gly Gly Ser Gly Gly Gly Ser Gly Gly Gly Ser
            610                 615                 620

Leu Arg Ile Gly Ala Phe Asn Ile Gln Ser Phe Gly Asp Ser Lys Val
625                 630                 635                 640

Ser Asp Pro Ala Cys Gly Ser Ile Ile Ala Lys Ile Leu Ala Gly Tyr
            645                 650                 655

Asp Leu Ala Leu Val Gln Glu Val Arg Asp Pro Asp Leu Ser Ala Val
            660                 665                 670

Ser Ala Leu Met Glu Gln Ile Asn Ser Val Ser Glu His Glu Tyr Ser
            675                 680                 685

Phe Val Ser Ser Gln Pro Leu Gly Arg Asp Gln Tyr Lys Glu Met Tyr
690                 695                 700

Leu Phe Val Tyr Arg Lys Asp Ala Val Ser Val Val Asp Thr Tyr Leu
705                 710                 715                 720

Tyr Pro Asp Pro Glu Asp Val Phe Ser Arg Glu Pro Phe Val Val Lys
            725                 730                 735

Phe Ser Ala Pro Gly Thr Gly Glu Arg Ala Pro Pro Leu Pro Ser Arg
            740                 745                 750

Arg Ala Leu Thr Pro Pro Leu Pro Ala Ala Ala Gln Asn Leu Val
            755                 760                 765

Leu Ile Pro Leu His Ala Ala Pro His Gln Ala Val Ala Glu Ile Asp
770                 775                 780

Ala Leu Tyr Asp Val Tyr Leu Asp Val Ile Asp Lys Trp Gly Thr Asp
785                 790                 795                 800

Asp Met Leu Phe Leu Gly Asp Phe Asn Ala Asp Cys Ser Tyr Val Arg
            805                 810                 815

Ala Gln Asp Trp Ala Ala Ile Arg Leu Arg Ser Ser Glu Val Phe Lys
            820                 825                 830

Trp Leu Ile Pro Asp Ser Ala Asp Thr Thr Val Gly Asn Ser Asp Cys
835                 840                 845

Ala Tyr Asp Arg Ile Val Ala Cys Gly Ala Arg Leu Arg Arg Ser Leu
            850                 855                 860

Lys Pro Gln Ser Ala Thr Val His Asp Phe Gln Glu Glu Phe Gly Leu
865                 870                 875                 880

Asp Gln Thr Gln Ala Leu Ala Ile Ser Asp His Phe Pro Val Glu Val
            885                 890                 895

Thr Leu Lys Phe His Arg
            900

<210> SEQ ID NO 16
<211> LENGTH: 909
<212> TYPE: PRT
<213> ORGANISM: Artificial Sequence
<220> FEATURE:
<223> OTHER INFORMATION: Synethetic Sequence

<400> SEQUENCE: 16

Met Lys Trp Val Thr Phe Ile Ser Leu Leu Phe Leu Phe Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

-continued

```
Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480
```

-continued

```
Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu Gly Gly Gly Gly Ser Gly Gly Gly Ser Gly Gly Gly Gly Ser
    610                 615                 620

Met Arg Ile Cys Ser Phe Asn Val Arg Ser Phe Gly Glu Ser Lys Gln
625                 630                 635                 640

Glu Asp Lys Asn Ala Met Asp Val Ile Val Lys Val Ile Lys Arg Cys
                645                 650                 655

Asp Ile Ile Leu Val Met Glu Ile Lys Asp Ser Asn Asn Arg Ile Cys
            660                 665                 670

Pro Ile Leu Met Glu Lys Leu Asn Arg Asn Ser Arg Arg Gly Ile Thr
        675                 680                 685

Tyr Asn Tyr Val Ile Ser Ser Arg Leu Gly Arg Asn Thr Tyr Lys Glu
    690                 695                 700

Gln Tyr Ala Phe Leu Tyr Lys Glu Lys Leu Val Ser Val Lys Arg Ser
705                 710                 715                 720

Tyr His Tyr His Asp Tyr Gln Asp Gly Asp Ala Asp Val Phe Ser Arg
                725                 730                 735

Glu Pro Phe Val Val Trp Phe Gln Ser Pro His Thr Ala Val Lys Asp
            740                 745                 750

Phe Val Ile Ile Pro Leu His Thr Thr Pro Glu Thr Ser Val Lys Glu
        755                 760                 765

Ile Asp Glu Leu Val Glu Val Tyr Thr Asp Val Lys His Arg Trp Lys
    770                 775                 780

Ala Glu Asn Phe Ile Phe Met Gly Asp Phe Asn Ala Gly Cys Ser Tyr
785                 790                 795                 800

Val Pro Lys Lys Ala Trp Lys Asn Ile Arg Leu Arg Thr Asp Pro Arg
                805                 810                 815

Phe Val Trp Leu Ile Gly Asp Gln Glu Asp Thr Thr Val Lys Lys Ser
            820                 825                 830

Thr Asn Cys Ala Tyr Asp Arg Ile Val Leu Arg Gly Gln Glu Ile Val
        835                 840                 845

Ser Ser Val Val Pro Lys Ser Asn Ser Val Phe Asp Phe Gln Lys Ala
    850                 855                 860

Tyr Lys Leu Thr Glu Glu Ala Leu Asp Val Ser Asp His Phe Pro
865                 870                 875                 880

Val Glu Phe Lys Leu Gln Ser Ser Arg Ala Phe Thr Asn Ser Lys Lys
                885                 890                 895

Ser Val Thr Leu Arg Lys Lys Thr Lys Ser Lys Arg Ser
```

<210> SEQ ID NO 17
<211> LENGTH: 879
<212> TYPE: PRT
<213> ORGANISM: Artificial Sequence
<220> FEATURE:
<223> OTHER INFORMATION: Synethetic Sequence

<400> SEQUENCE: 17

| | | | | | | | | | | | | | | |
|---|---|---|---|---|---|---|---|---|---|---|---|---|---|---|
| Met | Lys | Trp | Val | Thr | Phe | Ile | Ser | Leu | Leu | Phe | Leu | Phe | Ser | Ser | Ala |
| 1 | | | | 5 | | | | | 10 | | | | | 15 | |
| Tyr | Ser | Arg | Gly | Val | Phe | Arg | Arg | Asp | Ala | His | Lys | Ser | Glu | Val | Ala |
| | | | 20 | | | | | 25 | | | | | 30 | | |
| His | Arg | Phe | Lys | Asp | Leu | Gly | Glu | Glu | Asn | Phe | Lys | Ala | Leu | Val | Leu |
| | | | 35 | | | | | 40 | | | | | 45 | | |
| Ile | Ala | Phe | Ala | Gln | Tyr | Leu | Gln | Gln | Cys | Pro | Phe | Glu | Asp | His | Val |
| | | 50 | | | | | 55 | | | | | 60 | | | |
| Lys | Leu | Val | Asn | Glu | Val | Thr | Glu | Phe | Ala | Lys | Thr | Cys | Val | Ala | Asp |
| 65 | | | | | 70 | | | | | 75 | | | | | 80 |
| Glu | Ser | Ala | Glu | Asn | Cys | Asp | Lys | Ser | Leu | His | Thr | Leu | Phe | Gly | Asp |
| | | | | 85 | | | | | 90 | | | | | 95 | |
| Lys | Leu | Cys | Thr | Val | Ala | Thr | Leu | Arg | Glu | Thr | Tyr | Gly | Glu | Met | Ala |
| | | | 100 | | | | | 105 | | | | | 110 | | |
| Asp | Cys | Cys | Ala | Lys | Gln | Glu | Pro | Glu | Arg | Asn | Glu | Cys | Phe | Leu | Gln |
| | | | 115 | | | | | 120 | | | | | 125 | | |
| His | Lys | Asp | Asp | Asn | Pro | Asn | Leu | Pro | Arg | Leu | Val | Arg | Pro | Glu | Val |
| | | 130 | | | | | 135 | | | | | 140 | | | |
| Asp | Val | Met | Cys | Thr | Ala | Phe | His | Asp | Asn | Glu | Glu | Thr | Phe | Leu | Lys |
| 145 | | | | | 150 | | | | | 155 | | | | | 160 |
| Lys | Tyr | Leu | Tyr | Glu | Ile | Ala | Arg | Arg | His | Pro | Tyr | Phe | Tyr | Ala | Pro |
| | | | | 165 | | | | | 170 | | | | | 175 | |
| Glu | Leu | Leu | Phe | Phe | Ala | Lys | Arg | Tyr | Lys | Ala | Ala | Phe | Thr | Glu | Cys |
| | | | 180 | | | | | 185 | | | | | 190 | | |
| Cys | Gln | Ala | Ala | Asp | Lys | Ala | Ala | Cys | Leu | Leu | Pro | Lys | Leu | Asp | Glu |
| | | | 195 | | | | | 200 | | | | | 205 | | |
| Leu | Arg | Asp | Glu | Gly | Lys | Ala | Ser | Ser | Ala | Lys | Gln | Arg | Leu | Lys | Cys |
| | | 210 | | | | | 215 | | | | | 220 | | | |
| Ala | Ser | Leu | Gln | Lys | Phe | Gly | Glu | Arg | Ala | Phe | Lys | Ala | Trp | Ala | Val |
| 225 | | | | | 230 | | | | | 235 | | | | | 240 |
| Ala | Arg | Leu | Ser | Gln | Arg | Phe | Pro | Lys | Ala | Glu | Phe | Ala | Glu | Val | Ser |
| | | | | 245 | | | | | 250 | | | | | 255 | |
| Lys | Leu | Val | Thr | Asp | Leu | Thr | Lys | Val | His | Thr | Glu | Cys | Cys | His | Gly |
| | | | 260 | | | | | 265 | | | | | 270 | | |
| Asp | Leu | Leu | Glu | Cys | Ala | Asp | Asp | Arg | Ala | Asp | Leu | Ala | Lys | Tyr | Ile |
| | | | 275 | | | | | 280 | | | | | 285 | | |
| Cys | Glu | Asn | Gln | Asp | Ser | Ile | Ser | Ser | Lys | Leu | Lys | Glu | Cys | Cys | Glu |
| | | 290 | | | | | 295 | | | | | 300 | | | |
| Lys | Pro | Leu | Leu | Glu | Lys | Ser | His | Cys | Ile | Ala | Glu | Val | Glu | Asn | Asp |
| 305 | | | | | 310 | | | | | 315 | | | | | 320 |
| Glu | Met | Pro | Ala | Asp | Leu | Pro | Ser | Leu | Ala | Ala | Asp | Phe | Val | Glu | Ser |
| | | | | 325 | | | | | 330 | | | | | 335 | |
| Lys | Asp | Val | Cys | Lys | Asn | Tyr | Ala | Glu | Ala | Lys | Asp | Val | Phe | Leu | Gly |
| | | | 340 | | | | | 345 | | | | | 350 | | |
| Met | Phe | Leu | Tyr | Glu | Tyr | Ala | Arg | Arg | His | Pro | Asp | Tyr | Ser | Val | Val |

```
            355                 360                 365
Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu Gly Gly Gly Gly Ser Gly Gly Gly Gly Ser Gly Gly Gly Gly Ser
        610                 615                 620

Met Arg Ile Cys Ser Phe Asn Val Arg Ser Phe Gly Glu Ser Lys Gln
625                 630                 635                 640

Glu Asp Lys Asn Ala Met Asp Val Ile Val Lys Val Ile Lys Arg Cys
                645                 650                 655

Asp Ile Ile Leu Val Met Glu Ile Lys Asp Ser Asn Asn Arg Ile Cys
                660                 665                 670

Pro Ile Leu Met Glu Lys Leu Asn Arg Glu Lys Leu Val Ser Val Lys
            675                 680                 685

Arg Ser Tyr His Tyr His Asp Tyr Gln Asp Gly Asp Ala Asp Val Phe
        690                 695                 700

Ser Arg Glu Pro Phe Val Val Trp Phe Gln Ser Pro His Thr Ala Val
705                 710                 715                 720

Lys Asp Phe Val Ile Ile Pro Leu His Thr Thr Pro Glu Thr Ser Val
                725                 730                 735

Lys Glu Ile Asp Glu Leu Val Glu Val Tyr Thr Asp Val Lys His Arg
            740                 745                 750

Trp Lys Ala Glu Asn Phe Ile Phe Met Gly Asp Phe Asn Ala Gly Cys
        755                 760                 765

Ser Tyr Val Pro Lys Lys Ala Trp Lys Asn Ile Arg Leu Arg Thr Asp
        770                 775                 780
```

```
Pro Arg Phe Val Trp Leu Ile Gly Asp Gln Glu Asp Thr Thr Val Lys
785                 790                 795                 800

Lys Ser Thr Asn Cys Ala Tyr Asp Arg Ile Val Leu Arg Gly Gln Glu
            805                 810                 815

Ile Val Ser Ser Val Val Pro Lys Ser Asn Ser Val Phe Asp Phe Gln
            820                 825                 830

Lys Ala Tyr Lys Leu Thr Glu Glu Ala Leu Asp Val Ser Asp His
            835                 840                 845

Phe Pro Val Glu Phe Lys Leu Gln Ser Ser Arg Ala Phe Thr Asn Ser
850                 855                 860

Lys Lys Ser Val Thr Leu Arg Lys Lys Thr Lys Ser Lys Arg Ser
865                 870                 875

<210> SEQ ID NO 18
<211> LENGTH: 966
<212> TYPE: PRT
<213> ORGANISM: Artificial Sequence
<220> FEATURE:
<223> OTHER INFORMATION: Synethetic Sequence

<400> SEQUENCE: 18

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270
```

-continued

```
Asp Leu Leu Glu Cys Ala Asp Arg Ala Asp Leu Ala Lys Tyr Ile
        275                 280                 285
Cys Glu Asn Gln Asp Ser Ile Ser Ser Lys Leu Lys Glu Cys Cys Glu
290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
                340                 345                 350
Met Phe Leu Tyr Glu Tyr Ala Arg Arg His Pro Asp Tyr Ser Val Val
        355                 360                 365
Leu Leu Leu Arg Leu Ala Lys Thr Tyr Glu Thr Thr Leu Glu Lys Cys
        370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
                420                 425                 430
Val Arg Tyr Thr Lys Lys Val Pro Gln Val Ser Thr Pro Thr Leu Val
        435                 440                 445
Glu Val Ser Arg Asn Leu Gly Lys Val Gly Ser Lys Cys Cys Lys His
        450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
                500                 505                 510
Ser Ala Leu Glu Val Asp Glu Thr Tyr Val Pro Lys Glu Phe Asn Ala
        515                 520                 525
Glu Thr Phe Thr Phe His Ala Asp Ile Cys Thr Leu Ser Glu Lys Glu
        530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
                580                 585                 590
Ala Glu Glu Gly Lys Lys Leu Val Ala Ala Ser Gln Ala Ala Leu Gly
        595                 600                 605
Leu Gly Gly Gly Ser Gly Gly Gly Ser Gly Gly Gly Ser
        610                 615                 620
Cys Tyr Gly Asp Ser Gly Gln Pro Val Asp Trp Phe Val Val Tyr Lys
625                 630                 635                 640
Leu Pro Ala Leu Arg Gly Ser Gly Glu Ala Ala Gln Arg Gly Leu Gln
                645                 650                 655
Tyr Lys Tyr Leu Asp Glu Ser Ser Gly Gly Trp Arg Asp Gly Arg Ala
                660                 665                 670
Leu Ile Asn Ser Pro Glu Gly Ala Val Gly Arg Ser Leu Gln Pro Leu
        675                 680                 685
```

-continued

```
Tyr Arg Ser Asn Thr Ser Gln Leu Ala Phe Leu Leu Tyr Asn Asp Gln
690                 695                 700

Pro Pro Gln Pro Ser Lys Ala Gln Asp Ser Ser Met Arg Gly His Thr
705                 710                 715                 720

Lys Gly Val Leu Leu Leu Asp His Asp Gly Gly Phe Trp Leu Val His
            725                 730                 735

Ser Val Pro Asn Phe Pro Pro Ala Ser Ser Ala Ala Tyr Ser Trp
            740                 745                 750

Pro His Ser Ala Cys Thr Tyr Gly Gln Thr Leu Leu Cys Val Ser Phe
            755                 760                 765

Pro Phe Ala Gln Phe Ser Lys Met Gly Lys Gln Leu Thr Tyr Thr Tyr
770                 775                 780

Pro Trp Val Tyr Asn Tyr Gln Leu Glu Gly Ile Phe Ala Gln Glu Phe
785                 790                 795                 800

Pro Asp Leu Glu Asn Val Val Lys Gly His His Val Ser Gln Glu Pro
                805                 810                 815

Trp Asn Ser Ser Ile Thr Leu Thr Ser Gln Ala Gly Ala Val Phe Gln
                820                 825                 830

Ser Phe Ala Lys Phe Ser Lys Phe Gly Asp Asp Leu Tyr Ser Gly Trp
            835                 840                 845

Leu Ala Ala Ala Leu Gly Thr Asn Leu Gln Val Gln Phe Trp His Lys
850                 855                 860

Thr Val Gly Ile Leu Pro Ser Asn Cys Ser Asp Ile Trp Gln Val Leu
865                 870                 875                 880

Asn Val Asn Gln Ile Ala Phe Pro Gly Pro Ala Gly Pro Ser Phe Asn
                885                 890                 895

Ser Thr Glu Asp His Ser Lys Trp Cys Val Ser Pro Lys Gly Pro Trp
            900                 905                 910

Thr Cys Val Gly Asp Met Asn Arg Asn Gln Gly Glu Gln Arg Gly
            915                 920                 925

Gly Gly Thr Leu Cys Ala Gln Leu Pro Ala Leu Trp Lys Ala Phe Gln
        930                 935                 940

Pro Leu Val Lys Asn Tyr Gln Pro Cys Asn Gly Met Ala Arg Lys Pro
945                 950                 955                 960

Ser Arg Ala Tyr Lys Ile
            965

<210> SEQ ID NO 19
<211> LENGTH: 958
<212> TYPE: PRT
<213> ORGANISM: Artificial Sequence
<220> FEATURE:
<223> OTHER INFORMATION: Synethetic Sequence

<400> SEQUENCE: 19

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80
```

```
Glu Ser Ala Glu Asn Cys Asp Lys Ser Leu His Thr Leu Phe Gly Asp
                    85                  90                  95
Lys Leu Cys Thr Val Ala Thr Leu Arg Glu Thr Tyr Gly Glu Met Ala
            100                 105                 110
Asp Cys Cys Ala Lys Gln Glu Pro Glu Arg Asn Glu Cys Phe Leu Gln
        115                 120                 125
His Lys Asp Asp Asn Pro Asn Leu Pro Arg Leu Val Arg Pro Glu Val
    130                 135                 140
Asp Val Met Cys Thr Ala Phe His Asp Asn Glu Glu Thr Phe Leu Lys
145                 150                 155                 160
Lys Tyr Leu Tyr Glu Ile Ala Arg Arg His Pro Tyr Phe Tyr Ala Pro
            165                 170                 175
Glu Leu Leu Phe Phe Ala Lys Arg Tyr Lys Ala Ala Phe Thr Glu Cys
        180                 185                 190
Cys Gln Ala Ala Asp Lys Ala Ala Cys Leu Leu Pro Lys Leu Asp Glu
    195                 200                 205
Leu Arg Asp Glu Gly Lys Ala Ser Ser Ala Lys Gln Arg Leu Lys Cys
    210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
            245                 250                 255
Lys Leu Val Thr Asp Leu Thr Lys Val His Thr Glu Cys Cys His Gly
            260                 265                 270
Asp Leu Leu Glu Cys Ala Asp Asp Arg Ala Asp Leu Ala Lys Tyr Ile
        275                 280                 285
Cys Glu Asn Gln Asp Ser Ile Ser Ser Lys Leu Lys Glu Cys Cys Glu
    290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
            325                 330                 335
Lys Asp Val Cys Lys Asn Tyr Ala Glu Ala Lys Asp Val Phe Leu Gly
            340                 345                 350
Met Phe Leu Tyr Glu Tyr Ala Arg Arg His Pro Asp Tyr Ser Val Val
        355                 360                 365
Leu Leu Leu Arg Leu Ala Lys Thr Tyr Glu Thr Thr Leu Glu Lys Cys
    370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
            405                 410                 415
Glu Leu Phe Glu Gln Leu Gly Glu Tyr Lys Phe Gln Asn Ala Leu Leu
        420                 425                 430
Val Arg Tyr Thr Lys Lys Val Pro Gln Val Ser Thr Pro Thr Leu Val
    435                 440                 445
Glu Val Ser Arg Asn Leu Gly Lys Val Gly Ser Lys Cys Cys Lys His
    450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
            485                 490                 495
Val Thr Lys Cys Cys Thr Glu Ser Leu Val Asn Arg Arg Pro Cys Phe
```

```
            500                 505                 510
Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu Gly Gly Gly Gly Ser Gly Gly Gly Gly Ser Gly Gly Gly Gly Ser
            610                 615                 620

Ala Thr Ile Ser Cys Arg Asn Glu Gly Lys Ala Val Asp Trp Phe
625                 630                 635                 640

Thr Phe Tyr Lys Leu Pro Lys Arg Gln Asn Lys Glu Ser Gly Glu Thr
                645                 650                 655

Gly Leu Glu Tyr Leu Tyr Leu Asp Ser Thr Thr Arg Ser Trp Arg Lys
            660                 665                 670

Ser Glu Gln Leu Met Asn Asp Thr Lys Ser Val Leu Gly Arg Thr Leu
            675                 680                 685

Gln Gln Leu Tyr Glu Ala Tyr Ala Ser Lys Ser Asn Asn Thr Ala Tyr
            690                 695                 700

Leu Ile Tyr Asn Asp Gly Val Pro Lys Pro Val Asn Tyr Ser Arg Lys
705                 710                 715                 720

Tyr Gly His Thr Lys Gly Leu Leu Leu Trp Asn Arg Val Gln Gly Phe
                725                 730                 735

Trp Leu Ile His Ser Ile Pro Gln Phe Pro Ile Pro Glu Glu Gly
            740                 745                 750

Tyr Asp Tyr Pro Pro Thr Gly Arg Arg Asn Gly Gln Ser Gly Ile Cys
            755                 760                 765

Ile Thr Phe Lys Tyr Asn Gln Tyr Glu Ala Ile Asp Ser Gln Leu Leu
770                 775                 780

Val Cys Asn Pro Asn Val Tyr Ser Cys Ser Ile Pro Ala Thr Phe His
785                 790                 795                 800

Gln Glu Leu Ile His Met Pro Gln Leu Cys Thr Arg Ala Ser Ser Ser
                805                 810                 815

Glu Ile Pro Gly Arg Leu Leu Thr Thr Leu Gln Ser Ala Gln Gly Gln
            820                 825                 830

Lys Phe Leu His Phe Ala Lys Ser Asp Ser Phe Leu Asp Asp Ile Phe
            835                 840                 845

Ala Ala Trp Met Ala Gln Arg Leu Lys Thr His Leu Leu Thr Glu Thr
            850                 855                 860

Trp Gln Arg Lys Arg Gln Glu Leu Pro Ser Asn Cys Ser Leu Pro Tyr
865                 870                 875                 880

His Val Tyr Asn Ile Lys Ala Ile Lys Leu Ser Arg His Ser Tyr Phe
                885                 890                 895

Ser Ser Tyr Gln Asp His Ala Lys Trp Cys Ile Ser Gln Lys Gly Thr
            900                 905                 910

Lys Asn Arg Trp Thr Cys Ile Gly Asp Leu Asn Arg Ser Pro His Gln
            915                 920                 925
```

```
Ala Phe Arg Ser Gly Gly Phe Ile Cys Thr Gln Asn Trp Gln Ile Tyr
    930                 935                 940

Gln Ala Phe Gln Gly Leu Val Leu Tyr Tyr Glu Ser Cys Lys
945                 950                 955
```

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<211> LENGTH: 282
<212> TYPE: PRT
<213> ORGANISM: Artificial Sequence
<220> FEATURE:
<223> OTHER INFORMATION: Synthetic Sequence

<400> SEQUENCE: 30

```
Met Ser Arg Glu Leu Ala Pro Leu Leu Leu Leu Ser Ile His
1               5                  10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Glu Ala Leu Asp Val Ser
            260                 265                 270

Asp His Phe Pro Val Glu Phe Lys Leu Lys
        275                 280
```

<210> SEQ ID NO 31
<211> LENGTH: 310
<212> TYPE: PRT
<213> ORGANISM: Mus musculus

<400> SEQUENCE: 31

```
Met Ser Leu His Pro Ala Ser Pro Arg Leu Ala Ser Leu Leu Leu Phe
1               5                   10                  15

Ile Leu Ala Leu His Asp Thr Leu Ala Leu Arg Leu Cys Ser Phe Asn
            20                  25                  30

Val Arg Ser Phe Gly Ala Ser Lys Lys Glu Asn His Glu Ala Met Asp
        35                  40                  45
```

```
Ile Ile Val Lys Ile Ile Lys Arg Cys Asp Leu Ile Leu Leu Met Glu
 50                  55                  60

Ile Lys Asp Ser Asn Asn Ile Cys Pro Met Leu Met Glu Lys Leu
 65                  70                  75                  80

Asn Gly Asn Ser Arg Arg Ser Thr Thr Tyr Asn Tyr Val Ile Ser Ser
                 85                  90                  95

Arg Leu Gly Arg Asn Thr Tyr Lys Glu Gln Tyr Ala Phe Val Tyr Lys
            100                 105                 110

Glu Lys Leu Val Ser Val Lys Thr Lys Tyr His Tyr His Asp Tyr Gln
        115                 120                 125

Asp Gly Asp Thr Asp Val Phe Ser Arg Glu Pro Phe Val Val Trp Phe
    130                 135                 140

His Ser Pro Phe Thr Ala Val Lys Asp Phe Val Ile Val Pro Leu His
145                 150                 155                 160

Thr Thr Pro Glu Thr Ser Val Lys Glu Ile Asp Glu Leu Val Asp Val
                165                 170                 175

Tyr Thr Asp Val Arg Ser Gln Trp Lys Thr Glu Asn Phe Ile Phe Met
            180                 185                 190

Gly Asp Phe Asn Ala Gly Cys Ser Tyr Val Pro Lys Lys Ala Trp Gln
        195                 200                 205

Asn Ile Arg Leu Arg Thr Asp Pro Lys Phe Val Trp Leu Ile Gly Asp
    210                 215                 220

Gln Glu Asp Thr Thr Val Lys Lys Ser Thr Ser Cys Ala Tyr Asp Arg
225                 230                 235                 240

Ile Val Leu Cys Gly Gln Glu Ile Val Asn Ser Val Val Pro Arg Ser
                245                 250                 255

Ser Gly Val Phe Asp Phe Gln Lys Ala Tyr Asp Leu Ser Glu Glu Glu
            260                 265                 270

Ala Leu Asp Val Ser Asp His Phe Pro Val Glu Phe Lys Leu Gln Ser
        275                 280                 285

Ser Arg Ala Phe Thr Asn Asn Arg Lys Ser Val Ser Leu Lys Lys Arg
    290                 295                 300

Lys Lys Gly Asn Arg Ser
305                 310

<210> SEQ ID NO 32
<211> LENGTH: 310
<212> TYPE: PRT
<213> ORGANISM: Rattus norvegicus

<400> SEQUENCE: 32

Met Ser Leu Tyr Pro Ala Ser Pro Tyr Leu Ala Ser Leu Leu Leu Phe
 1               5                  10                  15

Ile Leu Ala Leu His Gly Ala Leu Ser Leu Arg Leu Cys Ser Phe Asn
                20                  25                  30

Val Arg Ser Phe Gly Glu Ser Lys Lys Glu Asn His Asn Ala Met Asp
            35                  40                  45

Ile Ile Val Lys Ile Ile Lys Arg Cys Asp Leu Ile Leu Leu Met Glu
        50                  55                  60

Ile Lys Asp Ser Asn Asn Ile Cys Pro Met Leu Met Glu Lys Leu
 65                  70                  75                  80

Asn Gly Asn Ser Arg Arg Ser Thr Thr Tyr Asn Tyr Val Ile Ser Ser
                 85                  90                  95

Arg Leu Gly Arg Asn Thr Tyr Lys Glu Gln Tyr Ala Phe Leu Tyr Lys
            100                 105                 110
```

```
Glu Lys Leu Val Ser Val Lys Ala Lys Tyr Leu Tyr His Asp Tyr Gln
            115                 120                 125

Asp Gly Asp Thr Asp Val Phe Ser Arg Glu Pro Phe Val Val Trp Phe
130                 135                 140

Gln Ala Pro Phe Thr Ala Ala Lys Asp Phe Val Ile Val Pro Leu His
145                 150                 155                 160

Thr Thr Pro Glu Thr Ser Val Lys Glu Ile Asp Glu Leu Ala Asp Val
                165                 170                 175

Tyr Thr Asp Val Arg Arg Arg Trp Lys Ala Glu Asn Phe Ile Phe Met
            180                 185                 190

Gly Asp Phe Asn Ala Gly Cys Ser Tyr Val Pro Lys Lys Ala Trp Lys
            195                 200                 205

Asn Ile Arg Leu Arg Thr Asp Pro Asn Phe Val Trp Leu Ile Gly Asp
210                 215                 220

Gln Glu Asp Thr Thr Val Lys Lys Ser Thr Ser Cys Ala Tyr Asp Arg
225                 230                 235                 240

Ile Val Leu Arg Gly Gln Glu Ile Val Asn Ser Val Val Pro Arg Ser
                245                 250                 255

Ser Gly Val Phe Asp Phe Gln Lys Ala Tyr Glu Leu Ser Glu Glu Glu
            260                 265                 270

Ala Leu Asp Val Ser Asp His Phe Pro Val Glu Phe Lys Leu Gln Ser
            275                 280                 285

Ser Arg Ala Phe Thr Asn Ser Arg Lys Ser Val Ser Leu Lys Lys Lys
            290                 295                 300

Lys Lys Gly Ser Arg Ser
305                 310

<210> SEQ ID NO 33
<211> LENGTH: 305
<212> TYPE: PRT
<213> ORGANISM: Pan troglodytes

<400> SEQUENCE: 33

Met Ser Arg Glu Leu Thr Pro Leu Leu Leu Leu Leu Ser Ile His
1               5                   10                  15

Ser Thr Leu Ala Leu Arg Ile Cys Ser Phe Asn Val Arg Ser Phe Gly
                20                  25                  30

Glu Ser Lys Gln Glu Asp Gln Asn Ala Met Asp Val Ile Val Lys Val
            35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
            115                 120                 125

Val Phe Ser Arg Glu Pro Phe Val Val Trp Phe Gln Ser Pro His Thr
            130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
```

```
                165                 170                 175
His Arg Trp Lys Ala Glu Asn Phe Ile Phe Met Gly Asp Phe Asn Ala
                180                 185                 190

Gly Cys Ser Tyr Val Pro Lys Lys Ala Trp Lys Asn Ile Arg Leu Arg
                195                 200                 205

Thr Asp Pro Arg Phe Val Trp Leu Ile Gly Asp Gln Glu Asp Thr Thr
        210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asp
                245                 250                 255

Phe Gln Lys Ala Tyr Lys Leu Thr Glu Glu Ala Leu Asp Val Ser
                260                 265                 270

Asp His Phe Pro Val Glu Phe Lys Leu Gln Ser Ser Arg Ala Phe Thr
                275                 280                 285

Asn Ser Lys Lys Ser Val Thr Leu Arg Lys Lys Thr Lys Ser Lys Arg
        290                 295                 300

Ser
305

<210> SEQ ID NO 34
<211> LENGTH: 305
<212> TYPE: PRT
<213> ORGANISM: Olive baboon

<400> SEQUENCE: 34

Met Ser Gln Glu Leu Ala Pro Leu Leu Leu Leu Leu Ser Ile His
1               5                   10                  15

Ser Ala Leu Ala Leu Arg Ile Cys Ser Phe Asn Val Arg Ser Phe Gly
                20                  25                  30

Glu Ser Lys Gln Glu Asp Gln Asn Ala Met Asp Val Ile Val Lys Val
            35                  40                  45

Ile Lys Arg Cys Asp Ile Met Leu Leu Met Glu Ile Lys Asp Ser Asn
50                  55                  60

Asn Arg Ile Cys Pro Val Leu Met Glu Lys Leu Asn Gly Asn Ser Arg
65                  70                  75                  80

Arg Gly Ile Met Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Val Asp
            115                 120                 125

Val Phe Ser Arg Glu Pro Phe Val Val Trp Phe Gln Ser Pro His Thr
        130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Asp Val Tyr Met Asp Met Lys
                165                 170                 175

His Arg Trp Lys Ala Glu Asn Phe Ile Phe Met Gly Asp Phe Asn Ala
                180                 185                 190

Gly Cys Ser Tyr Val Pro Lys Lys Ala Trp Lys Asn Ile Arg Leu Arg
                195                 200                 205

Thr Asp Pro Arg Phe Val Trp Leu Ile Gly Asp Gln Glu Asp Thr Thr
        210                 215                 220
```

```
Val Lys Arg Ser Thr Lys Cys Ala Tyr Asp Arg Ile Val Leu Arg Gly
225                 230                 235                 240

Gln Glu Ile Val Ser Ser Val Val Pro Lys Ser Asn Ser Val Phe Asp
            245                 250                 255

Phe Gln Lys Ala Tyr Lys Leu Thr Glu Glu Ala Leu Asp Val Ser
        260                 265                 270

Asp His Phe Pro Val Glu Phe Lys Leu Gln Ser Ser Arg Ala Phe Thr
        275                 280                 285

Asn Ser Lys Lys Ser Val Thr Val Arg Lys Lys Thr Lys Ser Lys Arg
290                 295                 300

Ser
305

<210> SEQ ID NO 35
<211> LENGTH: 307
<212> TYPE: PRT
<213> ORGANISM: Rabbit

<400> SEQUENCE: 35

Met Ser Leu Gly Met Ser Pro Ala Ser Leu Leu Leu Leu Leu Leu Cys
1               5                   10                  15

Leu His Gly Ala Leu Ala Leu Lys Leu Cys Ser Phe Asn Val Arg Ser
                20                  25                  30

Phe Gly Tyr Ser Lys Arg Glu Asn Arg Gln Ala Met Asp Val Ile Val
            35                  40                  45

Lys Ile Ile Lys Arg Cys Asp Ile Ile Leu Met Glu Ile Lys Asp
        50                  55                  60

Ser Asn Asn Met Ile Cys Pro Thr Leu Met Glu Lys Leu Asn Gly Asn
65                  70                  75                  80

Ser Arg Arg Gly Ile Thr Tyr Asn Tyr Val Ile Ser Ser Arg Leu Gly
                85                  90                  95

Arg Asn Val Tyr Lys Glu Gln Tyr Ala Phe Leu Tyr Lys Glu Lys Leu
                100                 105                 110

Val Thr Val Lys Lys Asn Tyr Leu Tyr His Asp Tyr Glu Ala Gly Asp
            115                 120                 125

Ala Asp Ala Phe Ser Arg Glu Pro Tyr Val Val Trp Phe Gln Ser Pro
130                 135                 140

Phe Thr Ala Val Lys Asp Phe Val Ile Val Pro Leu His Thr Ser Pro
145                 150                 155                 160

Glu Ala Ser Val Lys Glu Ile Asp Glu Leu Val Asp Val Tyr Met Asp
                165                 170                 175

Val Lys Arg Arg Trp Asn Ala Glu Asn Phe Ile Phe Met Gly Asp Phe
            180                 185                 190

Asn Ala Gly Cys Ser Tyr Val Pro Lys Lys Ala Trp Lys Asn Ile Arg
        195                 200                 205

Leu Arg Thr Asp Pro Arg Phe Val Trp Leu Ile Gly Asp Glu Glu Asp
210                 215                 220

Thr Thr Val Lys Lys Ser Thr Ser Cys Ala Tyr Asp Arg Ile Val Leu
225                 230                 235                 240

Arg Gly Gln Asp Ile Ile Arg Ser Val Val Pro Asp Ser Asn Gly Val
                245                 250                 255

Phe Asp Phe Arg Lys Ala Tyr Lys Leu Thr Glu Glu Ala Leu Asp
        260                 265                 270

Val Ser Asp His Phe Pro Val Glu Phe Lys Leu Gln Ser Ser Thr Ala
275                 280                 285
```

```
Phe Thr Asn Ser Lys Lys Ser Val Gln Pro Arg Lys Lys Ala Lys Ala
            290                 295                 300

Lys Arg Ser
305

<210> SEQ ID NO 36
<211> LENGTH: 304
<212> TYPE: PRT
<213> ORGANISM: Dog

<400> SEQUENCE: 36

Met Pro Arg Leu Pro Ala Phe Leu Leu Phe Leu Leu Leu Ser Ile Ser
  1               5                  10                  15

Ser Ala Leu Ala Leu Arg Leu Cys Ser Phe Asn Val Arg Ser Phe Gly
             20                  25                  30

Gly Ala Lys Arg Glu Asn Lys Asn Ala Met Asp Val Ile Val Lys Val
         35                  40                  45

Ile Lys Arg Cys Asp Ile Ile Leu Leu Met Glu Val Lys Asp Ser Asn
 50                  55                  60

Asn Met Ile Cys Pro Thr Leu Leu Glu Lys Leu Asn Gly Asn Ser Arg
 65                  70                  75                  80

Arg Gly Ile Lys Tyr Asn Tyr Val Ile Ser Ser Arg Leu Gly Arg Asn
                 85                  90                  95

Thr Tyr Lys Glu Gln Tyr Ala Phe Leu Tyr Lys Glu Lys Leu Val Ser
            100                 105                 110

Val Lys Lys Tyr Tyr Leu Tyr His Asp Tyr Gln Ala Gly Asp Ala Asp
        115                 120                 125

Val Phe Ser Arg Glu Pro Phe Val Val Trp Phe Gln Ser Pro Phe Thr
130                 135                 140

Ala Val Lys Asp Phe Val Ile Val Pro Leu His Thr Thr Pro Glu Ala
145                 150                 155                 160

Ser Val Lys Glu Ile Asp Glu Leu Val Asp Val Tyr Leu Asp Val Lys
                165                 170                 175

Arg Arg Trp Lys Ala Glu Asn Phe Ile Phe Met Gly Asp Phe Asn Ala
            180                 185                 190

Gly Cys Ser Tyr Val Pro Lys Lys Ala Trp Lys Ile Ile Arg Leu Arg
        195                 200                 205

Thr Asp Pro Gly Phe Val Trp Leu Ile Gly Asp Gln Glu Asp Thr Thr
210                 215                 220

Val Lys Ser Ser Thr His Cys Ala Tyr Asp Arg Ile Val Leu Arg Gly
225                 230                 235                 240

Pro Glu Ile Ile Arg Ser Val Val Pro Arg Ser Asn Ser Thr Phe Asp
                245                 250                 255

Phe Gln Lys Ala Phe Leu Leu Thr Glu Glu Ala Leu Asn Val Ser
            260                 265                 270

Asp His Phe Pro Val Glu Phe Lys Leu Gln Ser Ser Arg Ala Phe Thr
        275                 280                 285

Asn Ser Lys Lys Ser Ile Ser Pro Lys Lys Lys Val Arg His Pro
290                 295                 300

<210> SEQ ID NO 37
<211> LENGTH: 312
<212> TYPE: PRT
<213> ORGANISM: Pig

<400> SEQUENCE: 37
```

Met Ser Gln Leu Leu Val Ser Leu Met Leu Leu Leu Ser Thr His
1               5                   10                  15

Ser Ser Leu Ala Leu Arg Ile Cys Ser Phe Asn Val Arg Ser Phe Gly
                20                  25                  30

Glu Ser Lys Lys Ala Asn Cys Asn Ala Met Asp Val Ile Val Lys Val
            35                  40                  45

Ile Lys Arg Cys Asp Ile Ile Leu Leu Met Glu Ile Lys Asp Ser Asn
        50                  55                  60

Asn Met Ile Cys Pro Thr Leu Met Glu Lys Leu Asn Gly Asn Ser Arg
65                  70                  75                  80

Arg Ser Val Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Lys Ser Tyr Leu Tyr His Asp Tyr Gln Ser Gly Asp Ala Asp
        115                 120                 125

Val Phe Ser Arg Glu Pro Phe Val Val Trp Phe Gln Ser Pro Tyr Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Asp Val Tyr Leu Asp Val Lys
                165                 170                 175

Arg Arg Trp Glu Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Met Phe Ile Trp Leu Ile Lys Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Gly Ser Asn Ser Ile Phe Asp
                245                 250                 255

Phe Gln Lys Ala Tyr Arg Leu Thr Glu Glu Lys Val Arg Leu Ser Phe
            260                 265                 270

Cys Leu Ser Val Ser Pro Ser Gly Glu Asp Gly Val Val Ser Pro Arg
        275                 280                 285

Gly Ile Gln Ala Thr Thr Gly Asp Thr Leu Gly His Leu Thr Leu Ser
        290                 295                 300

Phe Lys Ala Asn Asp Ser Leu Thr
305                 310

<210> SEQ ID NO 38
<211> LENGTH: 302
<212> TYPE: PRT
<213> ORGANISM: Guinea pig

<400> SEQUENCE: 38

Met Ser Gln Thr Arg Pro Ser Leu Leu Leu Leu Leu Ala Ile His
1               5                   10                  15

Gly Ala Leu Ala Leu Lys Leu Cys Ser Phe Asn Val Arg Ser Phe Gly
                20                  25                  30

Glu Ser Lys Lys Gln Asn Gln Asn Ala Met Asp Val Ile Val Lys Ile
            35                  40                  45

Ile Lys Arg Cys Asp Leu Met Leu Leu Met Glu Ile Lys Asp Ser His

```
                50                  55                  60
Asn Arg Ile Cys Pro Met Leu Met Glu Lys Leu Asn Gly Asn Ser Arg
 65                  70                  75                  80

Arg Gly Thr Thr Tyr Asn Tyr Val Ile Ser Ser Arg Leu Gly Arg Asn
                 85                  90                  95

Thr Tyr Lys Glu Gln Tyr Ala Phe Leu Tyr Lys Glu Lys Leu Val Thr
                100                 105                 110

Val Lys Asp Asn Tyr Leu Phe His Asp Glu Asp Ala Asp Val Phe Ser
                115                 120                 125

Arg Glu Pro Tyr Val Val Trp Phe Gln Ser Pro His Thr Ala Val Lys
                130                 135                 140

Asp Phe Val Ile Val Pro Leu His Thr Thr Pro Glu Thr Ser Val Lys
145                 150                 155                 160

Glu Ile Asp Glu Leu Ala Asp Val Tyr Thr Asp Val Gln Arg Gln Trp
                165                 170                 175

Lys Val Ala Asn Phe Ile Phe Met Gly Asp Phe Asn Ala Gly Cys Ser
                180                 185                 190

Tyr Val Pro Lys Lys Ala Trp Lys Asn Ile Arg Leu Arg Thr Asp Pro
                195                 200                 205

Lys Phe Val Trp Leu Ile Ala Asp Asp Glu Asp Thr Thr Val Lys Lys
                210                 215                 220

Ser Thr Ser Cys Ala Tyr Asp Arg Ile Val Leu Arg Gly Gln Glu Ile
225                 230                 235                 240

Val Asn Ser Val Val Pro Asn Ser Asn Gly Val Phe Asp Phe Gln Lys
                245                 250                 255

Ala Tyr Gln Leu Ser Glu Gln Ala Leu Glu Val Ser Asp His Phe
                260                 265                 270

Pro Val Glu Phe Lys Leu Gln Ser Glu Arg Ala Phe Thr Asn Asn Lys
                275                 280                 285

Lys Ser Val Ser Leu Lys Lys Lys Lys Ala Asn Arg Ser
                290                 295                 300

<210> SEQ ID NO 39
<211> LENGTH: 305
<212> TYPE: PRT
<213> ORGANISM: Cow

<400> SEQUENCE: 39

Met Pro Leu Pro Leu Ala Cys Leu Leu Leu Leu Leu Ser Thr His
 1               5                  10                  15

Ser Ala Leu Ala Leu Lys Ile Cys Ser Phe Asn Val Arg Ser Phe Gly
                 20                  25                  30

Glu Ser Lys Lys Ala Asn Cys Asn Ala Met Asp Val Ile Val Lys Val
                 35                  40                  45

Ile Lys Arg Cys Asp Ile Ile Leu Leu Met Glu Ile Lys Asp Ser Ser
 50                  55                  60

Asn Arg Ile Cys Pro Thr Leu Met Glu Lys Leu Asn Gly Asn Ser Arg
 65                  70                  75                  80

Lys Gly Ile Thr Tyr Asn Tyr Val Ile Ser Ser Arg Leu Gly Arg Asn
                 85                  90                  95

Thr Tyr Lys Glu Gln Tyr Ala Phe Leu Tyr Lys Glu Lys Leu Val Ser
                100                 105                 110

Val Lys Gln Ser Tyr Leu Tyr His Asp Tyr Gln Ala Gly Asp Ala Asp
                115                 120                 125
```

Val Phe Ser Arg Glu Pro Phe Val Val Trp Phe Gln Ser Pro Tyr Thr
130                 135                 140

Ala Val Lys Asp Phe Val Ile Val Pro Leu His Thr Thr Pro Glu Thr
145                 150                 155                 160

Ser Val Arg Glu Ile Asp Glu Leu Ala Asp Val Tyr Thr Asp Val Lys
            165                 170                 175

Arg Arg Trp Asn Ala Glu Asn Phe Ile Phe Met Gly Asp Phe Asn Ala
            180                 185                 190

Gly Cys Ser Tyr Val Pro Lys Lys Ala Trp Lys Asp Ile Arg Leu Arg
            195                 200                 205

Thr Asp Pro Lys Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Asn Ile Val Asn Ser Val Val Pro Gln Ser Asn Leu Val Phe Asp
                245                 250                 255

Phe Gln Lys Ala Tyr Arg Leu Ser Glu Ser Lys Ala Leu Asp Val Ser
            260                 265                 270

Asp His Phe Pro Val Glu Phe Lys Leu Gln Ser Ser Arg Ala Phe Thr
275                 280                 285

Asn Ser Lys Lys Ser Val Ser Ser Lys Lys Lys Lys Thr Ser His
290                 295                 300

Ala
305

<210> SEQ ID NO 40
<211> LENGTH: 309
<212> TYPE: PRT
<213> ORGANISM: Elephant

<400> SEQUENCE: 40

Arg Ser Ala Arg Met Ser Gln Ser Leu Pro Ala Leu Leu Leu Leu Leu
1               5                   10                  15

Leu Leu Ser Val His Gly Thr Leu Ala Leu Arg Val Cys Ser Phe Asn
            20                  25                  30

Val Arg Ser Phe Gly Glu Thr Lys Arg Glu Asn Gln Lys Val Met Asp
            35                  40                  45

Ile Ile Val Lys Ile Ile Lys Arg Cys Asp Ile Met Leu Leu Met Glu
        50                  55                  60

Ile Lys Asp Ser Asn Asn Arg Ile Cys Pro Met Leu Leu Lys Arg Leu
65                  70                  75                  80

Asn Gly Asn Ser Arg Arg Gly Ile Lys Tyr Asn Tyr Val Ile Ser Pro
                85                  90                  95

Arg Leu Gly Arg Asn Ala Tyr Lys Glu Gln Tyr Ala Phe Leu Tyr Met
            100                 105                 110

Glu Lys Leu Leu Ser Val Lys Lys Ser Tyr Val Tyr Gly Asp Asn Gln
            115                 120                 125

Asn Gly Asp Ala Asp Val Phe Ser Arg Glu Pro Phe Val Thr Trp Phe
130                 135                 140

Gln Ser Pro His Thr Ala Val Lys Asp Phe Val Ile Val Pro Leu His
145                 150                 155                 160

Thr Thr Pro Glu Thr Ser Ile Lys Glu Ile Asp Glu Leu Val Asp Val
            165                 170                 175

Tyr Met Asp Val Lys Lys Arg Trp Asn Ala Gln Asn Phe Ile Phe Met
            180                 185                 190

```
Gly Asp Phe Asn Ala Gly Cys Ser Tyr Val Pro Lys Lys Ser Trp Arg
        195                 200                 205

Asn Ile Arg Leu Arg Thr Asp Pro Gly Phe Val Trp Leu Ile Gly Asp
    210                 215                 220

Gln Glu Asp Thr Thr Val Lys Glu Ser Thr Asn Cys Ala Tyr Asp Arg
225                 230                 235                 240

Ile Val Leu Arg Gly Gln Ile Ile Ser Val Val Pro Asn Ser Asn
                245                 250                 255

Ser Ile Phe Asn Phe Gln Lys Ala Tyr Glu Leu Ser Glu Glu Glu Ala
            260                 265                 270

Leu Asn Ile Ser Asp His Phe Pro Val Glu Phe Lys Leu Gln Ser Ser
        275                 280                 285

Arg Ala Ile Thr Asn Ser Lys Lys Ser Val Ser Pro Lys Lys Lys Lys
    290                 295                 300

Lys Ala Lys Ser Ser
305

<210> SEQ ID NO 41
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 41

Gly Gly Gly Gly Ser
1               5

<210> SEQ ID NO 42
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 42

Gly Gly Gly Gly Ser Gly Gly Gly Gly Ser Gly Gly Gly Gly Ser
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 43

Ala Pro Ala Pro Ala Pro Ala Pro Ala Pro Ala Pro Ala Pro
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 44

Ala Glu Ala Ala Ala Lys Glu Ala Ala Ala Lys Ala
1               5                   10

<210> SEQ ID NO 45
```

```
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 45

Ser Gly Gly Ser Gly Ser Ser
1               5

<210> SEQ ID NO 46
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 46

Ser Gly Gly Ser Gly Gly Ser Gly Gly Ser Gly Gly Ser Gly Ser Ser
1               5                   10                  15

<210> SEQ ID NO 47
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 47

Ser Gly Gly Ser Gly Gly Ser Gly Gly Ser Gly Gly Ser Gly Gly Ser
1               5                   10                  15

Gly Gly Ser Gly Gly Ser Gly Gly Ser Gly Gly Ser Gly Ser
            20                  25                  30

<210> SEQ ID NO 48
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 48

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Ser
            20                  25

<210> SEQ ID NO 49
<211> LENGTH: 25
<212> TYPE: PRT
<213> ORGANISM: Homo sapiens

<400> SEQUENCE: 49

Cys Thr Thr Lys Ile Lys Pro Arg Ile Val Gly Gly Thr Ala Ser Val
1               5                   10                  15

Arg Gly Glu Trp Pro Trp Gln Val Thr
            20                  25

<210> SEQ ID NO 50
<211> LENGTH: 7
<212> TYPE: PRT
<213> ORGANISM: Homo sapiens

<400> SEQUENCE: 50

Ser Thr Arg Ile Val Gly Gly
1               5
```

```
1              5

<210> SEQ ID NO 51
<211> LENGTH: 26
<212> TYPE: PRT
<213> ORGANISM: Homo sapiens

<400> SEQUENCE: 51

Val Cys Thr Thr Lys Thr Ser Thr Arg Ile Val Gly Gly Thr Asn Ser
1               5                   10                  15

Ser Trp Gly Glu Trp Pro Trp Gln Val Ser
            20                  25
```